(12) United States Patent
Messerly et al.

(10) Patent No.: US 10,779,847 B2
(45) Date of Patent: Sep. 22, 2020

(54) ULTRASONIC TRANSDUCER TO WAVEGUIDE JOINING

(71) Applicant: Ethicon LLC, Guaynabo, PR (US)

(72) Inventors: Jeffrey D. Messerly, Cincinnati, OH (US); Brian D. Black, Loveland, OH (US); Frederick Estera, Cincinnati, OH (US); Jason R. Lesko, Cincinnati, OH (US); Benjamin M. Boyd, Fairborn, OH (US); Kevin M. Fiebig, Cincinnati, OH (US); Chad P. Boudreaux, Cincinnati, OH (US); Grace E. Waters, Cincinnati, OH (US); Kristen G. Denzinger, Cincinnati, OH (US); Amy M. Krumm, Cincinnati, OH (US); Amelia A. Pierce, Cincinnati, OH (US); Chad E. Eckert, Terrace Park, OH (US); Joseph D. Dennis, Wyoming, OH (US); Ion V. Nicolaescu, Carpentersville, IL (US); Monica L. Zeckel, Cincinnati, OH (US); William A. Olson, Lebanon, OH (US); Patrick J. Scoggins, Loveland, OH (US); Larry A. Pummill, Jr., Germantown, OH (US); John S. Frazier, Englewood, OH (US); William A. Crawford, Batavia, OH (US); Brian J. Hemmelgarn, Dayton, OH (US); Eric Stout, Fort Wayne, IN (US); Benjamin D. Dickerson, Cincinnati, OH (US)

(73) Assignee: Ethicon LLC, Guaynabo, PR (US)

(*) Notice: Subject to any disclaimer, the term of this patent is extended or adjusted under 35 U.S.C. 154(b) by 236 days.

(21) Appl. No.: 15/679,960

(22) Filed: Aug. 17, 2017

(65) Prior Publication Data
US 2018/0055532 A1 Mar. 1, 2018

Related U.S. Application Data

(60) Provisional application No. 62/379,550, filed on Aug. 25, 2016.

(51) Int. Cl.
*A61B 17/32* (2006.01)
*H01L 41/053* (2006.01)
(Continued)

(52) U.S. Cl.
CPC ........... *A61B 17/320068* (2013.01); *A61B 17/00234* (2013.01); *A61N 7/02* (2013.01);
(Continued)

(58) Field of Classification Search
CPC ...... A61B 17/00234; A61B 17/320068; A61B 2017/00017; A61B 2017/00402;
(Continued)

(56) References Cited

U.S. PATENT DOCUMENTS 969,528 A 9/1910 Disbrow
1,570,025 A 1/1926 Young
(Continued)

FOREIGN PATENT DOCUMENTS

CA 2535467 A1 4/1993
CA 2214413 A1 9/1996
(Continued)

OTHER PUBLICATIONS

Technology Overview, printed from www.harmonicscalpel.com, Internet site, website accessed on Jun. 13, 2007, (3 pages).
(Continued)

*Primary Examiner* — George J Ulsh

(57) ABSTRACT

Aspects of the present disclosure include various ultrasonic surgical instruments. At least one disclosed surgical instrument includes a waveguide including a blade and a trans-
(Continued)

ducer base plate. The transducer base plate may be coupled to the waveguide to define a tapered joint at an interface between the waveguide and the transducer base plate. The transducer base plate may include first and second sides defining corresponding first and second flat faces configured to receive first and second piezoelectric elements. The first and second piezoelectric elements are configured to operate in a D31 mode.

4 Claims, 32 Drawing Sheets

(51) Int. Cl.
  H01L 41/083 (2006.01)
  H01L 41/09 (2006.01)
  A61B 17/00 (2006.01)
  B29C 65/48 (2006.01)
  A61N 7/02 (2006.01)
  A61B 17/22 (2006.01)
  A61B 17/29 (2006.01)
  B29L 31/00 (2006.01)
  A61B 17/16 (2006.01)
  A61B 18/00 (2006.01)

(52) U.S. Cl.
  CPC ...... *B29C 65/4805* (2013.01); *H01L 41/0536* (2013.01); *H01L 41/083* (2013.01); *H01L 41/0835* (2013.01); *H01L 41/0986* (2013.01); *A61B 17/1628* (2013.01); *A61B 2017/00017* (2013.01); *A61B 2017/0088* (2013.01); *A61B 2017/00402* (2013.01); *A61B 2017/00477* (2013.01); *A61B 2017/00526* (2013.01); *A61B 2017/22027* (2013.01); *A61B 2017/294* (2013.01); *A61B 2017/32007* (2017.08); *A61B 2017/320074* (2017.08); *A61B 2017/320082* (2017.08); *A61B 2017/320088* (2013.01); *A61B 2017/320089* (2017.08); *A61B 2017/320098* (2017.08); *A61B 2018/00565* (2013.01); *A61B 2018/00589* (2013.01); *A61B 2018/00595* (2013.01); *B29L 2031/7546* (2013.01)

(58) Field of Classification Search
  CPC .. A61B 2017/0088; A61B 2017/00477; A61B 2017/00526; A61B 17/1628; A61B 2017/22027; A61B 2017/294; A61B 2017/32007; A61B 2017/320074; A61B 2017/320082; A61B 2017/320088; A61B 2017/320089; A61B 2017/320098; A61B 2018/00565; A61B 2018/00589; A61B 2018/00595; A61N 7/02; B29C 65/4805; H01L 41/083; H01L 41/0536; H01L 41/0835; H01L 41/0986; B29L 2031/7546
  See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,743,726 A | 5/1956 | Grieshaber |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,503,396 A | 3/1970 | Pierie et al. |
| 3,503,397 A | 3/1970 | Fogarty et al. |
| 3,503,398 A | 3/1970 | Fogarty et al. |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,792,701 A | 2/1974 | Kloz et al. |
| 3,805,787 A | 4/1974 | Banko |
| 3,809,977 A | 5/1974 | Balamuth et al. |
| 3,830,098 A | 8/1974 | Antonevich |
| 3,832,776 A | 9/1974 | Sawyer |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,085,893 A | 4/1978 | Durley, III |
| 4,156,187 A | 5/1979 | Murry et al. |
| 4,167,944 A | 9/1979 | Banko |
| 4,173,725 A | 11/1979 | Asai et al. |
| 4,188,927 A | 2/1980 | Harris |
| 4,193,009 A | 3/1980 | Durley, III |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |

(56) References Cited

U.S. PATENT DOCUMENTS

| | | |
|---|---|---|
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,663,677 A | 5/1987 | Griffith et al. |
| 4,674,502 A | 6/1987 | Imonti |
| 4,708,127 A | 11/1987 | Abdelghani |
| 4,712,722 A | 12/1987 | Hood et al. |
| 4,735,603 A | 4/1988 | Goodson et al. |
| 4,750,488 A | 6/1988 | Wuchinich et al. |
| 4,761,871 A | 8/1988 | O'Connor et al. |
| 4,808,154 A | 2/1989 | Freeman |
| 4,819,635 A | 4/1989 | Shapiro |
| 4,821,719 A | 4/1989 | Fogarty |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,869,715 A | 9/1989 | Sherburne |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 4,983,160 A | 1/1991 | Steppe et al. |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,061,269 A | 10/1991 | Muller |
| 5,084,052 A | 1/1992 | Jacobs |
| 5,088,687 A | 2/1992 | Stender |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| D330,253 S | 10/1992 | Burek |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,103 A | 5/1993 | Martin et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,234,428 A | 8/1993 | Kaufman |
| 5,234,436 A | 8/1993 | Eaton et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,323,055 A | 6/1994 | Yamazaki |
| 5,324,299 A | 6/1994 | Davison et al. |
| 5,326,013 A | 7/1994 | Green et al. |
| 5,326,342 A | 7/1994 | Pflueger et al. |

(56) References Cited

U.S. PATENT DOCUMENTS

| | | |
|---|---|---|
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,354,265 A | 10/1994 | Mackool |
| 5,357,164 A | 10/1994 | Imabayashi et al. |
| 5,357,423 A | 10/1994 | Weaver et al. |
| 5,358,506 A | 10/1994 | Green et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| 5,409,453 A | 4/1995 | Lundquist et al. |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,577,654 A | 11/1996 | Bishop |
| 5,582,618 A | 12/1996 | Chin et al. |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,643,301 A | 7/1997 | Mollenauer |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |

(56) References Cited

U.S. PATENT DOCUMENTS

| | | |
|---|---|---|
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,971,949 A | 10/1999 | Levin et al. |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,007,552 A | 12/1999 | Fogarty et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| 6,120,519 A | 9/2000 | Weber et al. |
| H1904 H | 10/2000 | Yates et al. |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |

(56) References Cited

U.S. PATENT DOCUMENTS

| | | | |
|---|---|---|---|
| 6,162,208 A | 12/2000 | Hipps |
| 6,165,150 A | 12/2000 | Banko |
| 6,165,186 A | 12/2000 | Fogarty et al. |
| 6,165,191 A | 12/2000 | Shibata et al. |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,228,104 B1 | 5/2001 | Fogarty et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,273,902 B1 | 8/2001 | Fogarty et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,293,954 B1 | 9/2001 | Fogarty et al. |
| 6,299,591 B1 | 10/2001 | Banko |
| 6,299,621 B1 | 10/2001 | Fogarty et al. |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,312,445 B1 | 11/2001 | Fogarty et al. |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,333,488 B1 | 12/2001 | Lawrence et al. |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,387,112 B1 | 5/2002 | Fogarty et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,425,907 B1 | 7/2002 | Shibata et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,286 B2 | 10/2002 | Mastri et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,569,178 B1 | 5/2003 | Miyawaki et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |

(56) References Cited

U.S. PATENT DOCUMENTS

| | | |
|---|---|---|
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,599,288 B2 | 7/2003 | Maguire et al. |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,696 B2 | 12/2003 | Bacher et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,766 B1 | 4/2004 | Buelna et al. |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,154 B2 | 6/2004 | Fogarty et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,676 B2 | 9/2005 | Buelna |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |

(56) References Cited

U.S. PATENT DOCUMENTS

| | | |
|---|---|---|
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,201 B2 | 1/2007 | Peshkovskiy et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,413,123 B2 | 8/2008 | Ortenzi |
| 7,416,101 B2 | 8/2008 | Shelton, IV et al. |
| 7,416,437 B2 | 8/2008 | Sartor et al. |
| D576,725 S | 9/2008 | Shumer et al. |

(56) References Cited

U.S. PATENT DOCUMENTS

| | | |
|---|---|---|
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,168 B2 | 10/2008 | Novak et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,245 B2 | 1/2010 | Sekino et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,734,476 B2 | 6/2010 | Wildman et al. |
| 7,738,969 B2 | 6/2010 | Bleich |
| 7,740,594 B2 | 6/2010 | Hibner |
| 7,749,240 B2 | 7/2010 | Takahashi et al. |
| 7,749,273 B2 | 7/2010 | Cauthen, III et al. |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,762,979 B2 | 7/2010 | Wuchinich |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |

(56) References Cited

U.S. PATENT DOCUMENTS

| | | |
|---|---|---|
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,020,743 B2 | 9/2011 | Shelton, IV |
| 8,025,630 B2 | 9/2011 | Murakami et al. |
| 8,028,885 B2 | 10/2011 | Smith et al. |
| 8,033,173 B2 | 10/2011 | Ehlert et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,057,467 B2 | 11/2011 | Faller et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,501 B2 | 5/2012 | Houser et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,306 B2 | 7/2012 | Okada et al. |
| 8,221,415 B2 | 7/2012 | Francischelli |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,618 B2 | 8/2012 | Bucciaglia et al. |

(56) References Cited

U.S. PATENT DOCUMENTS

| | | |
|---|---|---|
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,158 B2 | 1/2013 | McKenna et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,115 B2 | 3/2013 | Houser et al. |
| 8,397,971 B2 | 3/2013 | Yates et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,161 B2 | 4/2013 | Nagaya et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,460,326 B2 | 6/2013 | Houser et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| 8,591,536 B2 | 11/2013 | Robertson |

(56) References Cited

U.S. PATENT DOCUMENTS

| | | |
|---|---|---|
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,651,230 B2 | 2/2014 | Peshkovsky et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,663,222 B2 | 3/2014 | Anderson et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,715,306 B2 | 5/2014 | Faller et al. |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,734,476 B2 | 5/2014 | Rhee et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,773,001 B2 | 7/2014 | Wiener et al. |
| 8,777,944 B2 | 7/2014 | Frankhouser et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,709 B2 | 10/2014 | Akagane et al. |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,882,766 B2 | 11/2014 | Couture et al. |
| 8,882,791 B2 | 11/2014 | Stulen |
| 8,882,792 B2 | 11/2014 | Dietz et al. |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,071 B2 | 5/2015 | Miller et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |

(56) References Cited

U.S. PATENT DOCUMENTS

| | | |
|---|---|---|
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,039,705 B2 | 5/2015 | Takashino |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,063,049 B2 | 6/2015 | Beach et al. |
| 9,066,723 B2 | 6/2015 | Beller et al. |
| 9,066,747 B2 | 6/2015 | Robertson |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,084,878 B2 | 7/2015 | Kawaguchi et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,940 B2 | 8/2015 | Twomey |
| 9,114,245 B2 | 8/2015 | Dietz et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,125,722 B2 | 9/2015 | Schwartz |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,055 B2 | 10/2015 | Houser et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,237,923 B2 | 1/2016 | Worrell et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,254,171 B2 | 2/2016 | Trees et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,267 B2 | 6/2016 | Kerr et al. |
| 9,381,058 B2 | 7/2016 | Houser et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,784 B2 | 9/2016 | O'Keeffe |
| 9,445,832 B2 | 9/2016 | Wiener et al. |
| 9,445,833 B2 | 9/2016 | Akagane |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,486,236 B2 | 11/2016 | Price et al. |
| 9,492,187 B2 | 11/2016 | Ravikumar et al. |
| 9,492,224 B2 | 11/2016 | Boudreaux et al. |
| 9,498,245 B2 | 11/2016 | Voegele et al. |
| 9,504,483 B2 | 11/2016 | Houser et al. |

(56) References Cited

U.S. PATENT DOCUMENTS

| | | |
|---|---|---|
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,729 B2 | 4/2017 | Dewaele et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,737,735 B2 | 8/2017 | Dietz et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,839,796 B2 | 12/2017 | Sawada |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,901,339 B2 | 2/2018 | Farascioni |
| 9,901,359 B2 | 2/2018 | Faller et al. |
| 9,907,563 B2 | 3/2018 | Germain et al. |
| 9,913,655 B2 | 3/2018 | Scheib et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,943,325 B2 | 4/2018 | Faller et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,765 B2 | 7/2018 | Hibner et al. |
| 10,028,786 B2 | 7/2018 | Mucilli et al. |
| 10,034,684 B2 | 7/2018 | Weisenburgh, II et al. |
| 10,034,685 B2 | 7/2018 | Boudreaux et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,819 B2 | 8/2018 | Jensen et al. |
| 10,070,916 B2 | 9/2018 | Artale |
| 10,085,762 B2 | 10/2018 | Timm et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,179,022 B2 | 1/2019 | Yates et al. |
| 10,182,837 B2 | 1/2019 | Isola et al. |
| 10,188,385 B2 | 1/2019 | Kerr et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,245,064 B2 | 4/2019 | Rhee et al. |
| 10,245,065 B2 | 4/2019 | Witt et al. |
| 10,245,095 B2 | 4/2019 | Boudreaux |
| 10,251,664 B2 | 4/2019 | Shelton, IV et al. |
| 10,263,171 B2 | 4/2019 | Wiener et al. |
| 10,265,094 B2 | 4/2019 | Witt et al. |
| 10,265,117 B2 | 4/2019 | Wiener et al. |
| 10,265,118 B2 | 4/2019 | Gerhardt |
| D847,990 S | 5/2019 | Kimball |
| 10,278,721 B2 | 5/2019 | Dietz et al. |
| 10,285,723 B2 | 5/2019 | Conlon et al. |
| 10,285,724 B2 | 5/2019 | Faller et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,614 B2 | 7/2019 | Messerly et al. |
| 10,342,602 B2 | 7/2019 | Strobl et al. |
| 10,357,303 B2 | 7/2019 | Conlon et al. |
| 10,368,892 B2 | 8/2019 | Stulen et al. |
| 10,368,957 B2 | 8/2019 | Denzinger et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,580 B2 | 9/2019 | Messerly et al. |
| 10,420,607 B2 | 9/2019 | Woloszko et al. |
| 10,426,507 B2 | 10/2019 | Wiener et al. |
| 10,426,978 B2 | 10/2019 | Akagane |

(56) References Cited

U.S. PATENT DOCUMENTS

| | | |
|---|---|---|
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,463,421 B2 | 11/2019 | Boudreaux et al. |
| 10,463,887 B2 | 11/2019 | Witt et al. |
| 10,470,788 B2 | 11/2019 | Sinelnikov |
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0016603 A1 | 2/2002 | Wells |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052595 A1 | 5/2002 | Witt et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0093113 A1 | 5/2003 | Fogarty et al. |
| 2003/0109875 A1 | 6/2003 | Tetzlaff et al. |
| 2003/0114851 A1 | 6/2003 | Truckai et al. |
| 2003/0114874 A1 | 6/2003 | Craig et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0160698 A1 | 8/2003 | Andreasson et al. |
| 2003/0171747 A1 | 9/2003 | Kanehira et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0121159 A1 | 6/2004 | Cloud et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143759 A1 | 6/2005 | Kelly |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0095046 A1 | 5/2006 | Trieu et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |

(56) References Cited

U.S. PATENT DOCUMENTS

| | | |
|---|---|---|
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0282333 A1 | 12/2007 | Fortson et al. |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043228 A1 | 2/2009 | Northrop et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1 | 3/2009 | Mulvihill et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0312186 A1 | 12/2010 | Suchdev et al. |
| 2010/0331742 A1 | 12/2010 | Masuda |
| 2010/0331872 A1* | 12/2010 | Houser ............... A61N 7/02 606/169 |
| 2010/0331873 A1 | 12/2010 | Dannaher et al. |
| 2011/0004233 A1 | 1/2011 | Muir et al. |
| 2011/0028964 A1 | 2/2011 | Edwards |
| 2011/0106141 A1 | 5/2011 | Nakamura |
| 2011/0125151 A1 | 5/2011 | Strauss et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0143211 A1 | 6/2012 | Kishi |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0090576 A1 | 4/2013 | Stulen et al. |
| 2013/0116717 A1 | 5/2013 | Balek et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0253256 A1 | 9/2013 | Griffith et al. |

(56) References Cited

U.S. PATENT DOCUMENTS

| | | |
|---|---|---|
| 2013/0277410 A1 | 10/2013 | Fernandez et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0081299 A1 | 3/2014 | Dietz et al. |
| 2014/0121569 A1 | 5/2014 | Schafer et al. |
| 2014/0135663 A1 | 5/2014 | Funakubo et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0323926 A1 | 10/2014 | Akagane |
| 2014/0371735 A1 | 12/2014 | Long |
| 2015/0011889 A1 | 1/2015 | Lee |
| 2015/0080876 A1 | 3/2015 | Worrell et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0257780 A1 | 9/2015 | Houser |
| 2015/0272659 A1 | 10/2015 | Boudreaux et al. |
| 2015/0289854 A1 | 10/2015 | Cho et al. |
| 2016/0045248 A1 | 2/2016 | Unger et al. |
| 2016/0051316 A1 | 2/2016 | Boudreaux |
| 2016/0074108 A1 | 3/2016 | Woodruff et al. |
| 2016/0114355 A1 | 4/2016 | Sakai et al. |
| 2016/0121143 A1 | 5/2016 | Mumaw et al. |
| 2016/0128769 A1 | 5/2016 | Rontal et al. |
| 2016/0157927 A1 | 6/2016 | Corbett et al. |
| 2016/0175029 A1 | 6/2016 | Witt et al. |
| 2016/0199125 A1 | 7/2016 | Jones |
| 2016/0206342 A1 | 7/2016 | Robertson et al. |
| 2016/0213395 A1 | 7/2016 | Anim |
| 2016/0262786 A1 | 9/2016 | Madan et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0346001 A1 | 12/2016 | Vakharia et al. |
| 2016/0367281 A1 | 12/2016 | Gee et al. |
| 2016/0374709 A1 | 12/2016 | Timm et al. |
| 2017/0000541 A1 | 1/2017 | Yates et al. |
| 2017/0014152 A1 | 1/2017 | Noui et al. |
| 2017/0056058 A1 | 3/2017 | Voegele et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0105757 A1 | 4/2017 | Weir et al. |
| 2017/0105786 A1 | 4/2017 | Scheib et al. |
| 2017/0105791 A1 | 4/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0189095 A1 | 7/2017 | Danziger et al. |
| 2017/0189096 A1 | 7/2017 | Danziger et al. |
| 2017/0196586 A1 | 7/2017 | Witt et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202592 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2018/0014845 A1 | 1/2018 | Dannaher |
| 2018/0014848 A1 | 1/2018 | Messerly et al. |
| 2018/0049767 A1 | 2/2018 | Gee et al. |
| 2018/0055529 A1 | 3/2018 | Messerly et al. |
| 2018/0055531 A1 | 3/2018 | Messerly et al. |
| 2018/0055533 A1 | 3/2018 | Conlon et al. |
| 2018/0056095 A1 | 3/2018 | Messerly et al. |
| 2018/0078268 A1 | 3/2018 | Messerly et al. |
| 2018/0092660 A1 | 4/2018 | Houser et al. |
| 2018/0125523 A1 | 5/2018 | Johnson |
| 2018/0146975 A1 | 5/2018 | Zhang |
| 2018/0168680 A1 | 6/2018 | Houser et al. |
| 2018/0177521 A1 | 6/2018 | Faller et al. |
| 2018/0199957 A1 | 7/2018 | Robertson et al. |
| 2018/0206881 A1 | 7/2018 | Price et al. |
| 2018/0221049 A1 | 8/2018 | Faller et al. |
| 2019/0008543 A1 | 1/2019 | Scoggins et al. |
| 2019/0053822 A1 | 2/2019 | Robertson et al. |
| 2019/0090900 A1 | 3/2019 | Rhee et al. |
| 2019/0133633 A1 | 5/2019 | Neurohr et al. |
| 2019/0239919 A1 | 8/2019 | Witt et al. |
| 2019/0262029 A1 | 8/2019 | Messerly et al. |

FOREIGN PATENT DOCUMENTS

| | | |
|---|---|---|
| CN | 2460047 Y | 11/2001 |
| CN | 1634601 A | 7/2005 |
| CN | 1775323 A | 5/2006 |
| CN | 1922563 A | 2/2007 |
| CN | 2868227 Y | 2/2007 |
| CN | 202027624 U | 11/2011 |
| CN | 102335778 A | 2/2012 |
| CN | 103668171 A | 3/2014 |
| CN | 103921215 A | 7/2014 |
| DE | 2065681 A1 | 3/1975 |
| DE | 3904558 A1 | 8/1990 |
| DE | 9210327 U1 | 11/1992 |
| DE | 4300307 A1 | 7/1994 |
| DE | 4434938 C1 | 2/1996 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2510891 B1 | 6/2016 |
| FR | 2964554 A1 | 3/2012 |
| GB | 2032221 A | 4/1980 |
| GB | 2317566 A | 4/1998 |

(56) References Cited

FOREIGN PATENT DOCUMENTS

| | | |
|---|---|---|
| GB | 2318298 A | 4/1998 |
| GB | 2425480 A | 11/2006 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H0595955 A | 4/1993 |
| JP | H05115490 A | 5/1993 |
| JP | H0647048 A | 2/1994 |
| JP | H0670938 A | 3/1994 |
| JP | H06104503 A | 4/1994 |
| JP | H0824266 A | 1/1996 |
| JP | H08229050 A | 9/1996 |
| JP | H08275950 A | 10/1996 |
| JP | H08275951 A | 10/1996 |
| JP | H08299351 A | 11/1996 |
| JP | H08336545 A | 12/1996 |
| JP | H09135553 A | 5/1997 |
| JP | H09140722 A | 6/1997 |
| JP | H105236 A | 1/1998 |
| JP | H105237 A | 1/1998 |
| JP | H10295700 A | 11/1998 |
| JP | H11128238 A | 5/1999 |
| JP | 2000139943 A | 5/2000 |
| JP | 2000210299 A | 8/2000 |
| JP | 2000271145 A | 10/2000 |
| JP | 2000287987 A | 10/2000 |
| JP | 2000312682 A | 11/2000 |
| JP | 2001029353 A | 2/2001 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2004209043 A | 7/2004 |
| JP | 2005027026 A | 1/2005 |
| JP | 2005074088 A | 3/2005 |
| JP | 2005094552 A | 4/2005 |
| JP | 2005253674 A | 9/2005 |
| JP | 2006217716 A | 8/2006 |
| JP | 2006288431 A | 10/2006 |
| JP | D1339835 S | 8/2008 |
| JP | 2009297352 A | 12/2009 |
| JP | 2010009686 A | 1/2010 |
| JP | 2010121865 A | 6/2010 |
| JP | 2011160586 A | 8/2011 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9816157 A1 | 4/1998 |
| WO | WO-9920213 A1 | 4/1999 |
| WO | WO-9923960 A1 | 5/1999 |
| WO | WO-0024322 A1 | 5/2000 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0195810 A2 | 12/2001 |
| WO | WO-02080799 A1 | 10/2002 |
| WO | WO-2004037095 A2 | 5/2004 |
| WO | WO-2004078051 A2 | 9/2004 |
| WO | WO-2004098426 A1 | 11/2004 |
| WO | WO-2005084250 A2 | 9/2005 |
| WO | WO-2007008710 A2 | 1/2007 |
| WO | WO-2008118709 A1 | 10/2008 |
| WO | WO-2008130793 A1 | 10/2008 |
| WO | WO-2010104755 A1 | 9/2010 |
| WO | WO-2011008672 A2 | 1/2011 |
| WO | WO-2011052939 A2 | 5/2011 |
| WO | WO-2011060031 A1 | 5/2011 |
| WO | WO-2012044606 A2 | 4/2012 |
| WO | WO-2012066983 A1 | 5/2012 |
| WO | WO-2013048963 A2 | 4/2013 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Incropera et al., Fundamentals of Heat and Mass Transfer, Wiley, New York (1990). (Book—not attached).

F. A. Duck, "Optical Properties of Tissue Including Ultraviolet and Infrared Radiation," pp. 43-71 in Physical Properties of Tissue (1990).

Campbell et al, "Thermal Imaging in Surgery," p. 19-3, in Medical Infrared Imaging, N. A. Diakides and J. D. Bronzino, Eds. (2008).

AST Products, Inc., "Principles of Video Contact Angle Analysis," 20 pages, (2006).

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Graff, K.F., "Elastic Wave Propagation in a Curved Sonic Transmission Line," IEEE Transactions on Sonics and Ultrasonics, SU-17(1), 1-6 (1970).

Makarov, S. N., Ochmann, M., Desinger, K., "The longitudinal vibration response of a curved fiber used for laser ultrasound surgical therapy," Journal of the Acoustical Society of America 102, 1191-1199 (1997).

Morley, L. S. D., "Elastic Waves in a Naturally Curved Rod," Quarterly Journal of Mechanics and Applied Mathematics, 14: 155-172 (1961).

(56) References Cited

OTHER PUBLICATIONS

Walsh, S. J., White, R. G., "Vibrational Power Transmission in Curved Beams," Journal of Sound and Vibration, 233(3), 455-488 (2000).
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
http://www.apicalinstr.com/generators.htm.
http://www.dotmed.com/listing/electrosurical-unit/ethicon/ultracision-g110-/1466724.
http:/www.ethicon.com/gb-en/healthcare-professionals/products/energy-devices/capital//ge . . . .
http://www.medicalexpo.com/medical-manufacturer/electrosurgical-generator-6951.html.
http://www.megadyne.com/es_generator.php.
http://www.valleylab.com/product/es/generators/index.html.
Sullivan, "Optimal Choice for Number of Strands in a Litz-Wire Transformer Winding," IEEE Transactions on Power Electronics, vol. 14, No. 2, Mar. 1999, pp. 283-291.
Covidien 501(k) Summary Sonicision, dated Feb. 24, 2011 (7 pages).
http://www.4-traders.com/JOHNSON-JOHNSON-4832/news/Johnson-Johnson-Ethicon-E . . . .
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, *Engineering Formulas* § Z.7 (7th ed. 1997).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Douglas, S.C. "Introduction to Adaptive Filter". Digital Signal Processing Handbook. Ed. Vijay K. Madisetti and Douglas B. Williams. Boca Raton: CRC Press LLC, 1999.
Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak—Sharpe,Integrated Circuit Engineering, Addison-Wesley Publishing, Reading, MA (1979). (book—not attached).
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Sadiq Muhammad et al: "High-performance planar ultrasonic tool based on d31-mode piezocrystal", IEEE Transactions on Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.
Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news_events/article20030224.html.

* cited by examiner

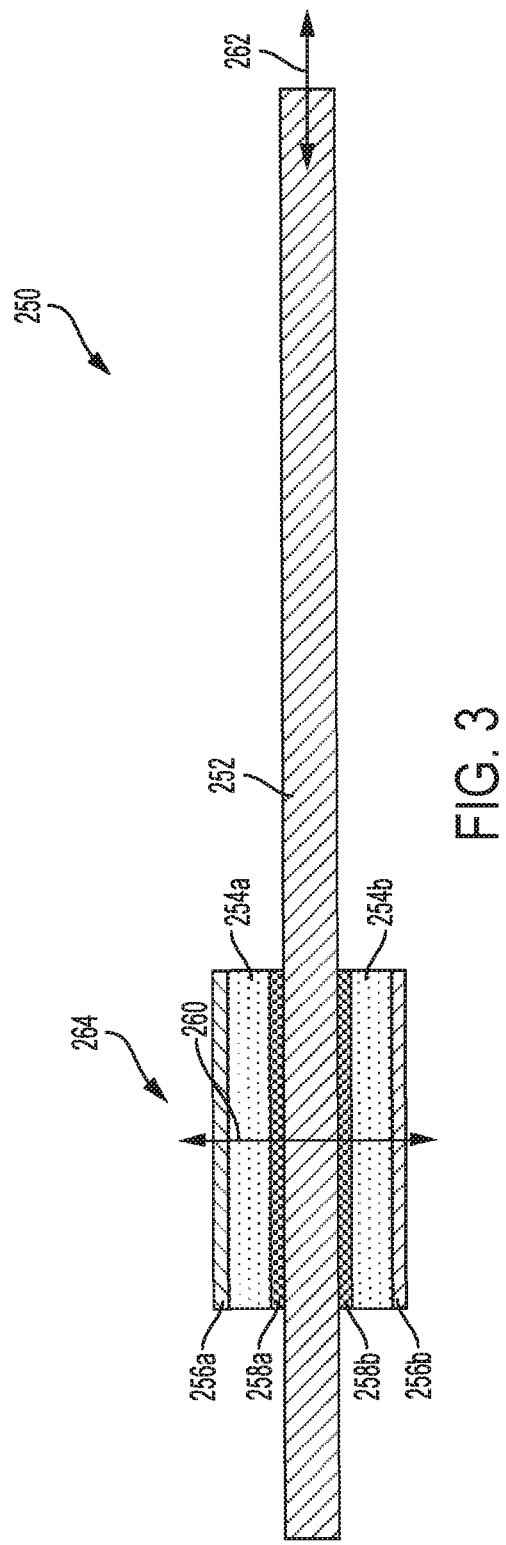

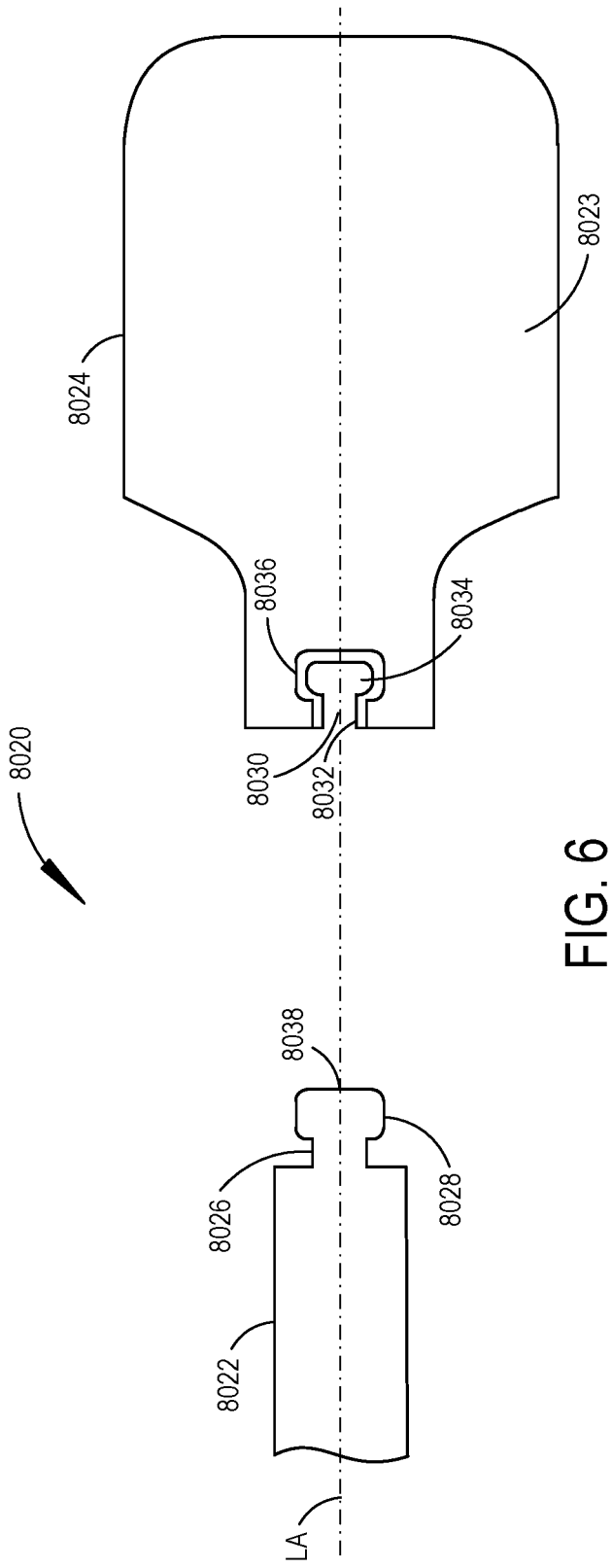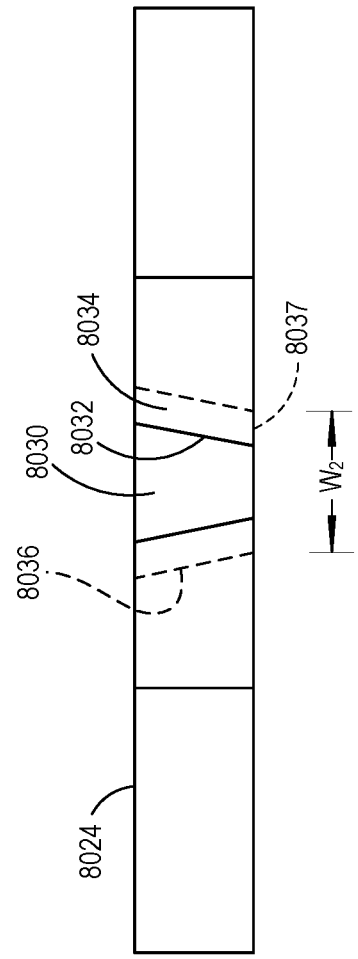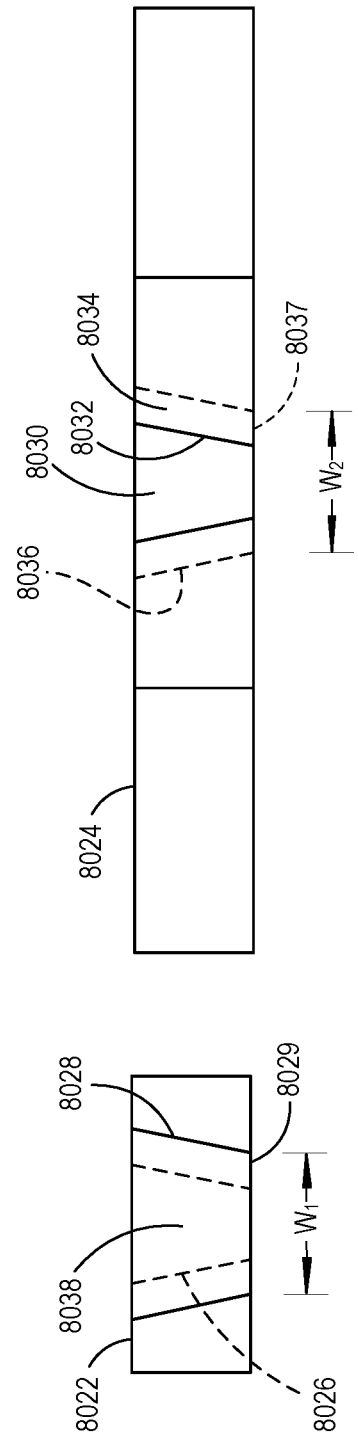

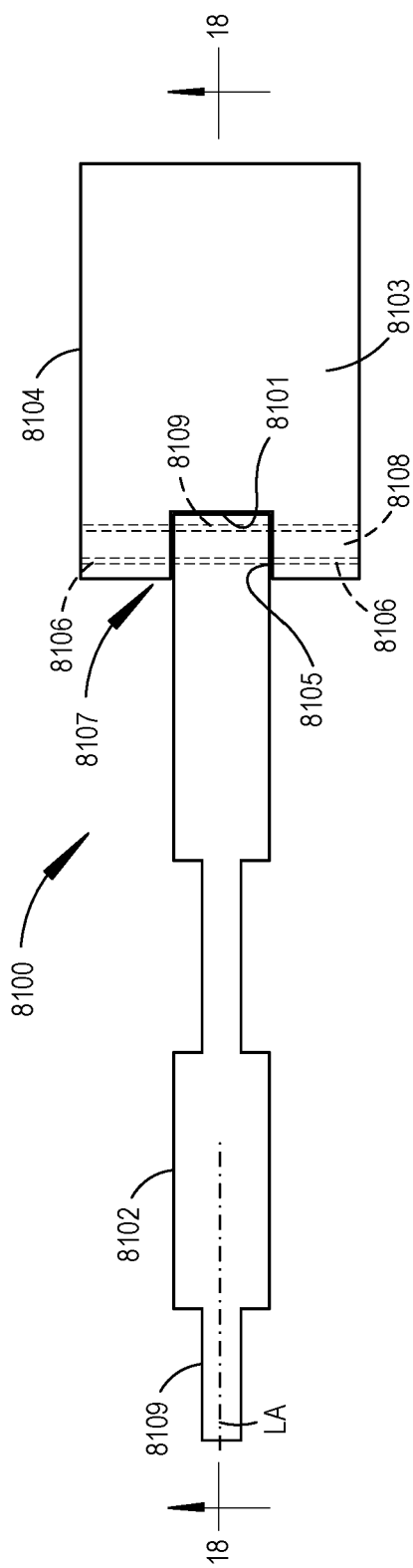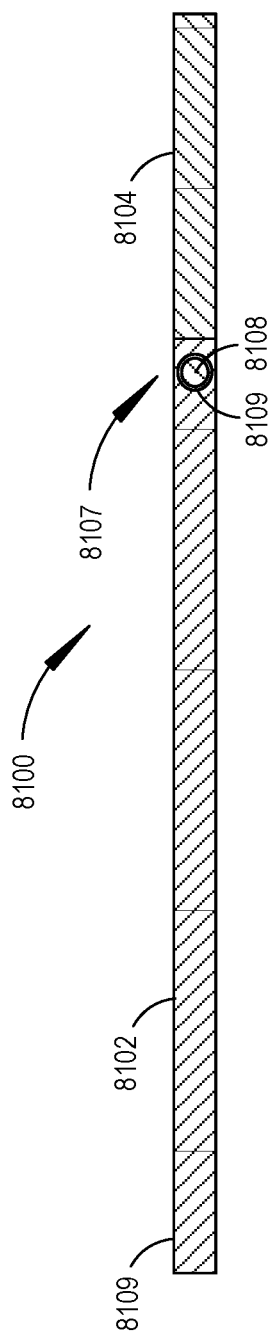
FIG. 17
FIG. 18

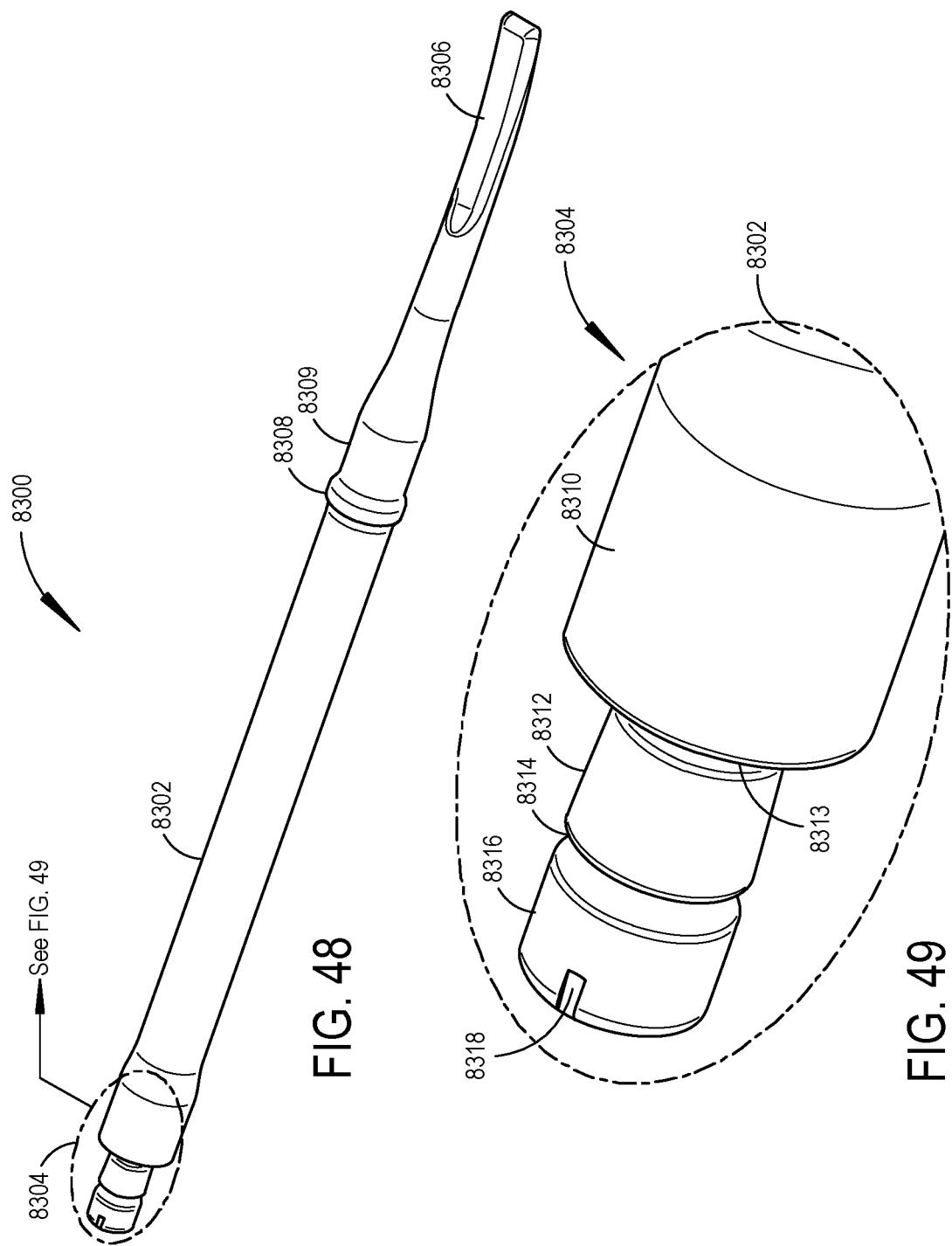

ULTRASONIC TRANSDUCER TO WAVEGUIDE JOINING

PRIORITY

This application claims the benefit of U.S. Provisional Application Ser. No. 62/379,550 filed Aug. 25, 2016, which is incorporated herein by reference in its entirety.

BACKGROUND

The present disclosure relates, in general, to ultrasonic surgical instruments and more particularly to ultrasonic transducers to drive ultrasonic waveguides. Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate or cauterize tissue or to separate muscle tissue from bone. Ultrasonic instruments utilizing solid core technology are particularly advantageous because of the amount of ultrasonic energy that may be transmitted from the ultrasonic transducer, through a waveguide, and to the surgical end effector. Such instruments may be used for open procedures or minimally invasive procedures, such as endoscopic or laparoscopic procedures, wherein the end effector is passed through a trocar to reach the surgical site.

Activating or exciting the end effector (e.g., cutting blade) of such instruments at ultrasonic frequencies induces longitudinal vibratory movement that generates localized heat within adjacent tissue. Because of the nature of ultrasonic instruments, a particular ultrasonically actuated end effector may be designed to perform numerous functions, including, for example, cutting and coagulation. Ultrasonic vibration is induced in the surgical end effector by electrically exciting a transducer, for example. The transducer may be constructed of one or more piezoelectric or magnetostrictive elements in the instrument hand piece. Vibrations generated by the transducer are transmitted to the surgical end effector via an ultrasonic waveguide extending from the transducer to the surgical end effector. The waveguide and end effector are designed to resonate at the same frequency as the transducer. Therefore, when an end effector is attached to a transducer, the overall system frequency is the same frequency as the transducer itself.

The amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals $2\pi$ times the cyclic frequency, f; and
A=the zero-to-peak amplitude.

The longitudinal excursion of the end effector tip is defined as the peak-to-peak (p-t-p) amplitude, which is just twice the amplitude of the sine wave or 2A. Often, the end effector can comprise a blade which, owing to the longitudinal excursion, can cut and/or coagulate tissue. U.S. Pat. No. 6,283,981, which issued on Sep. 4, 2001 and is entitled METHOD OF BALANCING ASYMMETRIC ULTRASONIC SURGICAL BLADES; U.S. Pat. No. 6,309,400, which issued on Oct. 30, 2001 and is entitled CURVED ULTRASONIC WAVEGUIDE HAVING A TRAPEZOIDAL CROSS SECTION; and U.S. Pat. No. 6,436,115, which issued on Aug. 20, 2002 and is entitled BALANCED ULTRASONIC WAVEGUIDE INCLUDING A PLURALITY OF BALANCE ASYMMETRIES, the entire disclosures of which are hereby incorporated by reference herein, disclose various ultrasonic surgical instruments.

SUMMARY

In one general aspect, an ultrasonic surgical instrument is provided. The ultrasonic instrument comprises a waveguide comprising a distal end configured as a blade and a proximal end configured to couple to a transducer base plate; and the transducer base plate comprising a distal end coupled to the proximal end of the waveguide to define a joint at an interface between the waveguide and the transducer base plate, the transducer base plate comprising a first and second sides defining corresponding first and second flat faces, wherein the first flat face is configured to receive a first piezoelectric element and the second flat face is configured to receive a second piezoelectric element, wherein the first and second piezoelectric elements are configured to operate in a D31 mode.

In another aspect, an ultrasonic waveguide comprises a shaft comprising a proximal end and a distal end, wherein the proximal end is configured to couple to an ultrasonic transducer and the distal end defines cylindrical aperture with a flat perpendicular bottom configured to receive a proximal end of a blade; and a blade attached to the shaft, the blade comprising a distal end for treating tissue and a proximal end defining a conical male end defining a flat perpendicular bottom, wherein the conical male end defines a proximal diameter and a distal diameter, wherein the proximal diameter is larger than the distal diameter, and wherein the conical male end is received into the cylindrical aperture defined by the distal end of the shaft.

In another aspect, an ultrasonic surgical instrument comprises an ultrasonic waveguide defining a T-shaped male connector at a proximal end; and a symmetric two-piece clamshell housing comprising: first and second T-shaped pockets configured to receive the T-shaped male connector, wherein the T-shaped pockets are press fit to the T-shaped male connector; and first and second recessed pockets configured to support first and a second piezoelectric elements, wherein the first and second piezoelectric elements are configured to operate in a D31 mode.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 3 illustrates a D31 ultrasonic transducer architecture that includes an ultrasonic waveguide and one or more piezoelectric elements fixed to the ultrasonic waveguide, according to one aspect of the present disclosure.

FIG. 6 is a side view of an ultrasonic surgical instrument configured in a D31 transducer architecture comprising separate ultrasonic waveguide and ultrasonic transducer base plate components shown in a decoupled configuration, according to one aspect of this disclosure.

FIG. 7 is an end view of the waveguide shown in FIG. 6, according to one aspect of this disclosure.

FIG. 8 is an end view of the transducer base plate shown in FIG. 6, according to one aspect of this disclosure.

FIG. 10A is a section view taken prior to joining the waveguide to the transducer base plate and FIG. 10B is a section view taken after partially joining the waveguide to the transducer base plate.

FIG. 17 is a side view of an ultrasonic surgical instrument configured in a D31 transducer architecture comprising separate ultrasonic waveguide and ultrasonic transducer base plate components shown in a coupled configuration, according to one aspect of this disclosure.

FIG. 18 is a section view of the ultrasonic surgical instrument along section line 18-18 shown in FIG. 17, according to one aspect of this disclosure.

FIG. 48 is a perspective view of an ultrasonic waveguide for an ultrasonic surgical instrument comprising an ultrasonic waveguide shaft made of one metal and coupled to an ultrasonic blade made of a dissimilar metal, according to one aspect of this disclosure.

FIG. 49 is a magnified view of the coupler, according to one aspect of this disclosure.

FIG. 52 is a section view of the waveguide shaft and the ultrasonic blade shown in FIG. 51 in a decoupled configuration, according to one aspect of this disclosure.

FIG. 53 is a section view of a pre-assembly of the waveguide shaft and the ultrasonic blade shown in FIG. 52 in a coupled configuration prior to applying the swaging process, according to one aspect of this disclosure.

FIG. 54 is a section view of the waveguide shaft and the ultrasonic blade shown in FIG. 53 in a coupled after the application of the swaging process, according to one aspect of this disclosure.

FIG. 55 is a section view of joined ultrasonic waveguide showing the waveguide shaft coupled to the ultrasonic blade shown in FIG. 51, according to one aspect of this disclosure.

DESCRIPTION

Figure 1:
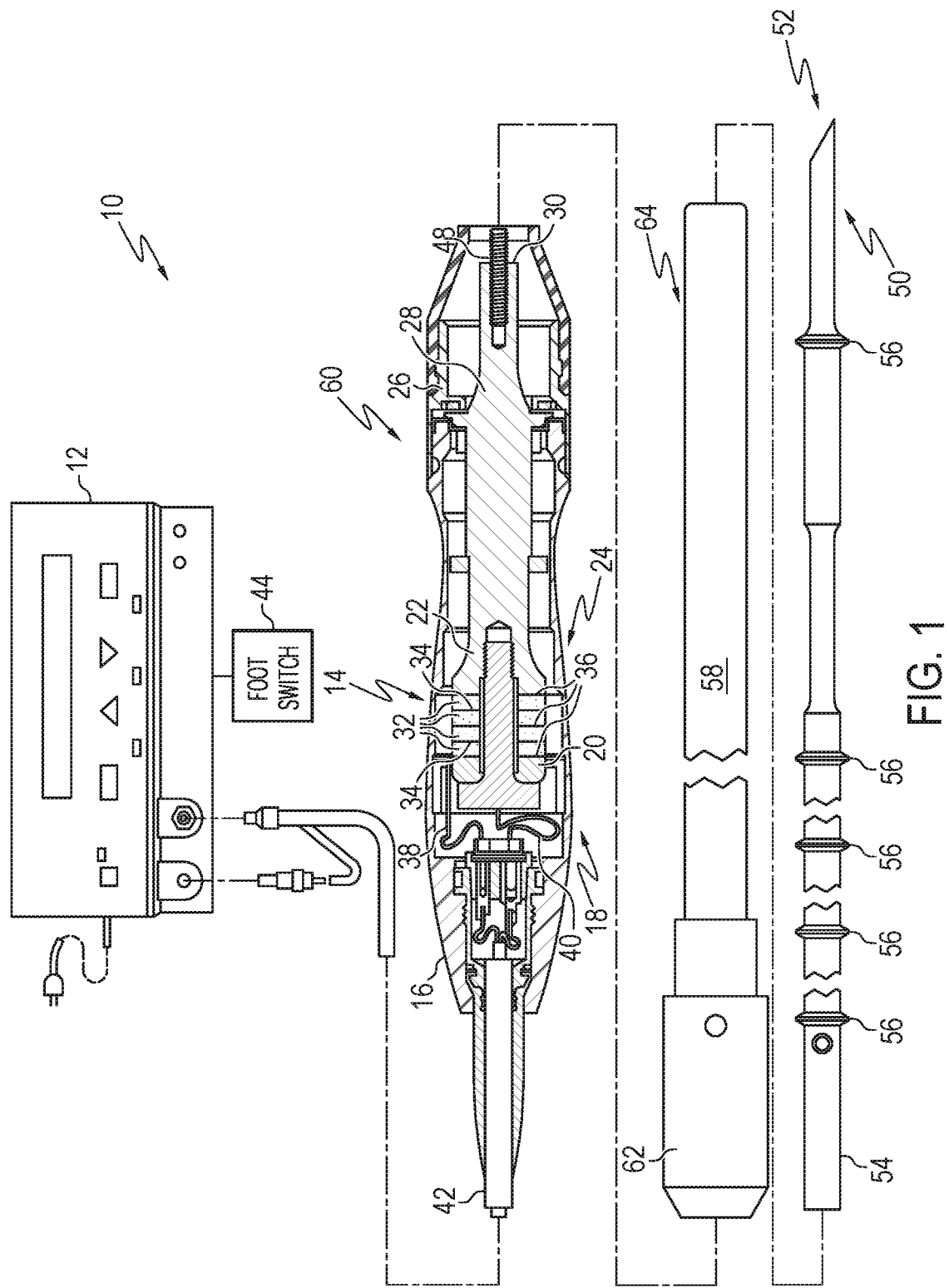
FIG. 1 illustrates an ultrasonic surgical instrument system, according to one aspect of this disclosure.

Applicant of the present application owns the following patent applications filed Aug. 17, 2017 and which are each herein incorporated by reference in their respective entireties:

U.S. patent application Ser. No. 15/679,940, entitled Ultrasonic Transducer Techniques for Ultrasonic Surgical Instrument, by inventors Jeffrey Messerly et al., now U.S. Patent Application Publication No. 2018/0055529.

U.S. patent application Ser. No. 15/679,948, entitled "Ultrasonic Transducer For Surgical Instrument, by inventors Jeffrey Messerly et al., now U.S. Pat. No. 10,420,580.

U.S. patent application Ser. No. 15/679,952, entitled "Electrical And Thermal Connections For Ultrasonic Transducer" by inventors Jeffrey Messerly et al., now U.S. Patent Application Publication No. 2018/0055531.

U.S. patent application Ser. No. 15/679,959, entitled "Ultrasonic Transducer to Waveguide Acoustic Coupling, Connections, and Configurations" by inventors Jeffrey Messerly et al., now U.S. Patent Application Publication No. 2018/0056095.

U.S. patent application Ser. No. 15/679,967, entitled "Tissue Loading of a Surgical Instrument" by inventors Jeffrey Messerly et al., now U.S. Patent Application Publication No. 2018/0078268.

Before explaining various aspects in detail, it should be noted that such aspects are not limited in their application or use to the details of construction and arrangement of parts illustrated in the accompanying drawings and description. The illustrative aspects may be implemented or incorporated in other aspects, variations and modifications, and may be practiced or carried out in various ways. For example, the surgical instruments disclosed below are illustrative only and not meant to limit the scope or application thereof. Furthermore, unless otherwise indicated, the terms and expressions employed herein have been chosen for the purpose of describing the illustrative aspects for the convenience of the reader and are not to limit the scope thereof.

Certain aspects will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting examples aspects and that the scope of the various aspects is defined solely by the claims. The features illustrated or described in connection with one aspect may be combined with the features of other aspects. Such modifications and variations are intended to be included within the scope of the claims.

Various aspects described herein relate, in general, to ultrasonic surgical instruments and blades for use therewith. Examples of ultrasonic surgical instruments and blades are disclosed in U.S. Pat. Nos. 5,322,055; 5,954,736; 6,309,400; 6,278,218; 6,283,981; 6,325,811; and 8,319,400, wherein the entire disclosures of which are incorporated by reference herein.

According to various aspects, an ultrasonic instrument comprising a surgical tool having an end effector such as a blade can be of particular benefit, among others, in orthopedic procedures where it is desirable to remove cortical bone and/or tissue while controlling bleeding. Due to its cutting and coagulation characteristics, a blade of an ultrasonic surgical instrument may be useful for general soft tissue cutting and coagulation. In certain circumstances, a blade according to various aspects may be useful to simultaneously cut and hemostatically seal or cauterize tissue. A blade may be straight or curved, and useful for either open or laparoscopic applications. A blade according to various aspects may be useful in spine surgery, especially to assist in posterior access in removing muscle from bone.

FIG. 1 illustrates one aspect of an ultrasonic system 10. One aspect of the ultrasonic system 10 comprises an ultrasonic signal generator 12 coupled to an ultrasonic transducer 14, a hand piece assembly 60 comprising a hand piece housing 16, and an end effector 50. The ultrasonic transducer 14, which is known as a "Langevin stack", generally includes a transduction portion 18, a first resonator or end-bell 20, and a second resonator or fore-bell 22, and ancillary components. In various aspects, the ultrasonic transducer 14 is preferably an integral number of one-half system wavelengths ($n\lambda/2$) in length as will be described in more detail below. An acoustic assembly 24 can include the ultrasonic transducer 14, a mount 26, a velocity transformer 28, and a surface 30.

It will be appreciated that the terms "proximal" and "distal" are used herein with reference to a clinician gripping the hand piece assembly 60. Thus, the end effector 50 is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude of the velocity transformer 28, or, alternately, fore-bell 22 may have no amplification.

Referring again to FIG. 1, end-bell 20 can include a threaded member extending therefrom which can be configured to be threadably engaged with a threaded aperture in fore-bell 22. In various aspects, piezoelectric elements, such as piezoelectric elements 32, for example, can be compressed between end-bell 20 and fore-bell 22 when end-bell 20 and fore-bell 22 are assembled together. Piezoelectric elements 32 may be fabricated from any suitable material, such as, for example, lead zirconate-titanate, lead metaniobate, lead titanate, and/or any suitable piezoelectric crystal material, for example.

In various aspects, as discussed in greater detail below, transducer 14 can further comprise electrodes, such as positive electrodes 34 and negative electrodes 36, for example, which can be configured to create a voltage potential across one or more piezoelectric elements 32. Each of the positive electrodes 34, negative electrodes 36, and the piezoelectric elements 32 can comprise a bore extending through the center which can be configured to receive the threaded member of end-bell 20. In various aspects, the positive and negative electrodes 34 and 36 are electrically coupled to wires 38 and 40, respectively, wherein the wires 38 and 40 can be encased within a cable 42 and electrically connectable to the ultrasonic signal generator 12 of the ultrasonic system 10.

In various aspects, the ultrasonic transducer 14 of the acoustic assembly 24 converts the electrical signal from the ultrasonic signal generator 12 into mechanical energy that results in primarily longitudinal vibratory motion of the ultrasonic transducer 24 and the end effector 50 at ultrasonic frequencies. A suitable generator is available as model number GEN01, from Ethicon Endo-Surgery, Inc., Cincinnati, Ohio. When the acoustic assembly 24 is energized, a vibratory motion standing wave is generated through the acoustic assembly 24. A suitable vibrational frequency range may be about 20 Hz to 120 kHz and a well-suited vibrational frequency range may be about 30-70 kHz and one example operational vibrational frequency may be approximately 55.5 kHz.

The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node (i.e., where motion is usually maximal). The distance between an anti-node and its nearest node is one-quarter wavelength ($\lambda/4$).

As outlined above, the wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to a foot switch 44, for example, to produce an acoustic standing wave in the acoustic assembly 24. The electrical signal causes disturbances in the piezoelectric elements 32 in the form of repeated small displacements resulting in large compression forces within the material. The repeated small displacements cause the piezoelectric elements 32 to expand and contract in a continuous manner along the axis of the voltage gradient, producing longitudinal waves of ultrasonic energy.

In various aspects, the ultrasonic energy produced by transducer 14 can be transmitted through the acoustic assembly 24 to the end effector 50 via an ultrasonic transmission waveguide 46. In order for the acoustic assembly 24 to deliver energy to the end effector 50, the components of the acoustic assembly 24 are acoustically coupled to the end effector 50. For example, the distal end of the ultrasonic transducer 14 may be acoustically coupled at the surface 30 to the proximal end of the ultrasonic transmission waveguide 46 by a threaded connection such as a stud 48.

The components of the acoustic assembly 24 can be acoustically tuned such that the length of any assembly is an integral number of one-half wavelengths ($n\lambda/2$), where the wavelength $\Lambda$ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

The ultrasonic end effector 50 may have a length substantially equal to an integral multiple of one-half system wavelengths ($\lambda/2$). A distal end 52 of the ultrasonic end effector 50 may be disposed at, or at least near, an antinode in order to provide the maximum, or at least nearly maximum, longitudinal excursion of the distal end. When the transducer assembly is energized, in various aspects, the distal end 52 of the ultrasonic end effector 50 may be configured to move in the range of, for example, approximately 10 to 500 microns peak-to-peak and preferably in the range of approximately 30 to 150 microns at a predetermined vibrational frequency.

As outlined above, the ultrasonic end effector 50 may be coupled to the ultrasonic transmission waveguide 46. In various aspects, the ultrasonic end effector 50 and the ultrasonic transmission guide 46 as illustrated are formed as a single unit construction from a material suitable for transmission of ultrasonic energy such as, for example, Ti6Al4V (an alloy of titanium including aluminum and vanadium), aluminum, stainless steel, and/or any other suitable material. Alternately, the ultrasonic end effector 50 may be separable (and of differing composition) from the ultrasonic transmission waveguide 46, and coupled by, for example, a stud, weld, glue, quick connect, or other suitable known methods. The ultrasonic transmission waveguide 46 may have a length substantially equal to an integral number of one-half system wavelengths ($\lambda/2$), for example. The ultrasonic transmission waveguide 46 may be preferably fabricated from a solid core shaft constructed out of material that propagates ultrasonic energy efficiently, such as titanium alloy (i.e., Ti6Al4V) or an aluminum alloy, for example.

In the aspect illustrated in FIG. 1, the ultrasonic transmission waveguide 46 comprises a plurality of stabilizing silicone rings or compliant supports 56 positioned at, or at least near, a plurality of nodes. The silicone rings 56 can dampen undesirable vibration and isolate the ultrasonic energy from a sheath 58 at least partially surrounding waveguide 46, thereby assuring the flow of ultrasonic energy in a longitudinal direction to the distal end 52 of the end effector 50 with maximum efficiency.

As shown in FIG. 1, the sheath 58 can be coupled to the distal end of the handpiece assembly 60. The sheath 58 generally includes an adapter or nose cone 62 and an elongated tubular member 64. The tubular member 64 is attached to and/or extends from the adapter 62 and has an opening extending longitudinally therethrough. In various aspects, the sheath 58 may be threaded or snapped onto the distal end of the housing 16. In at least one aspect, the ultrasonic transmission waveguide 46 extends through the opening of the tubular member 64 and the silicone rings 56 can contact the sidewalls of the opening and isolate the ultrasonic transmission waveguide 46 therein. In various aspects, the adapter 62 of the sheath 58 is preferably constructed from Ultem®, for example, and the tubular member 64 is fabricated from stainless steel, for example. In at least one aspect, the ultrasonic transmission waveguide 46 may have polymeric material, for example, surrounding it in order to isolate it from outside contact.

As described above, a voltage, or power source can be operably coupled with one or more of the piezoelectric elements of a transducer, wherein a voltage potential applied to each of the piezoelectric elements can cause the piezoelectric elements to expand and contract, or vibrate, in a longitudinal direction. As also described above, the voltage potential can be cyclical and, in various aspects, the voltage potential can be cycled at a frequency which is the same as, or nearly the same as, the resonant frequency of the system of components comprising transducer 14, wave guide 46, and end effector 50, for example. In various aspects, however, certain of the piezoelectric elements within the transducer may contribute more to the standing wave of longitudinal vibrations than other piezoelectric elements within the transducer. More particularly, a longitudinal strain profile may develop within a transducer wherein the strain profile may control, or limit, the longitudinal displacements that some of the piezoelectric elements can contribute to the standing wave of vibrations, especially when the system is being vibrated at or near its resonant frequency.

It may be recognized, in reference to the ultrasonic surgical instrument system 10 of FIG. 1, that multiple components may be required to couple the mechanical vibrations from the piezoelectric elements 32 through the wave guide 46 to the end effector 50. The additional elements comprising the acoustic assembly 24 may add additional manufacturing costs, fabrication steps, and complexity to the system. Disclosed below are aspects of an ultrasonic medical device that may require fewer components, manufacturing steps, and costs than the equivalent device illustrated in FIG. 1 and as disclosed above.

Again, referring to FIG. 1, the piezoelectric elements 32 are configured into a "Langevin" stack, in which the piezoelectric elements 32 and their activating electrodes 34 and 36 (together, transducer 14) are interleaved. The mechanical vibrations of the activated piezoelectric elements 32 propagate along the longitudinal axis of the transducer 14, and are coupled via the acoustic assembly 24 to the end of the waveguide 46. Such a mode of operation of a piezoelectric element is frequently described as the D33 mode of the element, especially for ceramic piezoelectric elements comprising, for example, lead zirconate-titanate, lead metaniobate, or lead titanate. The D33 mode of a ceramic piezoelectric element is illustrated in FIGS. 2A-2C.

Figure 2A:
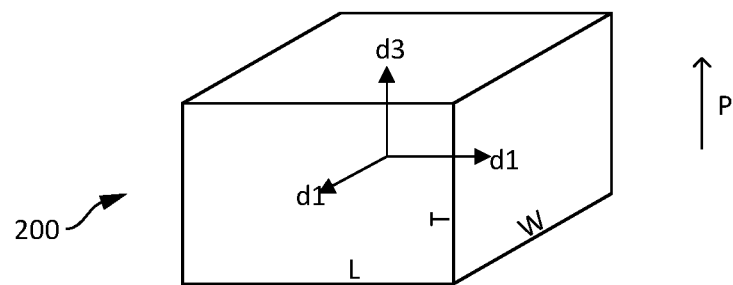
FIGS. 2A-2C illustrate a piezoelectric transducer, according to one aspect of this disclosure.

FIG. 2A depicts a piezoelectric element 200 fabricated from a ceramic piezoelectric material. A piezoelectric ceramic material is a polycrystalline material comprising a plurality of individual microcrystalline domains. Each microcrystalline domain possesses a polarization axis along which the domain may expand or contract in response to an imposed electric field. However, in a native ceramic, the polarization axes of the microcrystalline domains are arranged randomly, so there is no net piezoelectric effect in the bulk ceramic. A net re-orientation of the polarization axes may be induced by subjecting the ceramic to a temperature above the Curie temperature of the material and placing the material in a strong electrical field. Once the temperature of the sample is dropped below the Curie temperature, a majority of the individual polarization axes will be re-oriented and fixed in a bulk polarization direction. FIG. 2A illustrates such a piezoelectric element 200 after being polarized along the inducing electric field axis P. While the un-polarized piezoelectric element 200 lacks any net piezoelectric axis, the polarized element 200 can be described as possessing a polarization axis, d3, parallel to the inducing field axis P direction. For completeness, an axis orthogonal to the d3 axis may be termed a d1 axis. The dimensions of the piezoelectric element 200 are labeled as length (L), width (W), and thickness (T).

Figure 2B:
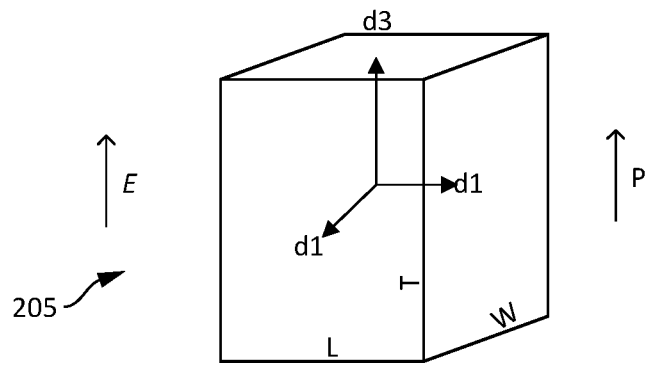
Figure 2C:
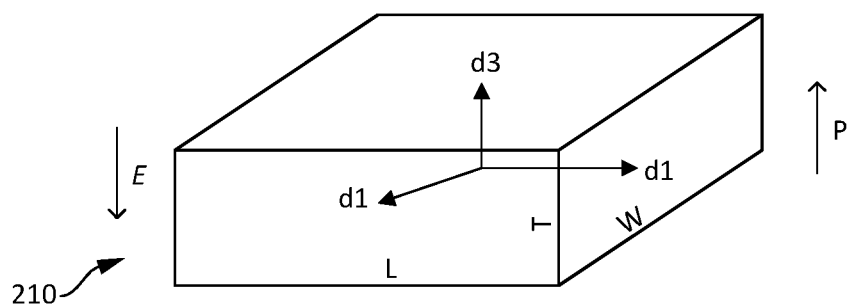

FIGS. 2B and 2C illustrate the mechanical deformations of a piezoelectric element 200 that may be induced by subjecting the piezoelectric element 200 to an actuating electrical field E oriented along the d3 (or P) axis. FIG. 2B illustrates the effect of an electric field E having the same direction as the polarization field P along the d3 axis on a piezoelectric element 205. As illustrated in FIG. 2B, the piezoelectric element 205 may deform by expanding along the d3 axis while compressing along the d1 axis. FIG. 2C illustrates the effect of an electric field E having the opposing direction to the polarization field P along the d3 axis on a piezoelectric element 210. As illustrated in FIG. 2C, the piezoelectric element 210 may deform by compressing along the d3 axis, while expanding along the d1 axis. Vibrational coupling along the d3 axis during the application of an electric field along the d3 axis may be termed D33 coupling or activation using a D33 mode of a piezoelectric element. The transducer 14 illustrated in FIG. 1 uses the D33 mode of the piezoelectric elements 32 for transmitting mechanical vibrations along the wave guide 46 to the end effector 50. Because the piezoelectric element also deforms along the d1 axis, vibrational coupling along the d1 axis during the application of an electric field along the d3 axis may also be an effective source of mechanical vibrations. Such coupling may be termed D31 coupling or activation using a D31 mode of a piezoelectric element.

As illustrated by FIGS. 2A-2C, during operation in the D31 mode, transverse expansion of piezoelectric elements 200, 205, 210 may be mathematically modeled by the following equation:

$$\frac{\Delta L}{L} = \frac{\Delta W}{W} = \frac{V_{d31}}{T}$$

In the equation, L, W, and T refer to the length, width and thickness dimensions of a piezoelectric element, respectively. $V_{d31}$ denotes the voltage applied to a piezoelectric element operating in the D31 mode. The quantity of transverse expansion resulting from the D31 coupling described above is represented by $\Delta L$ (i.e. expansion of the piezoelectric element along the length dimension) and $\Delta W$ (i.e. expansion of the piezoelectric element along the width dimension). Additionally, the transverse expansion equation models the relationship between $\Delta L$ and $\Delta W$ and the applied voltage $V_{d31}$. Disclosed below are aspects of ultrasonic medical devices based on D31 activation by a piezoelectric element.

In various aspects, as described below, a ultrasonic medical device can comprise a transducer configured to produce longitudinal vibrations, and a surgical tool having a transducer base mounting portion operably coupled to the transducer, an end effector, and wave guide therebetween. In certain aspects, as also described below, the transducer can produce vibrations which can be transmitted to the end effector, wherein the vibrations can drive the transducer base mounting portion, the wave guide, the end effector, and/or the other various components of the ultrasonic medical device at, or near, a resonant frequency. In resonance, a longitudinal strain pattern, or longitudinal stress pattern, can develop within the transducer, the wave guide, and/or the end effector, for example. In various aspects, such a longitudinal strain pattern, or longitudinal stress pattern, can cause the longitudinal strain, or longitudinal stress, to vary along the length of the transducer base plate (e.g., a transducer mounting portion), wave guide, and/or end effector, in a sinusoidal, or at least substantially sinusoidal, manner. In at least one aspect, for example, the longitudinal strain pattern can have maximum peaks and zero points, wherein the strain values can vary in a non-linear manner between such peaks and zero points.

FIG. 3 illustrates an ultrasonic surgical instrument 250 that includes an ultrasonic waveguide 252 attached to an ultrasonic transducer 264 by a bonding material, where the ultrasonic surgical instrument 250 is configured to operate in a D31 mode, according to one aspect of the present disclosure. The ultrasonic transducer 264 includes first and second piezoelectric elements 254a, 254b attached to the ultrasonic waveguide 252 by a bonding material. The piezoelectric elements 254a, 254b include electrically conductive plates 256a, 256b to electrically couple one pole of a voltage source suitable to drive the piezoelectric elements 254a, 254b (e.g., usually a high voltage). The opposite pole of the voltage source is electrically coupled to the ultrasonic waveguide 252 by electrically conductive joints 258a, 258b. In one aspect, the electrically conductive plates 256a, 256b are coupled to a positive pole of the voltage source and the electrically conductive joints 258a, 258b are electrically coupled to ground potential through the metal ultrasonic waveguide 252. In one aspect, the ultrasonic waveguide 252 is made of titanium, titanium alloy, aluminum, or aluminum alloy (i.e., Ti6Al4V) and the piezoelectric elements 254a, 254b are made of a lead zirconate titanate intermetallic inorganic compound with the chemical formula Pb[Zr$_x$Ti$_{1-x}$]O$_3$ (0≤x≤1). Also called PZT, it is a ceramic perovskite material that shows a marked piezoelectric effect, meaning that the compound changes shape when an electric field is applied. It is used in a number of practical applications such as ultrasonic transducers and piezoelectric resonators PZT. The poling axis (P) of the piezoelectric elements 254a, 254b is indicated by the direction arrow 260. The motion axis of the ultrasonic waveguide 252 in response to excitation of the piezoelectric elements 254a, 245b is shown by a motion arrow 262 at the distal end of the ultrasonic waveguide 252 generally referred to as the ultrasonic blade portion of the ultrasonic waveguide 252. The motion axis 262 is orthogonal to the poling axis (P) 260.

In conventional D33 ultrasonic transducer architectures as shown in FIG. 1, the bolted piezoelectric elements 32 utilize electrodes 34, 36 to create electrical contact to both sizes of each piezoelectric element 34. The D31 architecture 250 according to one aspect of the present disclosure, however, employs a different technique to create electrical contact to both sides of each piezoelectric element 254a, 254b. Various techniques for providing electrical contact to the piezoelectric elements 254a, 254b include bonding electrical conductive elements (e.g., wires) to the free surface of each piezoelectric element 254a, 254b for the high potential connection and bonding each piezoelectric element 254a, 254b the to the ultrasonic waveguide 252 for the ground connection using solder, conductive epoxy, or other techniques described herein. Compression can be used to maintain electrical contact to the acoustic train without making a permanent connection. This can cause an increase in device thickness and should be controlled to avoid damaging the piezoelectric elements 254a, 254b. Low compression can damage the piezoelectric element 254a, 254b by a spark gap and high compression can damage the piezoelectric elements 254a, 254b by local mechanical wear. In other techniques, metallic spring contacts may be employed to create electrical contact with the piezoelectric elements 254a, 254b. Other techniques may include foil-over-foam gaskets, conductive foam, solder. Electrical connections are provided to both sides of the piezoelectric elements 254a, 254b in the D31 acoustic train configuration. The electrical ground connection can be made to the metal ultrasonic waveguide 252, which is electrically conductive, if there is electrical contact between the piezoelectric elements 254a, 254b and the ultrasonic waveguide 252.

In various aspects, as described below, an ultrasonic medical device may comprise a transducer configured to produce longitudinal vibrations, and a surgical instrument having a transducer base plate operably coupled to the transducer, an end effector, and wave guide therebetween. In certain aspects, as also described below, the transducer can produce vibrations which can be transmitted to the end effector, wherein the vibrations can drive the transducer base plate, the wave guide, the end effector, and/or the other various components of the ultrasonic medical device at, or near, a resonant frequency. In resonance, a longitudinal strain pattern, or longitudinal stress pattern, can develop within the transducer, the wave guide, and/or the end effector, for example. In various aspects, such a longitudinal strain pattern, or longitudinal stress pattern, can cause the longitudinal strain, or longitudinal stress, to vary along the length of the transducer base plate, wave guide, and/or end effector, in a sinusoidal, or at least substantially sinusoidal, manner. In at least one aspect, for example, the longitudinal strain pattern can have maximum peaks and zero points, wherein the strain values can vary in a non-linear manner between such peaks and zero points.

In conventional D33 ultrasonic transducer architectures as shown in FIG. 1, a bolt provides compression that acoustically couples the piezoelectric elements rings to the ultrasonic waveguide. The D31 architecture 250 according to one aspect of the present disclosure employs a variety of different techniques to acoustically couple the piezoelectric elements 254a, 254b to the ultrasonic waveguide 252. These techniques are disclosed hereinbelow.

Figure 4:
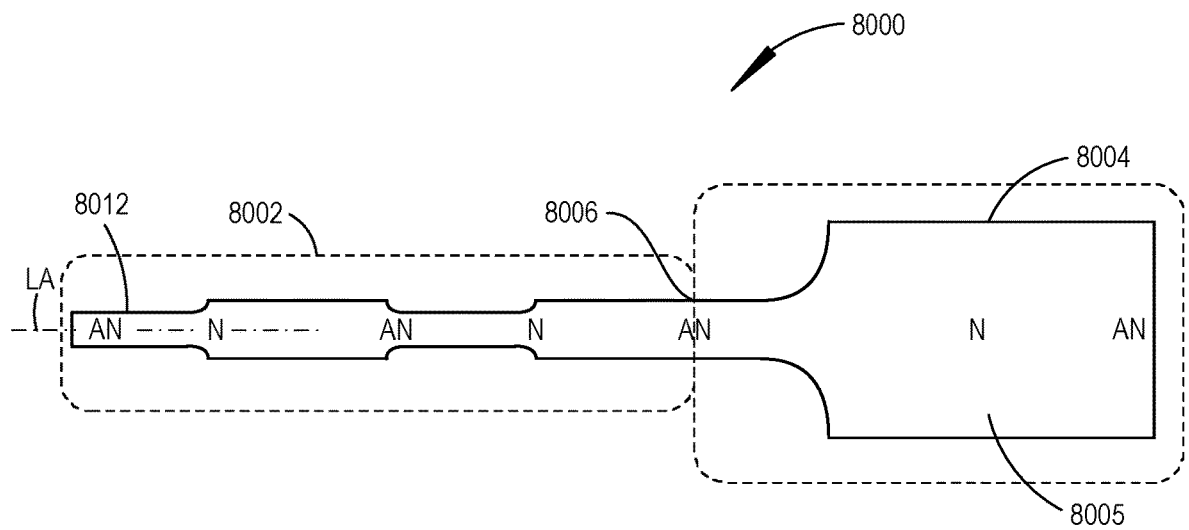
FIG. 4 is a side view of an ultrasonic surgical instrument configured in a D31 ultrasonic transducer architecture comprising separate ultrasonic waveguide and ultrasonic transducer base plate components shown in a coupled configuration, according to one aspect of this disclosure.

FIG. 4 is a side view of an ultrasonic surgical instrument 8000 configured in a D31 ultrasonic transducer architecture comprising separate ultrasonic waveguide 8002 and ultrasonic transducer base plate 8004 (e.g., a transducer mounting portion) components shown in a coupled configuration, according to one aspect of this disclosure. The ultrasonic surgical instrument 8000 may comprise multiple pieces to reduce material waste and provide the ability to use alternate materials and/or manufacturing methods for the waveguide 8002 and the transducer base plate 8004. In one aspect, the waveguide 8002 and the transducer base plate 8004 are made separately from flat metal stock suitable for transmitting ultrasonic vibrations such as titanium, titanium alloy, aluminum, or aluminum alloy, for example, as described herein. For example, the waveguide 8002 and the transducer base plate 8004 are two separate pieces and can be made of the same material or different materials suitable for transmitting ultrasonic energy along the longitudinal axis LA.

Figures 5A, 5B:
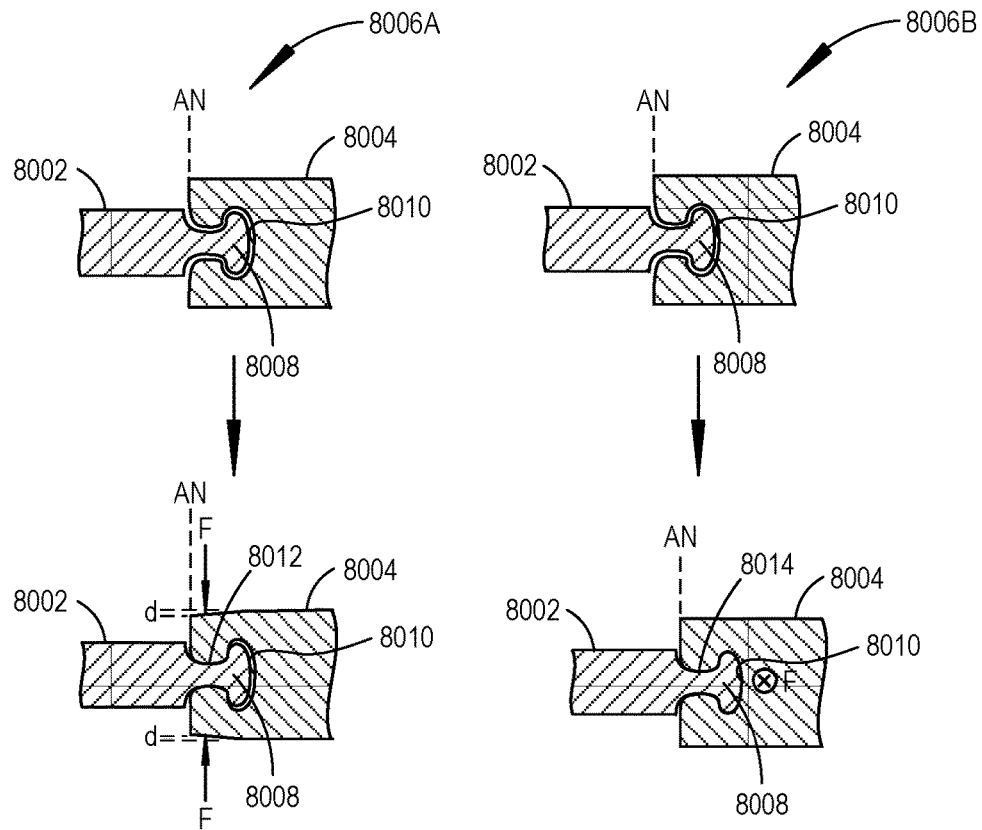
FIG. 5A is a section view of a jigsaw puzzle joint of the waveguide and transducer base plate components of the ultrasonic surgical instrument, according to one aspect of this disclosure.
FIG. 5B is a section view of a jigsaw puzzle joint of the waveguide and transducer base plate components of the ultrasonic surgical instrument, according to one aspect of this disclosure.

The ultrasonic waveguide 8002 and ultrasonic transducer base plate 8004 each define mutually complementary mating geometries and are connected by a jigsaw puzzle joint 8006. A proximal end of the waveguide 8002 includes a connection portion to attach to the transducer base plate 8004. An example of a connection portion is shown in FIGS. 5A and 5B. A distal end of the waveguide 8002 includes an ultrasonic blade 8012. The blade 8012 is used to treat tissue. The transducer base plate 8004 defines flat faces 8005 on opposite sides of the transducer base plate 8004 suitable to attach and support a PZT piezoelectric element on each flat face 8005 similar to the D31 configuration shown by way of example in FIG. 3. The distal end of the transducer base plate 8004 includes a connection portion that is complementary to the connection portion located on the proximal end of the waveguide 8002. The connection portion of the waveguide 8002 may be male, female, or flat and the connection portion of the transducer base plate 8004 may be female, male, or flat, respectively. When fully assembled, the ultrasonic instrument 8000 is configured to transmit ultrasonic energy to the distal end of the waveguide 8002 along the longitudinal axis LA.

In one aspect, the separate waveguide 8002 and transducer base plate 8004 components are coupled at the jigsaw puzzle joint 8006 by plastic deformation of one or both components to enable acoustic transmission along an ultrasonic train. In one aspect, the waveguide 8002 and transducer base plate 8004 components of the ultrasonic instrument 8000 may be coupled to form the jigsaw puzzle joint 8006. Plastic deformation of one or both of the waveguide 8002 and transducer base plate 8004 components can be used to fasten the waveguide 8002 and transducer base plate 8004 components to enable transmission of ultrasonic energy along a longitudinal axis LA of the ultrasonic instrument 8000.

The waveguide 8002 component of the ultrasonic instrument 8000 is acoustically coupled between the transducer base plate 8004 and an ultrasonic blade 8012, or end effector, at the distal end of the waveguide 8002. The transducer base plate 8004 is located at a proximal end of the ultrasonic instrument 8000 and is sized and configured to mount ultrasonic transducer elements, such as, for example, PZT piezoelectric elements, on opposite faces 8005 of the transducer base plate 8004. The ultrasonic blade 8012 is located at a distal end of the ultrasonic instrument 8000. In the surgical instrument 8000 illustrated in FIG. 4, the nodes (N), i.e., where motion is usually minimal, and antinodes (AN), where motion is usually maximal, are indicated along the longitudinal length of the ultrasonic instrument 8000. The distance between an anti-node (AN) and its nearest node (N) is one-quarter wavelength ($\lambda/4$). An AN is located at a distal end of the blade 8012.

FIG. 5A is a section view of a jigsaw puzzle joint 8006A of the waveguide 8002 and transducer base plate 8004 components of the ultrasonic surgical instrument 8000, according to one aspect of this disclosure. A proximal end of the waveguide 8002 component defines a male jigsaw puzzle piece 8008 sized and configured to be received within a complementary mating female jigsaw puzzle piece 8010 defined by a distal end of the transducer base plate 8004 component. To make the jigsaw puzzle joint 8006A, first the male jigsaw puzzle piece 8008 is fitted into the female jigsaw puzzle piece 8010 to achieve a clearance fit. A permanent joint 8012 is created by applying opposing forces F to the distal end of the second component 8004 to plastically deform the second component 8004 by an amount indicated as "d." In other aspects, the proximal end of the waveguide 8002 defines a female connection portion and the distal end of the transducer base plate 8004 defines a male connection portion.

FIG. 5B is a section view of a jigsaw puzzle joint 8006B of the waveguide 8002 and transducer base plate 8004 components of the ultrasonic surgical instrument 8000, according to one aspect of this disclosure. The male jigsaw puzzle piece 8008 of the waveguide 8002 is sized and configured to be received within the female jigsaw puzzle piece 8010 defined at a distal portion of the transducer base plate 8004 to form an interference fit at the joint 8014. The interference fit, also known as a press fit or friction fit, is fastening between two components in which the inner waveguide 8002 component is larger than the outer transducer base plate 8004 component. To achieve the interference fit, a force F is applied during assembly. After the waveguide 8002 component is larger than the outer transducer base plate 8004 component are joined, the mating surfaces will feel pressure due to friction, and deformation of the completed assembly will be observed. In other aspects, the proximal end of the waveguide 8002 defines a female connection portion and the distal end of the transducer base plate 8004 defines a male connection portion.

FIG. 6 is a side view of an ultrasonic surgical instrument 8020 configured in a D31 transducer architecture comprising separate ultrasonic waveguide 8022 and ultrasonic transducer base plate 8024 (e.g., a transducer mounting portion) components shown in a decoupled configuration, according to one aspect of this disclosure. FIG. 7 is an end view of the waveguide 8022 shown in FIG. 6, according to one aspect of this disclosure. FIG. 8 is an end view of the transducer base plate 8024 shown in FIG. 6, according to one aspect of this disclosure. The ultrasonic surgical instrument 8020 may comprise multiple pieces to reduce material waste and provide the ability to use alternate materials and/or manufacturing methods for the waveguide 8022 and the transducer base plate 8024. In one aspect, the waveguide 8022 and the transducer base plate 8024 are made separately from flat metal stock suitable for transmitting ultrasonic vibrations such as titanium, titanium alloy, aluminum, or aluminum alloy, for example, as described herein. For example, the waveguide 8022 and the transducer base plate 8024 are two separate pieces and can be made of the same material or different materials suitable for transmitting ultrasonic energy along the longitudinal axis LA. The transducer base plate 8024 defines flat faces 8023 on opposite sides of the transducer base plate 8024 suitable to attach and support a PZT piezoelectric element on each flat face 8023 similar to the D31 configuration shown by way of example in FIG. 3. When the waveguide 8022 and transducer base plate 8024 are coupled in a D31 configuration, ultrasonic vibrations generated by the PZT piezoelectric elements are transmitted along the waveguide 8022 to an ultrasonic blade at a distal end of the waveguide 8022. When fully assembled, the ultrasonic instrument 8020 is configured to transmit ultrasonic energy to the distal end of the waveguide 8022 along the longitudinal axis LA.

With reference to FIGS. 6-8, the waveguide 8022 and the transducer base plate 8024 are made separately from flat metal stock suitable for transmitting ultrasonic vibrations such as titanium, titanium alloy, aluminum, or aluminum alloy, for example. The waveguide 8022 and the transducer base plate 8024 define a taper through a thickness dimension and are connected by a tapered joint 8039. A proximal end of the waveguide 8022 defines a male connection portion 8028 sized and configured to be received within a complementary mating female connection portion 8032. The male connection portion 8028 defines a tapered neck 8026 and a tapered end 8038, both tapered through the thickness of the male connection portion 8028. The female connection portion 8032 defines a first aperture 8030 to receive the neck portion 8026 of the waveguide 8022 and defines a second aperture 8034 to receive the tapered end 8038 of the waveguide 8022. The complementary mating female connection portion 8032 defines a tapered inner wall 8036 that acts as a lead-in when pressing the waveguide 8022 and the transducer base plate 8024 components together. The waveguide 8022 is coupled to the transducer base plate 8024 to enable transmission of ultrasonic energy along a longitudinal axis LA of the ultrasonic instrument 8020. The width $W_1$ of the bottom portion 8029 of the male connection portion 8028 is wider than the width $W_2$ of the bottom opening 8037 defined by the tapered wall 8036 of defined by the second aperture 8034 to form an interference fit when the waveguide 8022 is press fit into the transducer base plate 8024. The tapered wall 8036 through the thickness of the transducer base plate 8024 may be formed by waterjet or angled laser beam.

Figure 9:
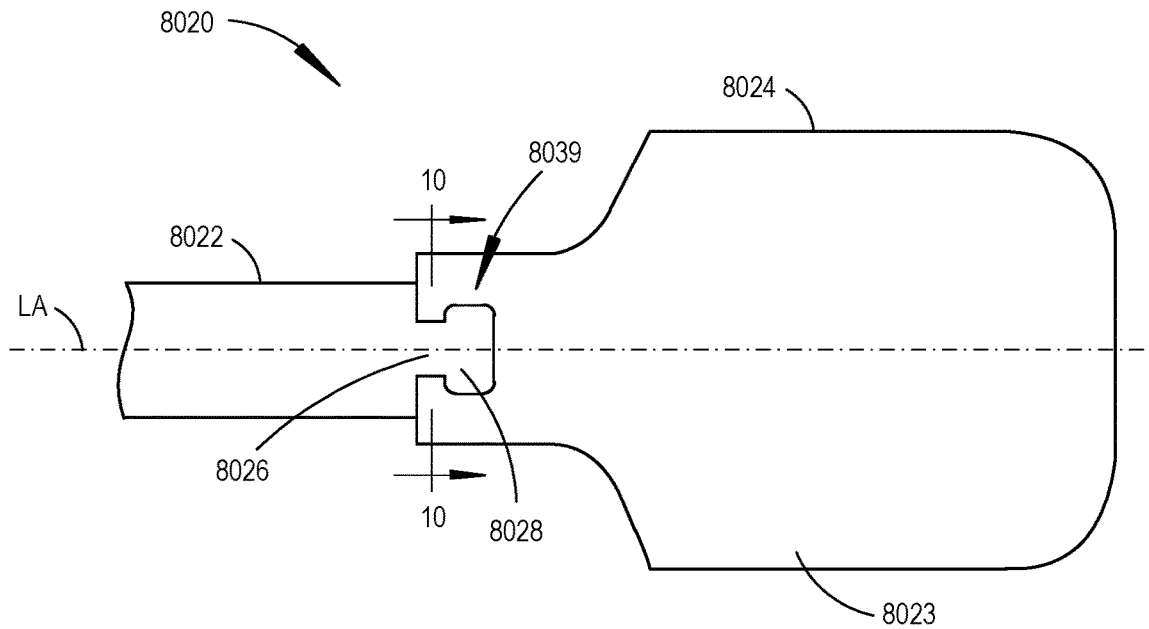
FIG. 9 is a side view of the ultrasonic instrument shown in FIG. 6 in a coupled configuration connected at the tapered joint, according to one aspect of this disclosure.
Figures 10A, 10B:
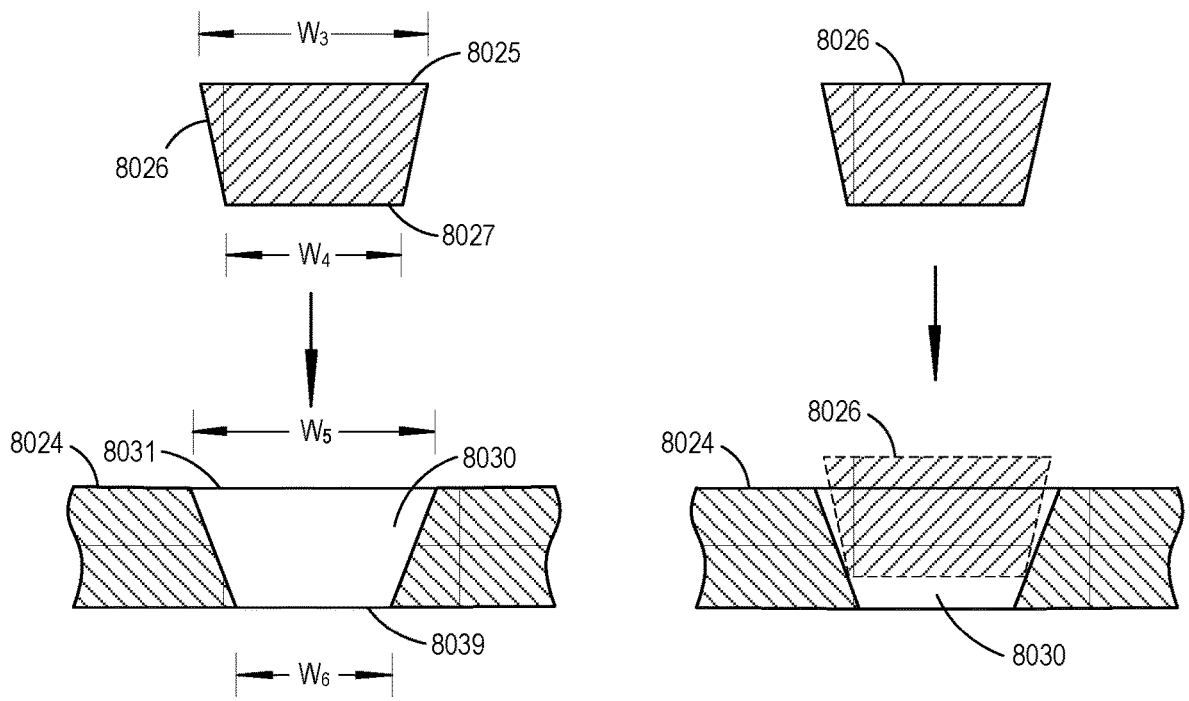
FIGS. 10A and 10B are section views taken along section line 10-10 shown in FIG. 9, where

FIG. 9 is a side view of the ultrasonic instrument 8020 shown in FIG. 6 in a coupled configuration connected at the tapered joint 8039, according to one aspect of this disclosure. The waveguide 8024 and the transducer base plate 8024 are made separately from flat metal stock suitable for transmitting ultrasonic vibrations such as titanium, titanium alloy, aluminum, or aluminum alloy, for example, as described herein. As shown in FIG. 9, the waveguide 8022 is coupled to the transducer base plate 8024 through a taper through a thickness dimension such that the tapered joint 8039 forms an interference fit. FIGS. 10A and 10B are section views taken along section line 10-10 shown in FIG. 9. FIG. 10A is a section view taken prior to joining the waveguide 8022 to the transducer base plate 8024 and FIG. 10B is a section view taken after partially joining the waveguide 8022 to the transducer base plate 8024.

With reference now to FIGS. 10A and 10B, the neck portion 8026 of the waveguide 8022 is sized and configured to fit in a complementary mating female connection portion 8030. The male connection portion 8028 is sized and configured to form an interference fit when press fit into the complementary mating female connection portion 8032. For example, the top 8025 of the of the neck portion 8026 has a width $W_3$ and the bottom 8027 has a width $W_4$, where $W_4$ is less than $W_3$ to define a taper. The top opening 8031 of the female connection portion 8030 has a width $W_5$ and the bottom opening 8033 has width $W_6$, where $W_6$ is less than $W_5$ to define a complementary taper to receive the neck portion 8026. The taper acts as a lead-in when the waveguide 8022 is press fit with the transducer base plate 8024. The taper results in a more predictable or controlled material flow when press fitting the waveguide 8022 into the transducer base plate 8024. In one aspect, the bottom of the neck portion $W_4$ is wider than the width $W_6$ of the bottom opening 8033 of the complementary mating female connection portion 8030 to form an interference fit as shown in FIG. 10B. The widths $W_3$ and $W_5$ may be the same or, in one aspect, the width $W_3$ may be greater than the width $W_5$. Although not shown, the tapered end 8038 to achieve an interference fit with the complementary second aperture 8034 that defines a tapered inner wall 8036.

Figure 11:
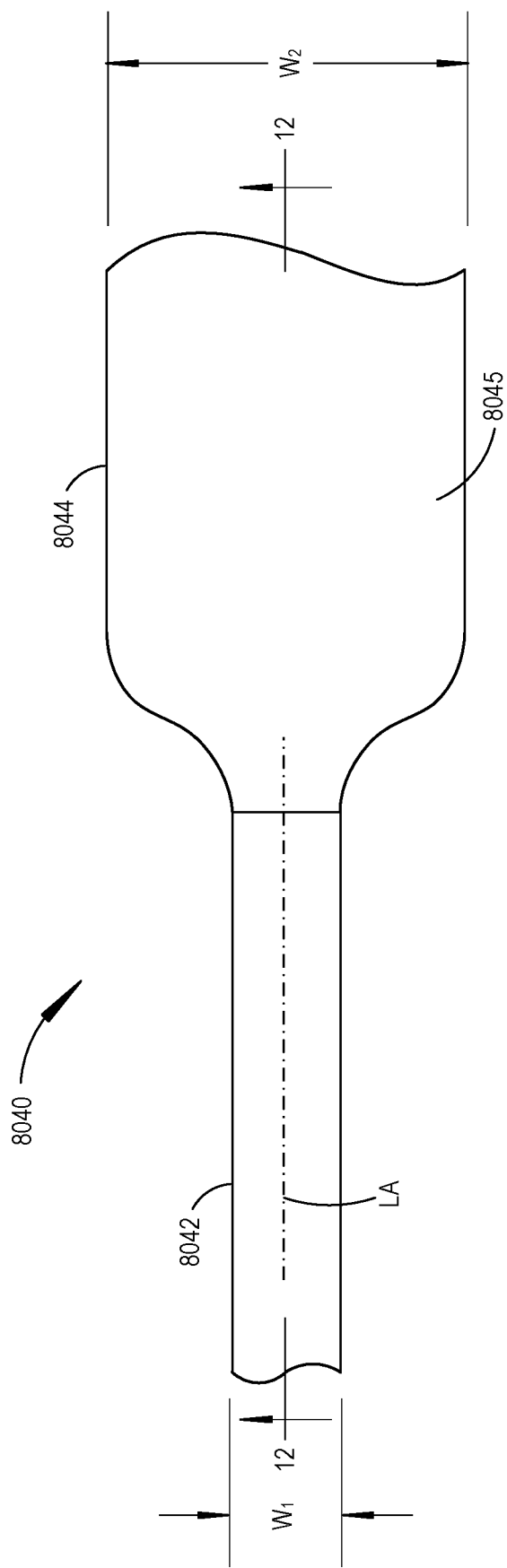
FIG. 11 is a side view of an ultrasonic surgical instrument configured in a D31 transducer architecture comprising separate ultrasonic waveguide and ultrasonic transducer base plate components shown in a coupled configuration, according to one aspect of this disclosure.

FIG. 11 is a side view of an ultrasonic surgical instrument 8040 configured in a D31 transducer architecture comprising separate ultrasonic waveguide 8042 and ultrasonic transducer base plate 8044 (e.g., a transducer mounting portion) components shown in a coupled configuration, according to one aspect of this disclosure. The ultrasonic surgical instrument 8040 may comprise multiple pieces to reduce material waste and provide the ability to use alternate materials and/or manufacturing methods for the waveguide 8042 and the transducer base plate 8044. In one aspect, the waveguide 8042 and the transducer base plate 8044 are made separately from flat metal stock suitable for transmitting ultrasonic vibrations such as titanium, titanium alloy, aluminum, or aluminum alloy, for example, as described herein. For example, the waveguide 8042 and the transducer base plate 8044 are two separate pieces. The waveguide 8042 is configured to transmit ultrasonic energy along a longitudinal axis. The transducer base plate 8044 component is sized and configured to support PZT piezoelectric elements on opposite sides of the transducer base plate 8044. The waveguide 8042 is made of a metal suitable for transmitting ultrasonic vibrations. Generally, the waveguide 8042 may be made of a first metal material such as titanium, titanium alloy, aluminum, or aluminum alloy as described herein. In other aspects, the waveguide 8042 and the transducer base plate 8144 maybe made of the same material. In either case, the material should be suitable for transmitting ultrasonic energy along the longitudinal axis LA.

A proximal end of the waveguide 8042 includes a connection portion to attach to the transducer base plate 8044. A distal end of the waveguide 8042 includes an ultrasonic blade to treat tissue. The transducer base plate 8044 defines flat faces 8045 on opposite sides of the transducer base plate 8044 suitable to attach and support a PZT piezoelectric element on each flat face 8045 similar to the D31 configuration shown by way of example in FIG. 3. The distal end of the transducer base plate 8044 includes a connection portion that is complementary to the connection portion located on the proximal end of the waveguide 8002. The connection portion of the waveguide 8042 may be male, female, or flat and the connection portion of the transducer base plate 8044 may be female, male, or flat, respectively.

The transducer base plate 8044 is made of a second metal material such as aluminum that is different from the first metal material that the waveguide 8042 is made from. When fully assembled, the ultrasonic instrument 8040 is configured to transmit ultrasonic energy to the distal end of the waveguide 8042 along the longitudinal axis LA.

When the waveguide 8042 and transducer base plate 8044 components are coupled in a D31 configuration, ultrasonic vibrations generated by the PZT piezoelectric elements are transmitted along the waveguide 8042 to an ultrasonic blade located at a distal end of the waveguide 8042. Accordingly, ultrasonic energy is transmitted along the longitudinal axis of the waveguide 8042. As shown in FIG. 11, the waveguide 8042 has a width $W_1$ and the transducer base plate 8044 has width $W_2$, where $W_2$ is greater than $W_1$. The waveguide 8042 may be coupled to the transducer base plate 8044 using any of the techniques described herein. The waveguide 8042 and transducer base plate 8044 may be coupled using any of the techniques described herein, including, without limitation, a jigsaw puzzle joint, a C-shaped pin joint, a pin joint, a press fit joint, an interference joint, parallel tang joint, a screw joint, an interference flange joint, an interference pin joint, a wedge joint, a luer lock joint, a swaged joint, among other joints described herein.

Figure 12:
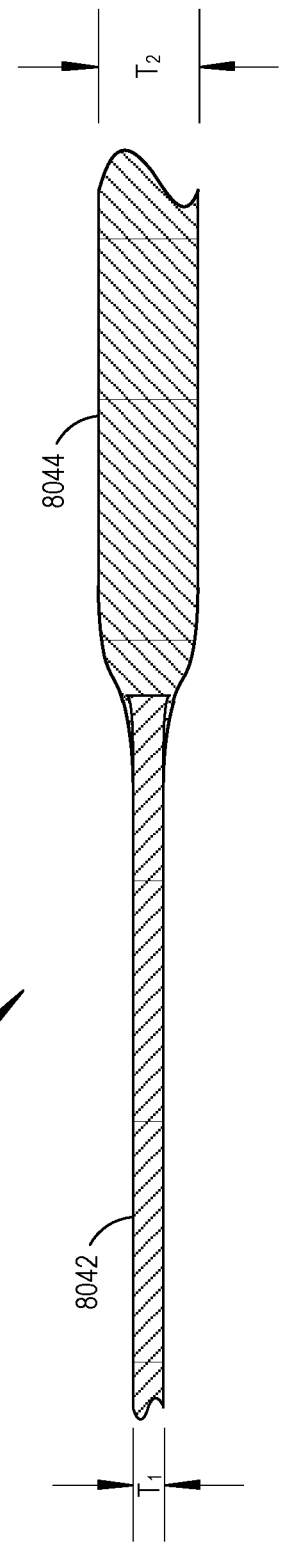
FIG. 12 is a section view of the ultrasonic surgical instrument shown in FIG. 11 taken along section line 12-12 shown in FIG. 11, according to one aspect of this disclosure.

FIG. 12 is a section view of the ultrasonic surgical instrument 8040 shown in FIG. 11 taken along section line 12-12 shown in FIG. 11, according to one aspect of this disclosure. In one aspect, the thickness of the transducer base plate 8044 component is greater than the thickness of the waveguide 8042 component. As shown in FIG. 12, the waveguide 8042 component defines a thickness $T_1$ and the transducer base plate 8044 component defines a thickness $T_2$, where $T_2$ is greater than $T_1$. Thus, the flat blade configuration that utilizes two components can generate more gain through the flat/sheet construction than would be created through a single thickness blade part.

Figure 13:
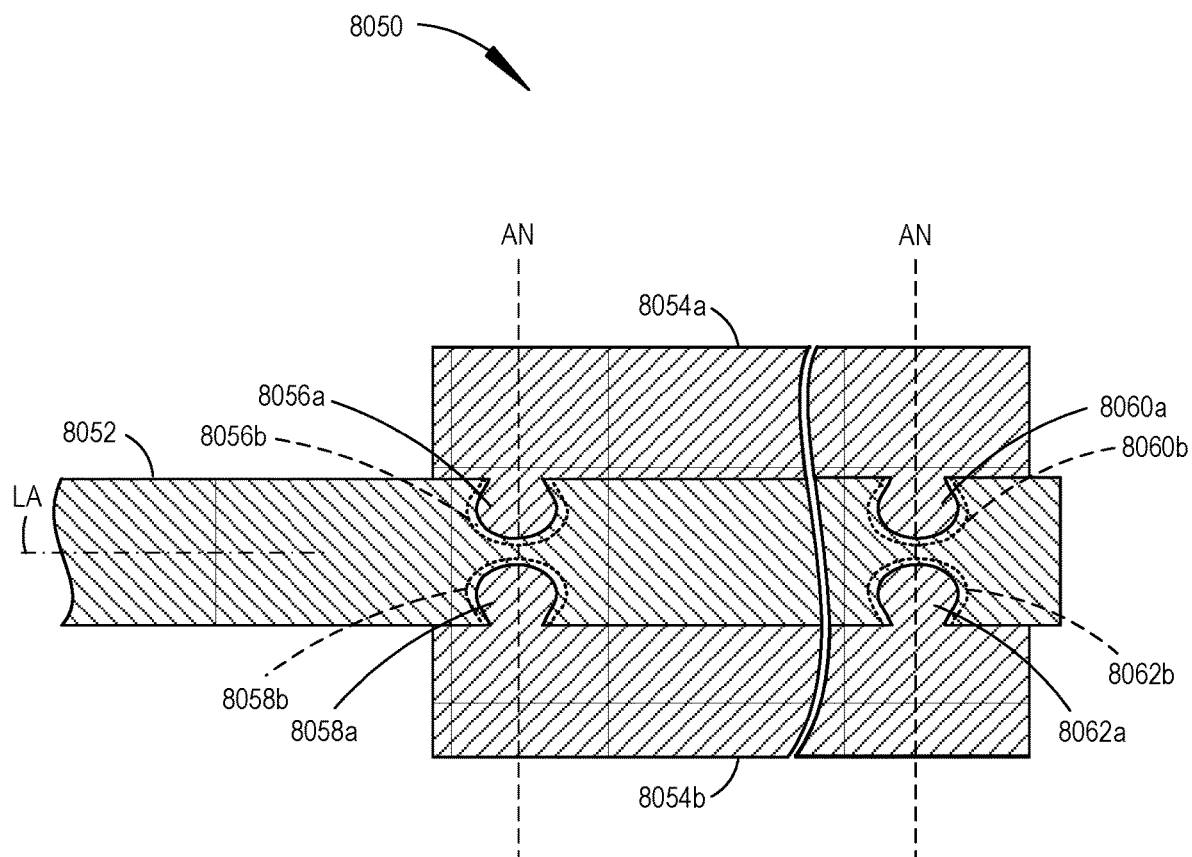
FIG. 13 is a section view of an ultrasonic surgical instrument configured in a D31 transducer architecture comprising multiple plates coupled by a thermal expansion joint, according to one aspect of this disclosure.

FIG. 13 is a section view of an ultrasonic surgical instrument 8050 configured in a D31 transducer architecture comprising multiple plates coupled by a thermal expansion joint, according to one aspect of this disclosure. The ultrasonic surgical instrument 8050 may comprise multiple pieces to reduce material waste and provide the ability to use alternate materials and/or manufacturing methods for the waveguide 8052 and the transducer base plate 8054a, 8054b (e.g., a transducer mounting portion). In one aspect, the waveguide 8052 and the transducer base plate 8054a, 8054b are made separately from flat metal stock suitable for transmitting ultrasonic vibrations such as titanium, titanium alloy, aluminum, or aluminum alloy, for example, as described herein. For example, the waveguide 8052 and the transducer base plate 8054a, 8054b are two separate pieces. The ultrasonic surgical instrument 8050 includes an ultrasonic waveguide 8052 and a two flange plates 8054a, 8054b attached to the waveguide 8052. The waveguide 8052 is made from small rectangular stock of metal such as titanium, titanium alloy, aluminum, or aluminum alloy suitable for transmitting ultrasonic energy. The two flange plates 8054a, 8054b are made from similar stock material or different stock materials. In either case, the material should be suitable for transmitting ultrasonic energy along the longitudinal axis LA.

The first flange plate 8054a includes one or more male jigsaw puzzle pieces 8056a, 8060a stamped in the body portion of the first flange plate 8054a. The second flange plate 8054b includes one or more male jigsaw puzzle pieces 8058a, 8062a stamped in the body portion of the second flange plate 8054b. One side of the waveguide 8052 includes one or more female jigsaw puzzle pieces 8056*b*, 8060*b* stamped in a body portion of the waveguide 8052 sized and configured to mate with the corresponding male jigsaw puzzle pieces 8056*a*, 8060*a*. An opposite side of the waveguide 8052 includes one or more female jigsaw puzzle pieces 8058*b*, 8062*b* stamped in a body portion of the waveguide 8052 sized and configured to mate with the corresponding male jigsaw puzzle pieces 8058*a*, 8062*a*. As shown in FIG. 13, the male and female jigsaw puzzle pieces 8056*a-b*, 8058*a-b*, 8060*a-b*, 8062*a-b* are disposed on an AN section of the ultrasonic transmission waveguide 8052. When fully assembled, the ultrasonic instrument 8050 is configured to transmit ultrasonic energy to the distal end of the waveguide 8052 along the longitudinal axis LA.

The waveguide 8052 female jigsaw puzzle pieces 8056*b*, 8058*b*, 8060*b*, 8062*b* are dimensioned smaller than the corresponding dimensions of the male flange jigsaw puzzle pieces 8056*a*, 8058*a*, 8060*a*, 8062*a*. Thus, the flange plates 8054*a*, 8054*b* are nominally larger than the waveguide 8052. The size mismatch prevents assembly of the waveguide 8052 to the flange plates 8054*a*, 8054*b* at room temperature. However, by heating the waveguide 8052 to a high temperature, the female jigsaw puzzle pieces 8056*b*, 8058*b*, 8060*b*, 8062*b* dimensions increase, as shown in FIG. 13 in the expanded configuration, making it possible to mate the waveguide plate 805 and the flange plates 8054*a*, 8054*b*. As the waveguide 8052 cools, the jigsaw puzzle type male and female joints contract and achieves an interference fit between the waveguide 8052 and the flange plates 8054*a*, 8054*b*. In other aspects, the waveguide 8052 may include male jigsaw puzzle pieces configured to mate with female jigsaw puzzle pieces formed on the flange plates 8054*a*, 8054*b*. In another aspect, rather than heating the waveguide 8052, the flange plates 8054*a*, 8054*b* may be cooled or frozen to shrink the dimensions prior to mating with the waveguide 8052.

Figure 14:
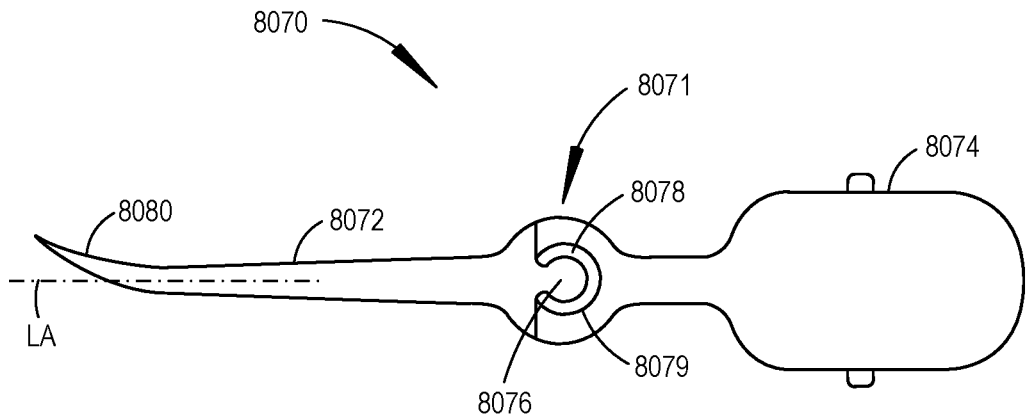
FIG. 14 is side view of an ultrasonic surgical instrument configured in a D31 transducer architecture comprising separate ultrasonic waveguide and ultrasonic transducer base plate shown in a coupled configuration, according to one aspect of this disclosure.

FIG. 14 is side view of an ultrasonic surgical instrument 8070 configured in a D31 transducer architecture comprising separate ultrasonic waveguide 8072 and ultrasonic transducer base plate 8074 (e.g., a transducer mounting portion) shown in a coupled configuration, according to one aspect of this disclosure. The waveguide 8072 is coupled to the transducer base plate 8074 by a C-shaped pin joint 8071 comprising a C-shaped pin 8078 press fit between the waveguide 8072 and the transducer base plate 8074. The ultrasonic surgical instrument 8070 may comprise multiple pieces to reduce material waste and provide the ability to use alternate materials and/or manufacturing methods for the waveguide 8072 and the transducer base plate 8074. In one aspect, the waveguide 8072 and the transducer base plate 8074 are made separately from flat metal stock suitable for transmitting ultrasonic vibrations such as titanium, titanium alloy, aluminum, or aluminum alloy, for example, as described herein. For example, the waveguide 8072 and the transducer base plate 8074 are two separate pieces and can be made of the same material or different materials suitable for transmitting ultrasonic energy along the longitudinal axis LA. The C-shaped pin 8078 may be made of materials that are similar to or different from the materials that the waveguide 8072 or transducer base plate 8074 are made from.

A distal end of the waveguide 8072 defines an ultrasonic blade 8080 and a proximal end of the waveguide 802 defines a male jigsaw puzzle piece 8076 sized and configured to clearance fit within a complementary mating female jigsaw puzzle piece 8079 defined by a distal end of the transducer base plate 8074. The transducer base plate 8074 defines flat faces 8075 on opposite sides of the transducer base plate 8074 suitable to attach and support a PZT piezoelectric element on each flat face 8005 similar to the D31 configuration shown by way of example in FIG. 3. Extending distally from the flat faces 8075 is a neck 8077 that concludes in a female jigsaw puzzle piece 8079. The female jigsaw puzzle piece 8079 also defines a C shape to receive a C-shaped pin 8078. When fully assembled, the ultrasonic instrument 8070 is configured to transmit ultrasonic energy to the distal end of the waveguide 8072 along the longitudinal axis LA.

Figure 15:
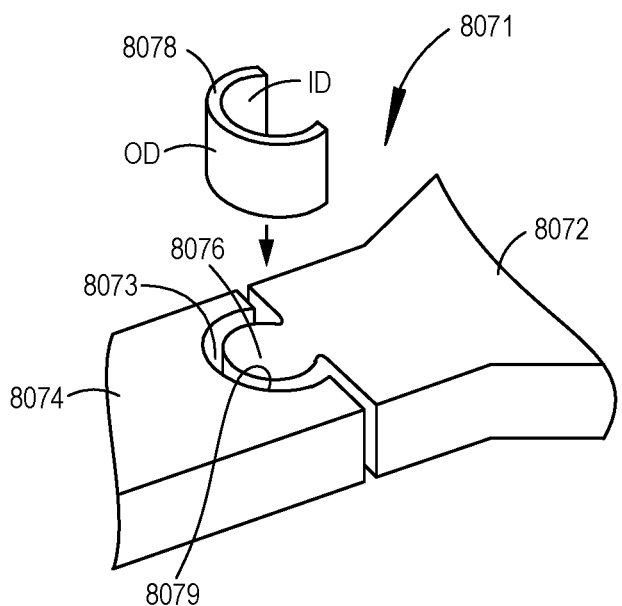
FIG. 15 is an exploded view of the C-shaped pin joint shown in FIG. 14, according to one aspect of this disclosure.
Figure 16:
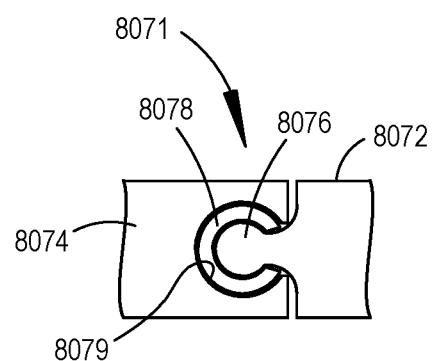
FIG. 16 is a plan view of the C-shaped pin joint shown in FIG. 14, according to one aspect of this disclosure.

FIG. 15 is an exploded view and FIG. 16 is a plan view of the C-shaped pin joint 8071 shown in FIG. 14, according to one aspect of this disclosure. FIG. 15 shows the C-shaped pin 8078 in the process of being assembled into an aperture 8073 or gap defined between the male and female jigsaw puzzle pieces 8076, 8079. FIG. 16 shows the C-shaped pin 8078 fully pressed into the aperture 8073 to achieve the C-shaped pin joint 8071. The C-shaped pin 8078 has an outside diameter (OD) that is slightly lager than the diameter of the female jigsaw puzzle piece 8079 and an inside diameter (ID) that is slightly smaller than the diameter of the male jigsaw puzzle piece 8076. The C-shaped clip 8078 is be pressed into the aperture 8073 defined between the female and male jigsaw puzzle pieces 8076, 8079 to lock them in place.

In one aspect, the thermal expansion and contraction properties of the waveguide 8072, transducer base plate 8074, or C-shaped pin 8078 materials may be exploited to achieve a tight joint 8078 at room temperature conditions under which the ultrasonic surgical instrument 8070 will be used. For example, one or ore of the components may be heated to achieve an easier fit to expand the size of the male and female jigsaw puzzle pieces 8076, 8079. In one aspect, the C-shaped pin 8078 may be heated before the C-shaped pin 8078 is press fit into the aperture 8073. In another aspect, the mated male and female jigsaw puzzle pieces 8076, 8079 may be heated before the C-shaped pin 8078. In other aspects, the C-shaped pin 8078 may be sized slightly larger than the aperture 8073 such that the C-shaped pin 8078 is chilled to contract its size prior to press fitting the C-shaped pin 8078 into the aperture 8073. Once the temperature of C-shaped pin 8078 is warmed up to room temperature, the C-shaped pin 8078 expands and achieves a tight fit. In one aspect, the C-shaped pin 8078 may be made of similar or different material to the waveguide 8072 or transducer base plate 8074. In an alternate form, the C-shaped pin 8078 may be replaced by a heated liquid metal that fills the aperture 8073 to achieve the C-shaped pin joint 8071.

FIG. 17 is a side view of an ultrasonic surgical instrument 8100 configured in a D31 transducer architecture comprising separate ultrasonic waveguide 8102 and ultrasonic transducer base plate 8104 (e.g., a transducer mounting portion) components shown in a coupled configuration, according to one aspect of this disclosure. The ultrasonic surgical instrument 8100 may comprise multiple pieces to reduce material waste and provide the ability to use alternate materials and/or manufacturing methods for the waveguide 8102 and the transducer base plate 8104. In one aspect, the waveguide 8102 and the transducer base plate 8104 are made separately from flat metal stock suitable for transmitting ultrasonic vibrations such as titanium, titanium alloy, aluminum, or aluminum alloy, for example, as described herein. For example, the waveguide 8102 and the transducer base plate 8104 are two separate pieces. The transducer base plate 8104 defines flat faces 8103 on opposite sides of the transducer base plate 8104 suitable to attach and support a PZT piezoelectric element on each flat face 8103 similar to the D31 configuration shown by way of example in FIG. 3. The waveguide 8102 and the transducer base plate 8104 are made separately from flat metal stock suitable for transmitting ultrasonic vibrations such as titanium, titanium alloy, aluminum, or aluminum alloy, for example, as described herein. The waveguide 8102 and the transducer base plate 8104 may be made of the same material or different materials suitable for transmitting ultrasonic energy along the longitudinal axis. When fully assembled, the ultrasonic instrument 8100 is configured to transmit ultrasonic energy to the distal end of the waveguide 8102 along the longitudinal axis LA.

FIG. 18 is a section view of the ultrasonic surgical instrument 8100 along section line 18-18 shown in FIG. 17, according to one aspect of this disclosure. With reference to FIGS. 17 and 18, the waveguide 8102 is coupled to an ultrasonic transducer base plate 8104 by slidably receiving the proximal end of the waveguide 8102 into a notch 8105 defined at a distal end of the transducer base plate 8104. A pin 8108 is then press fit through a transverse pin opening 8106 defined by the distal end of the transducer base plate 8104 and a transverse pin opening 8109 defined by the proximal end of the waveguide 8102. The transverse pin openings 8106, 8109 line up when the waveguide 8102 is inserted into the notch 8105 and is seated against a back wall 8101 of the notch 8105. The diameter of the pin 8108 is slightly larger than the diameter of the pin openings 8106, 8109 such that force is required to press fit the pin 8108 into the pin openings 8106, 8109 to achieve an interference pin joint 8107. The waveguide 8102 and the transducer base plate 8104 may be of similar or different materials. The pin 8108, waveguide 8102, and transducer base plate 8104 may be made of similar or different materials. In one aspect, the thermal expansion and thermal contraction properties of the pin 8108, waveguide 8102, and transducer base plate 8104 may be exploited to provide a tight fitting pin joint 8107. For example, in one aspect, the waveguide 8102 and transducer base plate 8104 may be heated to expand the openings 8106, 8109 prior to inserting the pin 8108 into the openings 8106, 8109. Alternatively, the pin 8108 may be chilled prior to inserting the pin 8108 into the openings 8106, 8109.

Figure 19:
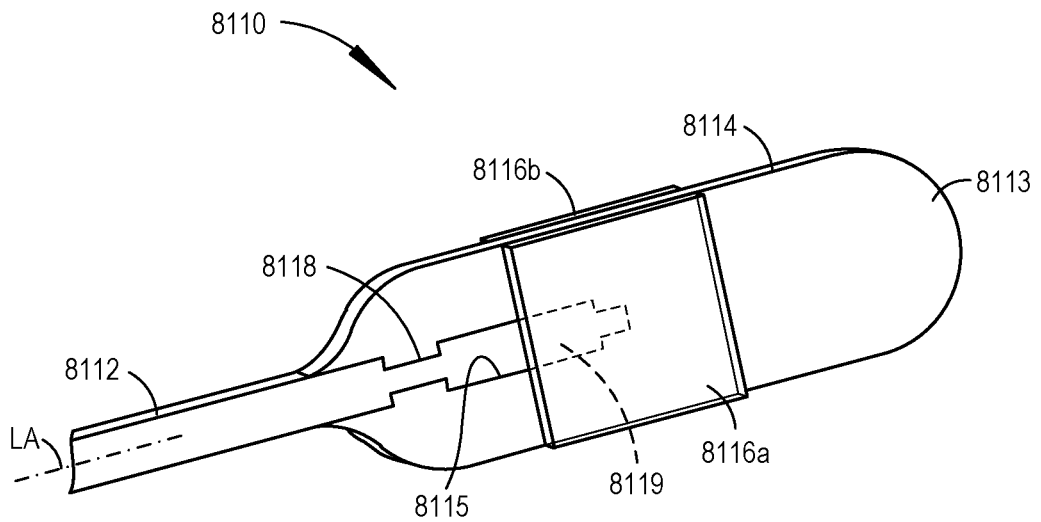
FIG. 19 is a perspective view an ultrasonic surgical instrument configured in a D31 transducer architecture comprising separate ultrasonic waveguide and ultrasonic transducer base plate components shown in a coupled configuration, according to one aspect of this disclosure.

FIG. 19 is a perspective view an ultrasonic surgical instrument 8110 configured in a D31 transducer architecture comprising separate ultrasonic waveguide 8112 and ultrasonic transducer base plate 8114 (e.g., a transducer mounting portion) components shown in a coupled configuration, according to one aspect of this disclosure. The ultrasonic surgical instrument 8110 may comprise multiple pieces to reduce material waste and provide the ability to use alternate materials and/or manufacturing methods for the waveguide 8112 and the transducer base plate 8114. In one aspect, the waveguide 8112 and the transducer base plate 8114 are made separately from flat metal stock suitable for transmitting ultrasonic vibrations such as titanium, titanium alloy, aluminum, or aluminum alloy, for example, as described herein. In the illustrated aspect, the ultrasonic surgical instrument 8110 is divided into a separate one-piece waveguide 8112 and a one-piece transducer base plate 8114. For example, the waveguide 8112 and the transducer base plate 8114 are two separate pieces and can be made of the same material or different materials suitable for transmitting ultrasonic energy along the longitudinal axis LA.

A proximal end of the waveguide 8112 is coupled to the transducer base plate 8114 within a cutout 8115 defined by the transducer base plate 8114 (see also FIG. 20) to form a press fit joint. The transducer base plate 8114 defines flat faces 8113 on opposite sides of the transducer base plate 8114 suitable to attach and support a PZT piezoelectric element 8116a, 8116b on each flat face 8113 similar to the D31 configuration shown by way of example in FIG. 3. A portion of the waveguide 8119 located beneath and is sandwiched between the piezoelectric elements 8116a, 8116b to form a two-piece divided of the waveguide 8112 and transducer base plate 8114. The waveguide 8112 and the transducer base plate 8114 are made separately from flat metal stock suitable for transmitting ultrasonic vibrations such as titanium, titanium alloy, aluminum, or aluminum alloy, for example, as described herein. When fully assembled, the ultrasonic instrument 8110 is configured to transmit ultrasonic energy to the distal end of the waveguide 8112 along the longitudinal axis LA.

Figure 20:
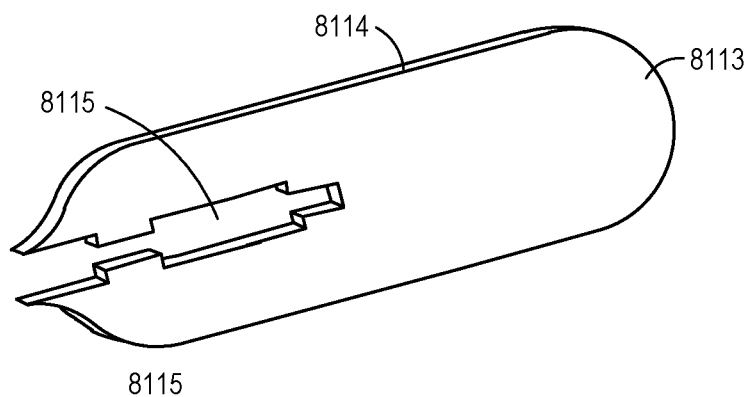
FIG. 20 is a perspective view the ultrasonic surgical instrument shown in FIG. 19 with the waveguide and the piezoelectric elements removed to show the cutout configured to receive a proximal portion of the waveguide, according to one aspect of this disclosure.

FIG. 20 is a perspective view the ultrasonic surgical instrument 8110 shown in FIG. 19 with the waveguide 8112 and the piezoelectric elements 8116a, 8116b removed to show the cutout 8115 configured to receive a proximal portion of the waveguide 8112, according to one aspect of this disclosure. With reference to FIGS. 19 and 20, in one aspect, the cutout 8115 defined by the transducer base plate 8114 is configured to receive a proximal portion 8118 of the waveguide 8112. The proximal portion waveguide 8119 is inserted in the cutout 8115 defined by the transducer base plate 8114 and is rejoined to the transducer base plate 8114 through the addition of the piezoelectric elements 8116a, 8116b. The transducer base plate 8114 cutout 8115 can have varying shapes to increase retention or minimize material waste. The transducer base plate 8114 can be configured in two or more pieces to increase retention or minimize material waste. Varying materials can be used to join the piezoelectric elements 8116a, 8116b material to the combination of the waveguide portion 8119 and transducer base plate 8114 such as adhesives, welding, soldering, or combinations thereof.

Figure 21:
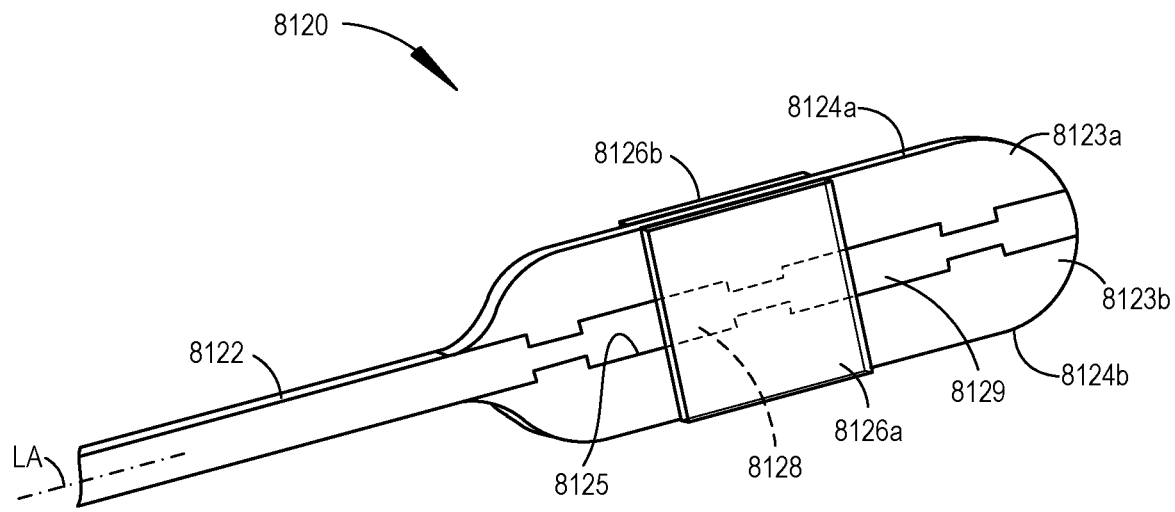
FIG. 21 is a perspective view of an ultrasonic surgical instrument configured in a D31 transducer architecture comprising ultrasonic waveguide and ultrasonic transducer base plate components shown in a coupled configuration, according to one aspect of this disclosure.

FIG. 21 is a perspective view of an ultrasonic surgical instrument 8120 configured in a D31 transducer architecture comprising ultrasonic waveguide 8122 and ultrasonic transducer base plate 8124a, 8124b (e.g., a transducer mounting portion) components shown in a coupled configuration, according to one aspect of this disclosure. The ultrasonic surgical instrument 8120 may comprise multiple pieces to reduce material waste and provide the ability to use alternate materials and/or manufacturing methods for the waveguide 8122 and the transducer base plate 8124a, 8124b. In one aspect, the waveguide 8122 and the transducer base plate 8124a, 8124b are made separately from flat metal stock suitable for transmitting ultrasonic vibrations such as titanium, titanium alloy, aluminum, or aluminum alloy, for example, as described herein. In the illustrated aspect, the ultrasonic surgical instrument 8120 is divided into separate one-piece waveguide 8122 and two-piece transducer base plate 8124a, 8124b. For example, the waveguide 8122 and the transducer base plate 8124a, 8124b are three separate pieces and can be made of the same material or different materials suitable for transmitting ultrasonic energy along the longitudinal axis LA.

A proximal end of the waveguide 8122 is coupled to the transducer base plate 8124a, 8124b within a cutout 8125 defined by the transducer base plate 8124a, 8124b (see also FIG. 22) to form a press fit joint. The transducer base plate 8124a, 8124b defines flat faces 8123a, 8123b on opposite sides of the transducer base plate 8124a, 8124b suitable to attach and support a PZT piezoelectric element 8126a, 8126b on each flat face 8123a, 8123b similar to the D31 configuration shown by way of example in FIG. 3. A proximal portion of the waveguide 8128 is located beneath and is sandwiched between the piezoelectric elements 8126a, 8126b to form a three-piece divided of the waveguide 8122 and transducer base plate 8124a, 8124b. Another proximal portion of the waveguide 8129 extends through the proximal end of the transducer base plate 8124a, 8124b to divided the transducer base plate 8124a, 8124b into two pieces. The waveguide 8122 and the transducer base plate 8124a, 8124b are made separately from flat metal stock suitable for transmitting ultrasonic vibrations such as titanium, titanium alloy, aluminum, or aluminum alloy, for example, as described herein. When fully assembled, the ultrasonic instrument 8120 is configured to transmit ultrasonic energy to the distal end of the waveguide 8122 along the longitudinal axis LA.

Figure 22:
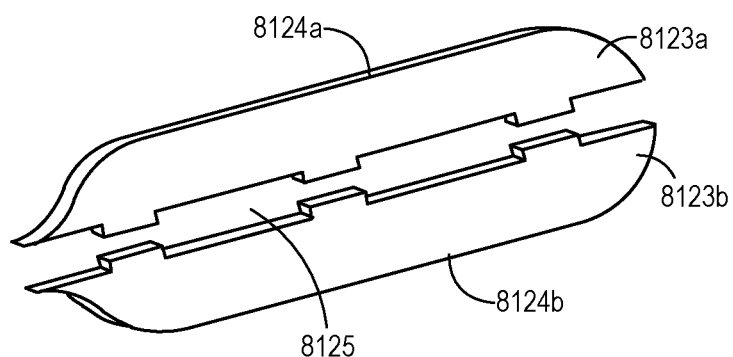
FIG. 22 is a perspective view of the ultrasonic surgical instrument shown in FIG. 21 with the waveguide and the piezoelectric elements removed to show the cutout configured to receive a proximal portion of the waveguide, according to one aspect of this disclosure.

FIG. 22 is a perspective view of the ultrasonic surgical instrument 8120 shown in FIG. 21 with the waveguide 8122 and the piezoelectric elements 8126a, 8126b removed to show the cutout 8125 configured to receive a proximal portion of the waveguide 8122, according to one aspect of this disclosure. With reference to FIGS. 21 and 22, in one aspect, the cutout 8125 is defined by the transducer base plate 8124a, 8124b is configured to receive the proximal portion 8128, 8129 of the waveguide 8122. The proximal portion of the waveguide 8128, 8129 is inserted in the cutout 8125 defined by the transducer base plate 8124a, 8124b and is rejoined to the transducer base plate 8124a, 8124b through the addition of the piezoelectric elements 8126a, 8126b. The transducer base plate 8124a, 8124b cutout 8125 can have varying shapes to increase retention or minimize material waste. The transducer base plate 8124a, 8124b can be configured in three or more pieces to increase retention or minimize material waste. Varying materials can be used to join the piezoelectric elements 8126a, 8126b material to the combination of the proximal portion of the waveguide 8128 and the transducer base plate 8124a, 8124b such as adhesives, welding, soldering, or combinations thereof.

Figure 23:
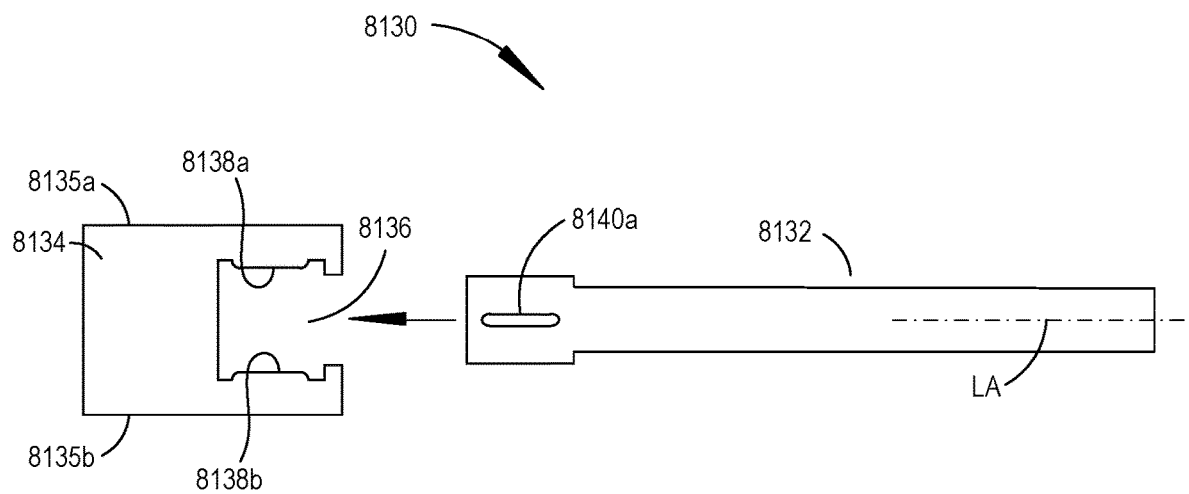
FIG. 23 is a side view of an ultrasonic surgical instrument configured in a D31 transducer architecture comprising separate ultrasonic waveguide and ultrasonic transducer base plate components shown in a decoupled configuration, according to one aspect of this disclosure.
Figure 24:
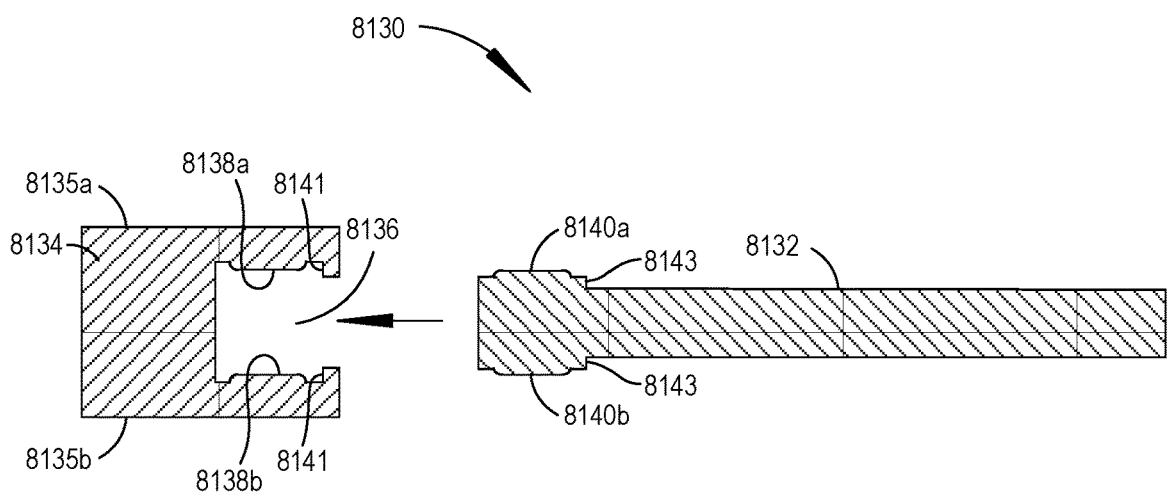
FIG. 24 is a section view of the ultrasonic surgical instrument shown in FIG. 23 with the ultrasonic waveguide rotated 90° in a decoupled configuration, according to one aspect of this disclosure.

FIG. 23 is a side view of an ultrasonic surgical instrument 8130 configured in a D31 transducer architecture comprising separate ultrasonic waveguide 8132 and ultrasonic transducer base plate 8134 (e.g., a transducer mounting portion) components shown in a decoupled configuration, according to one aspect of this disclosure. FIG. 24 is a section view of the ultrasonic surgical instrument 8130 shown in FIG. 23 with the ultrasonic waveguide 8132 rotated 90° in a decoupled configuration, according to one aspect of this disclosure. The ultrasonic surgical instrument 8130 may comprise multiple pieces to reduce material waste and provide the ability to use alternate materials and/or manufacturing methods for the waveguide 8132 and the transducer base plate 8134. In one aspect, the waveguide 8132 and the transducer base plate 8134 are made separately from flat metal stock suitable for transmitting ultrasonic vibrations such as titanium, titanium alloy, aluminum, or aluminum alloy, for example, as described herein. When fully assembled, the ultrasonic instrument 8130 is configured to transmit ultrasonic energy to the distal end of the waveguide 8152 along the longitudinal axis LA. The waveguide 8132 and transducer base plate 8134 can be made of the same material or different materials suitable for transmitting ultrasonic energy along the longitudinal axis LA.

With reference to FIGS. 23 and 24, a proximal end of the waveguide 8132 includes bump features 8140a, 8140b and the transducer base plate 8134 includes bump features 8138a, 8138b to provide a torqued press fit to join the waveguide 8132 and the transducer base plate 8134. The proximal end of the waveguide 8132 is inserted into an aperture 8136 defined by the transducer base plate 8134. Prior to coupling, the waveguide 8132 is oriented as shown in FIG. 23 where the bump features 8140a, 8140b are not aligned with the bump features 8138a, 8138b such that the waveguide 8132 is slidably received in the aperture 8136 without interference. Once the proximal end of the waveguide 8132 is inserted into the aperture 8136, the waveguide 8132 is rotated as shown in FIG. 24 to provide a torqued press fit joint. The transducer base plate 8134 defines flat faces 8135a, 8135b on opposite sides of the transducer base plate 8134 suitable to attach and support a PZT piezoelectric element on each flat face 8135a, 8135b similar to the D31 configuration shown by way of example in FIG. 3.

Figure 25:
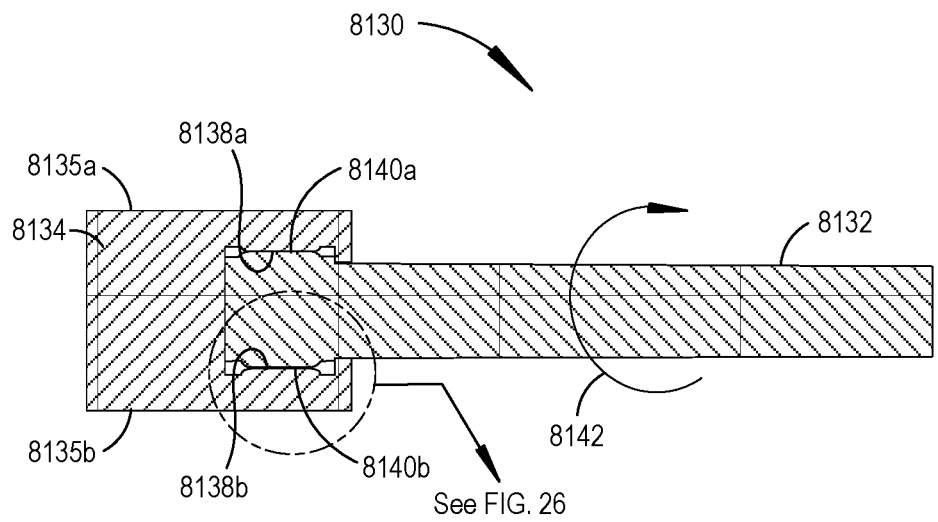
FIG. 25 is a section view of the ultrasonic surgical instrument shown in FIG. 23 with the ultrasonic waveguide rotated 90° in a coupled configuration, according to one aspect of this disclosure.
Figure 26:
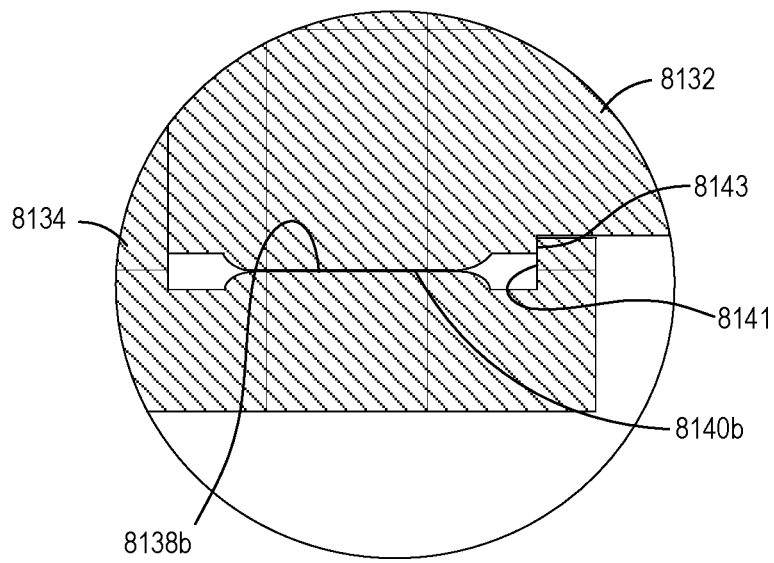
FIG. 26 is detail view of the joint between the waveguide and the transducer base plate, according to one aspect of this disclosure.

FIG. 25 is a section view of the ultrasonic surgical instrument 8130 shown in FIG. 23 with the ultrasonic waveguide 8132 rotated 90° in a coupled configuration, according to one aspect of this disclosure. FIG. 26 is detail view of the joint between the waveguide 8132 and the transducer base plate 8134, according to one aspect of this disclosure. With reference to FIGS. 23-26, once the waveguide 8132 is inserted into the aperture 8136, the waveguide may be rotated as indicated by arrow 8142 such that the bump features 8138a, 8138b on the transducer base plate 8134 and the bump features 8132 on the waveguide 8132 create a torqued press fit connection. As shown in FIG. 26, a lip 8141 defined by a distal end of the transducer base plate 8134 engages with a projection 8143 of the waveguide 8132 to prevent the proximal end of the waveguide 8132 from sliding out of the aperture 8136 after it has been torqued press fit. When fully assembled, the ultrasonic instrument 8130 is configured to transmit ultrasonic energy to the distal end of the waveguide 8152 along the longitudinal axis LA.

Figure 27:
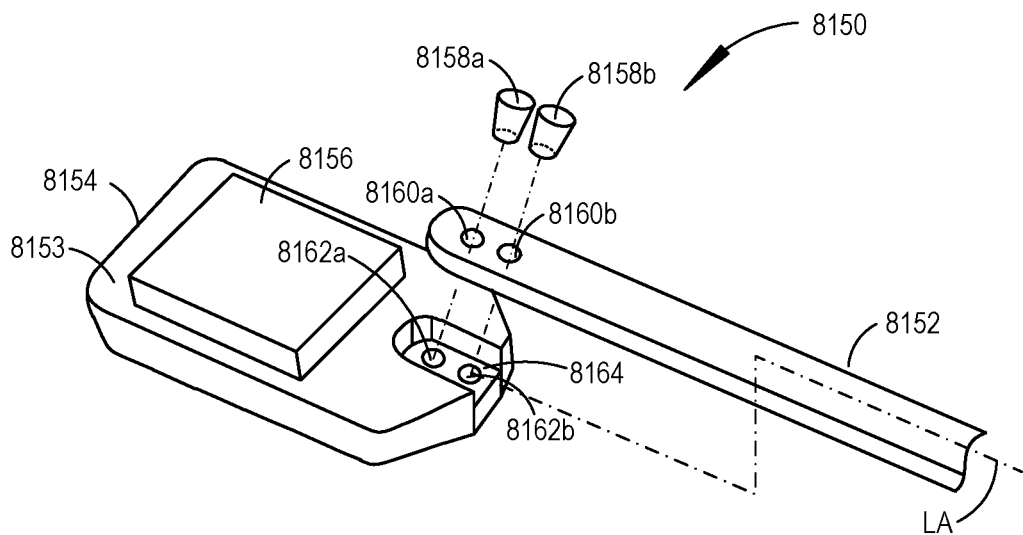
FIG. 27 is a perspective view of an ultrasonic surgical instrument configured in a D31 transducer architecture comprising separate ultrasonic waveguide and ultrasonic transducer base plate components shown in a decoupled configuration, according to one aspect of this disclosure.
Figure 28:
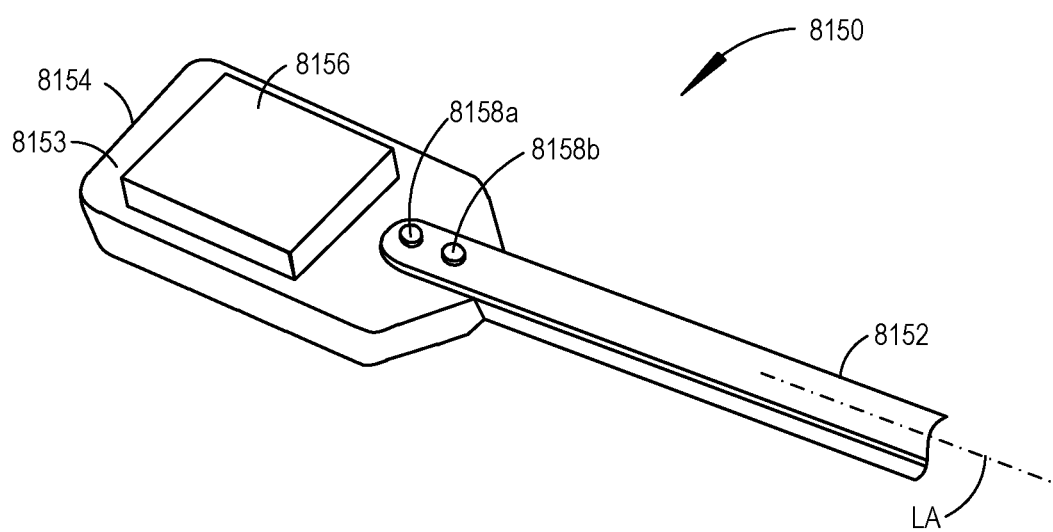
FIG. 28 is a perspective view of the ultrasonic surgical instrument shown in FIG. 27 in a coupled configuration, according to one aspect of this disclosure.

FIG. 27 is a perspective view of an ultrasonic surgical instrument 8150 configured in a D31 transducer architecture comprising separate ultrasonic waveguide 8152 and ultrasonic transducer base plate 8154 (e.g., a transducer mounting portion) components shown in a decoupled configuration, according to one aspect of this disclosure. The waveguide 8152 and the transducer base plate 8154 are coupled in a parallel tang joint attachment mechanism. FIG. 28 is a perspective view of the ultrasonic surgical instrument 8150 shown in FIG. 27 in a coupled configuration, according to one aspect of this disclosure. With reference to FIGS. 27 and 28, the ultrasonic surgical instrument 8150 may comprise multiple pieces to reduce material waste and provide the ability to use alternate materials and/or manufacturing methods for the waveguide 8152 and the transducer base plate 8154. In one aspect, the waveguide 8152 and the transducer base plate 8154 are made separately from flat metal stock suitable for transmitting ultrasonic vibrations such as titanium, titanium alloy, aluminum, or aluminum alloy, for example, as described herein. For example, the waveguide 8152 and the transducer base plate 8154 are two separate pieces. The transducer base plate 8154 defines flat faces 8153 on opposite sides of the transducer base plate 8154 suitable to attach and support a PZT piezoelectric element 8156 (not shown) on each flat face 8153 similar to the D31 configuration shown by way of example in FIG. 3.

Still with reference to FIGS. 27 and 28, a parallel tang joint attachment mechanism is disclosed to join the waveguide 8152 and the transducer base plate 8154. A proximal end of the waveguide 8152 is coupled to a distal end of the transducer base plate 8154. A recessed receptacle 8164 in the distal end of the transducer base plate 8154 is configured to accept the profile of a proximal end of the waveguide 8152. Fasteners 8158a, 8158b such as pins, screws, rivets, or other such mechanisms, are disposed through apertures 8160a, 8160b defined at the proximal end of the waveguide 8152 are received in corresponding apertures 8162*a*, 8162*b* defined by the recessed receptacle 8164 can be used to lock the waveguide 8152 and the transducer base plate 8154 in place. Alternatively, the waveguide 8152 and the transducer base plate 8154 can be spot welded in the recessed receptacle 8164. When fully assembled, the ultrasonic instrument 8150 is configured to transmit ultrasonic energy to the distal end of the waveguide 8152 along the longitudinal axis LA. The waveguide 8152 and the transducer base plate 8154 can be made of the same material or different materials suitable for transmitting ultrasonic energy along the longitudinal axis LA.

Still with reference to FIGS. 27 and 28, the ultrasonic surgical instrument 8150 may comprise multiple pieces to reduce material waste and provide the ability to use alternate materials and/or manufacturing methods for the waveguide 8152 and the transducer base plate 8154. In one aspect, the waveguide 8152 and the transducer base plate 8154 are made separately from flat metal stock suitable for transmitting ultrasonic vibrations such as titanium, titanium alloy, aluminum, or aluminum alloy, for example, as described herein. For example, the waveguide 8152 and the transducer base plate 8154 are two separate pieces. The transducer base plate 8154 defines flat faces 8153 on opposite sides of the transducer base plate 8154 suitable to attach and support a PZT piezoelectric element 8156 (not shown) on each flat face 8153 similar to the D31 configuration shown by way of example in FIG. 3.

Figure 29:
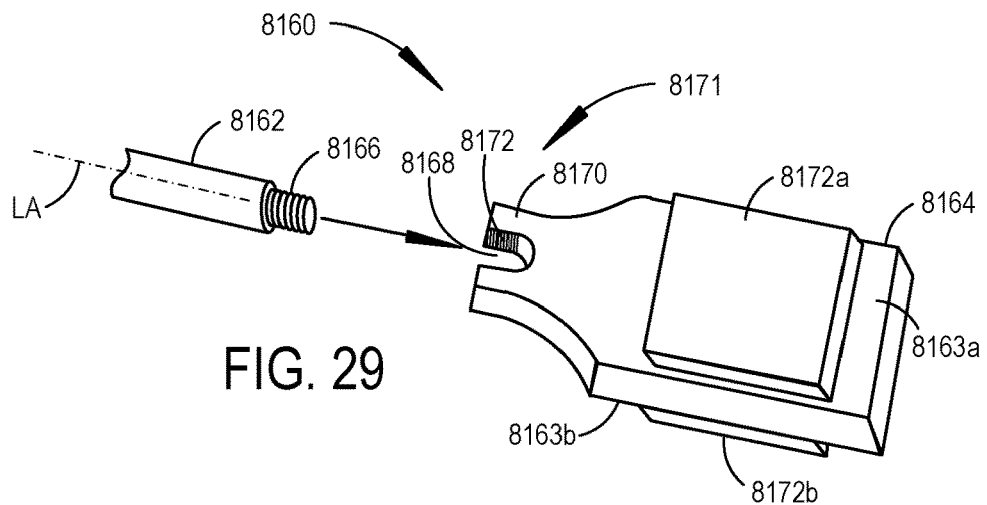
FIG. 29 is a perspective view of an ultrasonic surgical instrument configured in a D31 transducer architecture comprising separate ultrasonic waveguide and ultrasonic transducer base plate components shown in a decoupled configuration, according to one aspect of this disclosure.

FIG. 29 is a perspective view of an ultrasonic surgical instrument 8160 configured in a D31 transducer architecture comprising separate ultrasonic waveguide 8162 and ultrasonic transducer base plate 8164 (e.g., a transducer mounting portion) components shown in a decoupled configuration, according to one aspect of this disclosure. The waveguide 8162 includes a male threaded section 8166 and the transducer base plate 8164 includes a female threaded section 8172 in a U-shaped slot 8168 of the distal end 8170 of the transducer base plate 8164 to achieve a threaded joint 8171. The ultrasonic surgical instrument 8160 may comprise multiple pieces to reduce material waste and provide the ability to use alternate materials and/or manufacturing methods for the waveguide 8162 and the transducer base plate 8164. In one aspect, the waveguide 8162 and the transducer base plate 8164 are made separately from flat metal stock and can be made of the same material or different materials suitable for transmitting ultrasonic energy along the longitudinal axis LA such as titanium, titanium alloy, aluminum, or aluminum alloy, for example, as described herein. For example, the waveguide 8162 and the transducer base plate 8164 are two separate pieces joined by a threaded connection. The transducer base plate 8164 defines flat faces 8163*a*, 8163*b* on opposite sides of the transducer base plate 8164 suitable to attach and support a PZT piezoelectric element 8172*a*, 8172*b* on each flat face 8163*a*, 8163*b* similar to the D31 configuration shown by way of example in FIG. 3. The waveguide 8162 includes a male threaded section 8166 and the transducer base plate 8164 includes a female threaded section 8172 in a U-shaped slot 8168 of the distal end 8170 of the transducer base plate 8164.

Figure 30:
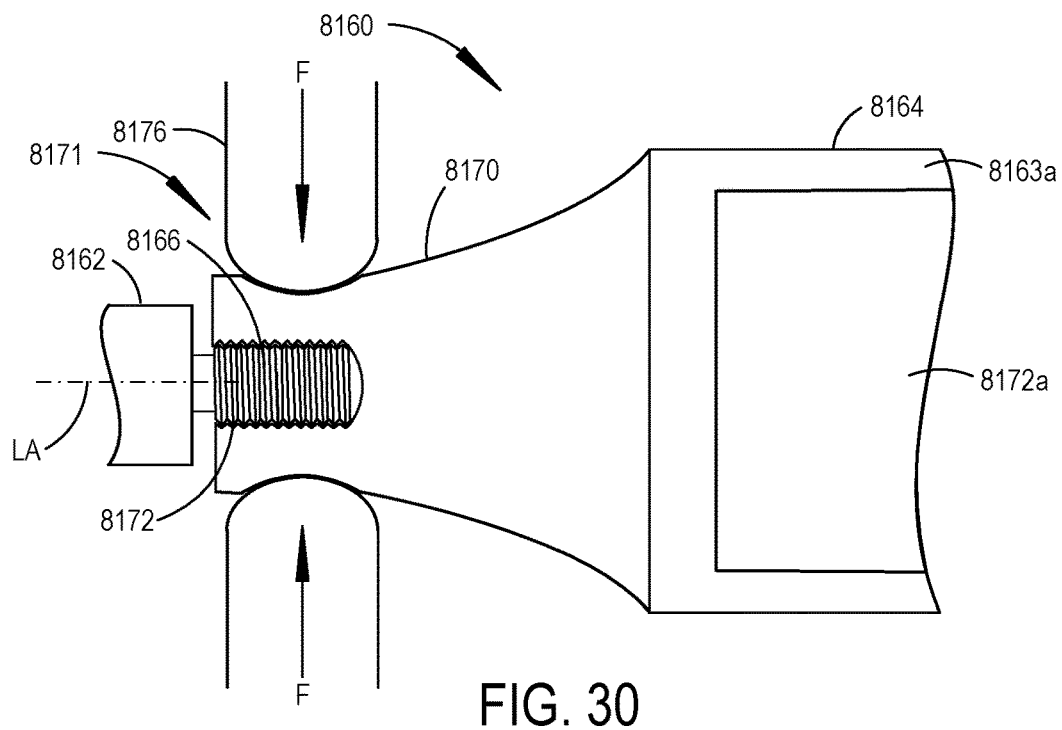
FIG. 30 is a side view of the threaded joint showing the threaded section of the waveguide threaded into the threaded section of the transducer base plate, according to one aspect of this disclosure.

FIG. 30 is a side view of the threaded joint 8171 showing the threaded section 8166 of the waveguide 8162 threaded into the threaded section 8172 of the transducer base plate 8164, according to one aspect of this disclosure. Once the waveguide 8162 is in threaded engagement with the transducer base plate 8164, a forming force F is applied by a forming press 8176 to the external walls of the U-shaped slot 8168 defining the threaded section 8172 to more securely attach the two components in place. The threaded section 8166 of the waveguide 8162 may be made as a separate component using Swiss screw machining, conventional lathe, thread forming on rod stock material, or similar techniques. The threaded section 8166 is joined to the flat waveguide 8162 section by way of lateral forming, forging, or similar process. Accordingly, the threads in the threaded section 8166 are not cut or formed on the flat waveguide 8162 section prior to the joining operation (by forming, forging, or similar process) and thus lowering the cost of the flat section of the waveguide 8162. In one aspect, the threads of the threaded section 8166 of the waveguide 8162 can be made during the forming, forging or similar process. In one aspect, the flat waveguide 8162 section is made from a formable grade of aluminum. The threaded section 8166, however, is made from a material that is harder than the waveguide 8162 material such as titanium.

Figure 31:
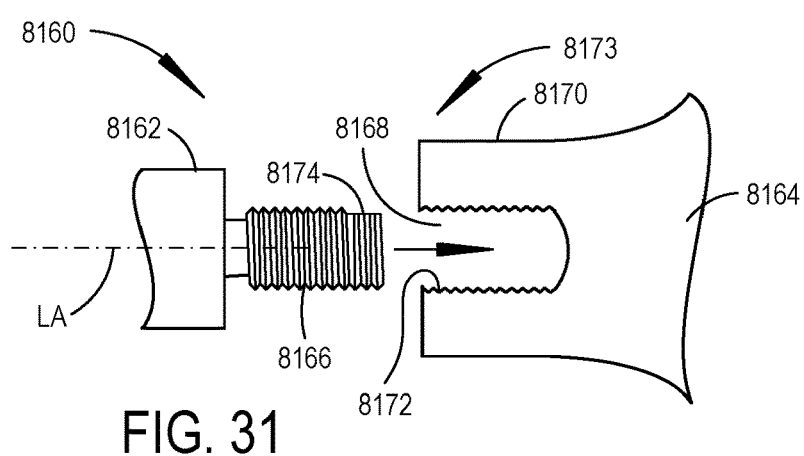
FIG. 31 is a side view of an alternate threaded joint where the threaded section includes a rotational orientation section to provide rotary alignment about the longitudinal axis LA of the threaded section of the waveguide, according to one aspect of this disclosure.

FIG. 31 is a side view of an alternate threaded joint 7183 where the threaded section 8166 includes a rotational orientation section to provide rotary alignment about the longitudinal axis LA of the threaded section 8166 of the waveguide 8162, according to one aspect of this disclosure. The two joined sections of the waveguide 8162 and the transducer base plate 8164 are maintained by a flat cut 8174 formed on or near the proximal end of the threaded section 8166 of the threaded waveguide 8162, for example, at the very proximal end of the threaded section 8166. The flat cut 8174 is substantially parallel to the sides of the slot 8168 that receives the threaded section 8166 such that when the threaded section 8166 is formed, the flat 8174 portion of the threaded section 1866 section is threadingly engaged with the threaded section 8172 of the slot 8168. In one aspect, a laser may be used to fuse the waveguide 8162 and the transducer base plate 8164 at select points or interfaces of the waveguide 8162 and transducer base plate 8164. In another aspect, adhesive may be used to fuse the waveguide 8162 and the transducer base plate 8164 at select points or interfaces of the waveguide 8162 and transducer base plate 8164.

Figure 32:
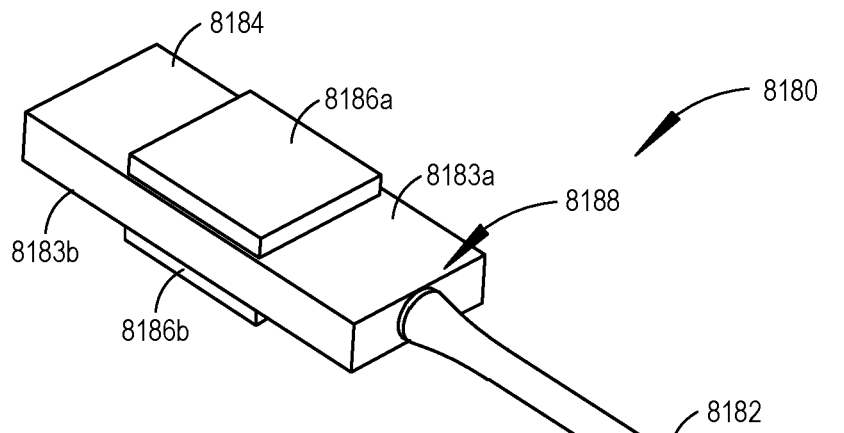
FIG. 32 is a perspective view of an ultrasonic surgical instrument configured in a D31 transducer architecture comprising separate ultrasonic waveguide and ultrasonic transducer base plate components shown in a coupled configuration, according to one aspect of this disclosure.
Figure 33:
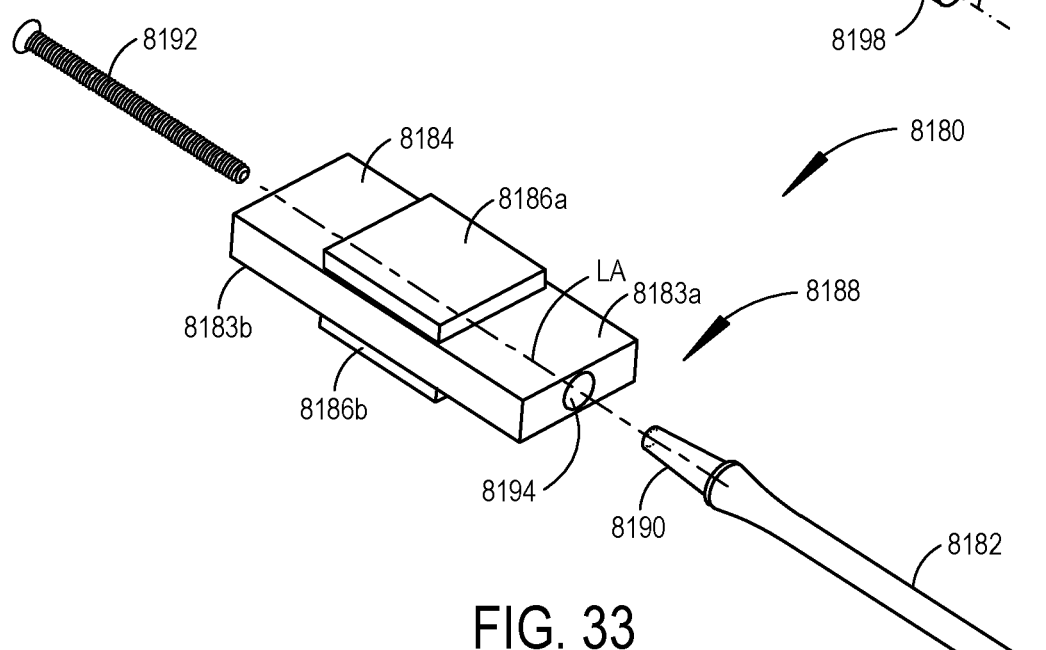
FIG. 33 is an exploded view of the ultrasonic surgical instrument shown in FIG. 32, according to one aspect of this disclosure.
Figure 34:
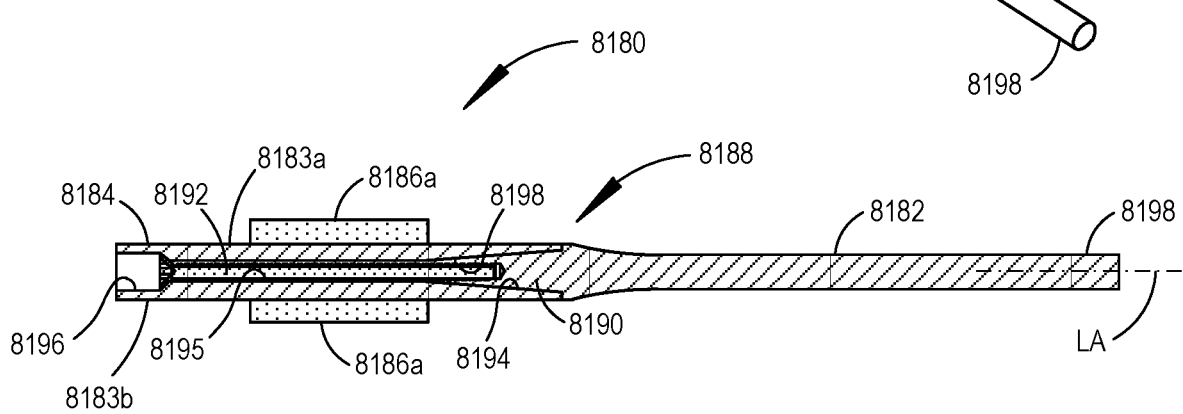
FIG. 34 is a section view of the ultrasonic surgical instrument shown in FIG. 32, according to one aspect of this disclosure.

FIG. 32 is a perspective view of an ultrasonic surgical instrument 8180 configured in a D31 transducer architecture comprising separate ultrasonic waveguide 8182 and ultrasonic transducer base plate 8184 (e.g., a transducer mounting portion) components shown in a coupled configuration, according to one aspect of this disclosure. FIG. 33 is an exploded view of the ultrasonic surgical instrument 8180 shown in FIG. 32, according to one aspect of this disclosure. FIG. 34 is a section view of the ultrasonic surgical instrument 8180 shown in FIG. 32, according to one aspect of this disclosure.

With reference to FIGS. 32-34, the waveguide 8182 is attached to the transducer base plate 8184 by a threaded joint 8188. The ultrasonic surgical instrument 8180 may comprise multiple pieces to reduce material waste and provide the ability to use alternate materials and/or manufacturing methods for the waveguide 8182 and the transducer base plate 8184. In one aspect, the waveguide 8182 is made from round metal stock and the transducer base plate 8184 is made separately from flat metal stock. The metal for both components is suitable for transmitting ultrasonic vibrations and may be titanium, titanium alloy, aluminum, or aluminum alloy, for example, as described herein. For example, the waveguide 8182 and the transducer base plate 8184 are two separate pieces joined by a threaded joint 8188 and can be made of the same material or different materials suitable for transmitting ultrasonic energy along the longitudinal axis LA. This configuration enables the waveguide 8182 or transducer base plate 8184 to be replaced in the field. The transducer base plate 8184 defines flat faces 8183*a*, 8183*b* on opposite sides of the transducer base plate 8184 suitable to attach and support a PZT piezoelectric element 8186*a*, 8186*b* on each flat face 8183*a*, 8183*b* similar to the D31 configuration shown by way of example in FIG. 3.

As shown in FIGS. 32 and 33, the distal end of the waveguide 8182 defines a blade 8198 for treating tissue and a proximal end of the waveguide 8182 defines a conical feature 8190 that matches a complementary conical channel 8194 formed at a distal end of the transducer base plate 8184. The conical channel 8194 meets a cylindrical channel 8195 that is defined through the proximal end of the transducer base plate 8184. The conical feature 8190 of the waveguide 8182 includes female threads 8198 and is bolted to the transducer base plate 8184 by a screw 8192 that is inserted from the proximal end of the transducer base plate 8184 defining a countersunk aperture 8196, for example, through the cylindrical aperture 8195, and screws into the female threads 8198 defined by the conical feature 8190 of the waveguide 8182. In use, the ultrasonic vibrational movement is transmitted from the transducer base plate 8184 to the waveguide 8182 along the longitudinal axis LA through the respective conical surfaces 8190, 8194 in contact. The angle of the conical features is selected such that the compression on their surfaces in contact is high, while the screw is exposed to a low stress, so it can be small. The transducer base plate 8184 can be made of aluminum or other suitable metal material. This is advantageous in terms of low cost, availability, ease of machining, and thermal conductivity for the heat management of the piezoelectric elements 8186*a*, 8186*b*.

Figure 35:
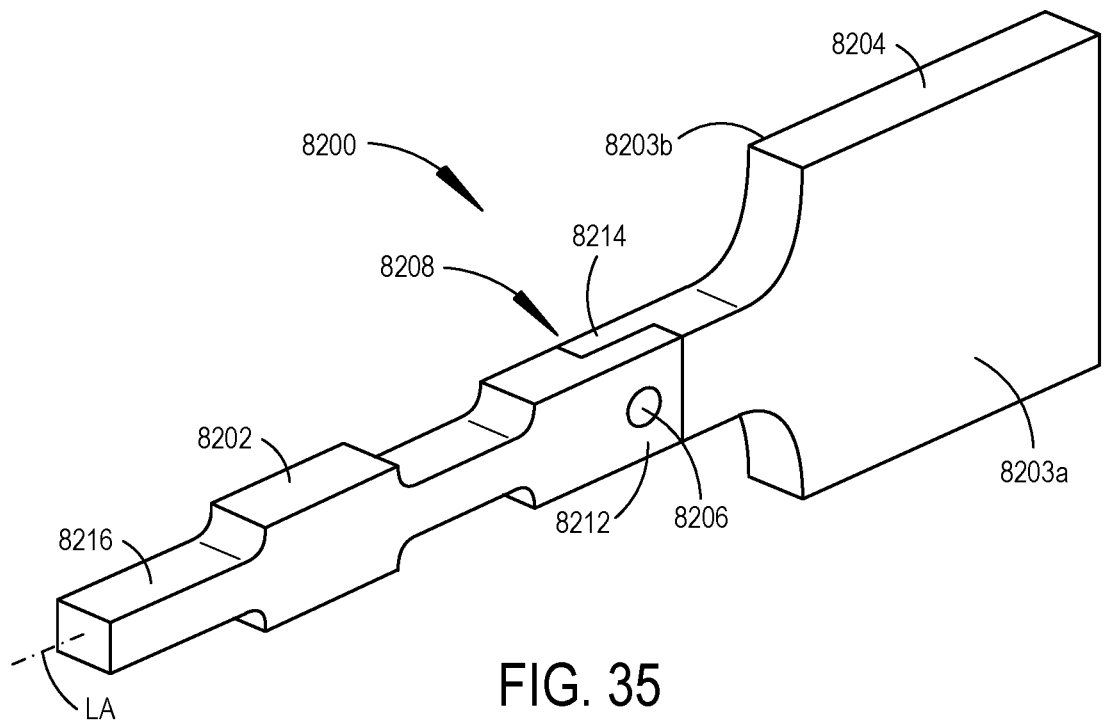
FIG. 35 is a perspective view of an ultrasonic surgical instrument configured in a D31 transducer architecture comprising separate ultrasonic waveguide and ultrasonic transducer base plate components shown in a coupled configuration, according to one aspect of this disclosure.
Figure 36:
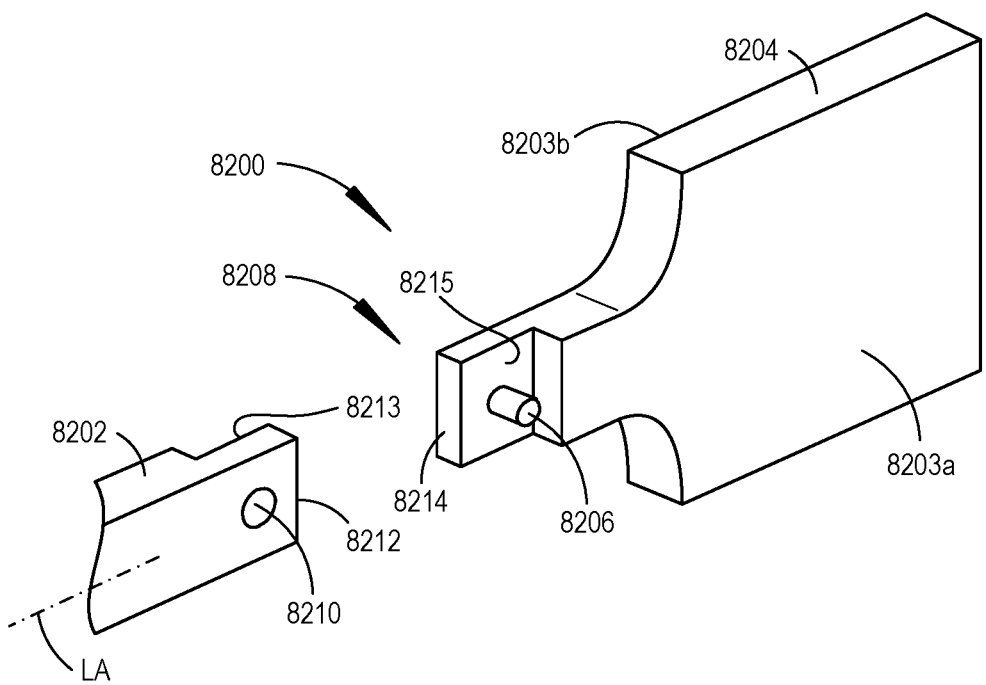
FIG. 36 is an exploded view of the ultrasonic surgical instrument shown in FIG. 35, according to one aspect of this disclosure.

FIG. 35 is a perspective view of an ultrasonic surgical instrument 8200 configured in a D31 transducer architecture comprising separate ultrasonic waveguide 8202 and ultrasonic transducer base plate 8204 (e.g., a transducer mounting portion) components shown in a coupled configuration, according to one aspect of this disclosure. FIG. 36 is an exploded view of the ultrasonic surgical instrument 8200 shown in FIG. 35, according to one aspect of this disclosure. With reference to FIGS. 35 and 36, the waveguide 8202 is attached to the transducer base plate 8204 by an interference flange joint 8208. The transducer base plate 8204 defines flat faces 8203*a*, 8203*b* on opposite sides of the transducer base plate 8204 suitable to attach and support a PZT piezoelectric element on each flat face 8203*a*, 8203*b* similar to the D31 configuration shown by way of example in FIG. 3.

The ultrasonic surgical instrument 8200 may comprise multiple pieces to reduce material waste and provide the ability to use alternate materials and/or manufacturing methods for the waveguide 8202 and the transducer base plate 8204. In one aspect, the waveguide 8202 and the transducer base plate 8204 are made separately from flat metal stock. The metal for both components is suitable for transmitting ultrasonic vibrations and may be titanium, titanium alloy, aluminum, or aluminum alloy, for example, as described herein. For example, the waveguide 8202 may be made of titanium or titanium alloy and the transducer base plate 8204 may be made of aluminum or aluminum alloy and joined by the interference flange joint 8208. This configuration enables the waveguide 8202 or transducer base plate 8204 to be replaced in the field. The transducer base plate 8204 can be made of aluminum or other suitable metal material. This is advantageous in terms of low cost, availability, ease of machining, and thermal conductivity for the heat management of the piezoelectric elements. The waveguide 8292 and the transducer base plate 8204 can be made of the same material or different materials suitable for transmitting ultrasonic energy along the longitudinal axis LA.

As shown in FIGS. 35 and 36, the distal end of the waveguide 8202 defines a blade 8216 for treating tissue and a proximal end of the waveguide 8202 defines a flange 8212 that is complementary and mates with a flange 8214 defined at the distal end of the transducer base plate 8204. The waveguide flange 8212 defines an aperture 8210 sized and configured to receive a pin 8206 defined by the transducer base plate flange 8214 sized and configured to achieve an interference flange joint 8208 between the waveguide 8202 and the transducer base plate 8204. In the illustrated example, the transducer base plate 8204 includes an integral machined pin 8206. The waveguide flange 8212 defines a recessed area 8213 that mates with a recessed area 8215 defined by the transducer base plate flange 8214.

Figure 37:
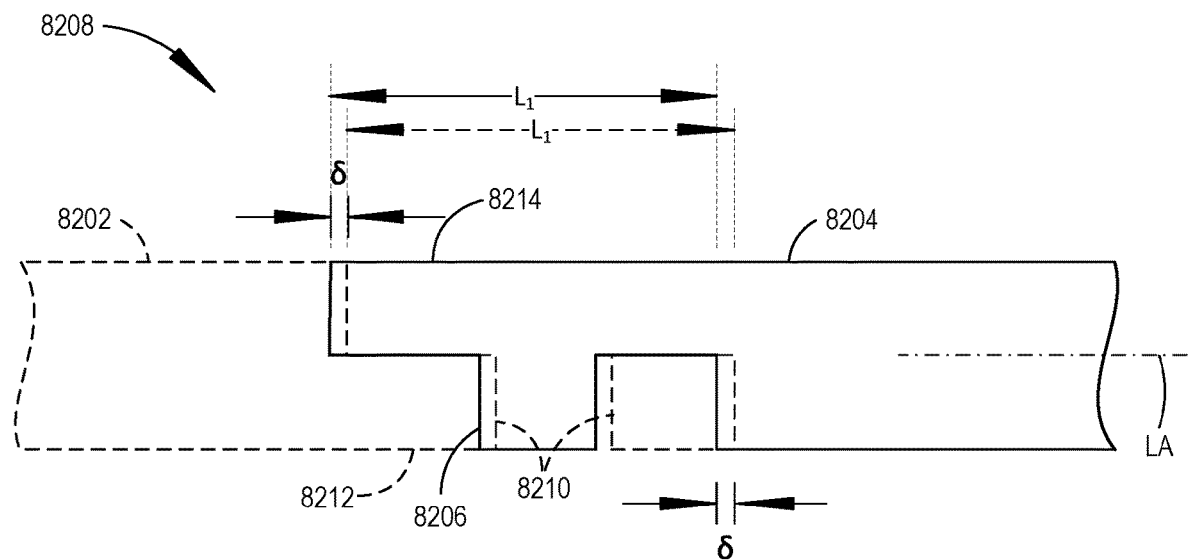
FIG. 37 illustrates the waveguide flange, shown in dashed line form, and the transducer base plate flange, shown in solid line form, superimposed in a decoupled configuration, according to one aspect of this disclosure.

FIG. 37 illustrates the waveguide flange 8212, shown in dashed line form, and the transducer base plate flange 8214, shown in solid line form, superimposed in a decoupled configuration, according to one aspect of this disclosure. At room temperature prior to assembly, the length of the waveguide flange 8212 and the transducer base plate flange 8214 is $L_1$. In this arrangement, at room temperature, the length $L_1$ of the flanges 8212, 8214 is slightly longer than the recessed area 8213, 8215 in the mating component, depicted by δ in FIG. 37. Additionally, the aperture 8210 defined by the waveguide flange 8212 is slightly offset on the waveguide flange 8212 such that at room temperature the waveguide 8202 and the transducer base plate 8204 cannot be seated together due to inadequate axial clearance between the pin 8206 and the recess area 8215 in the transducer base plate flange 8214.

Figure 38:
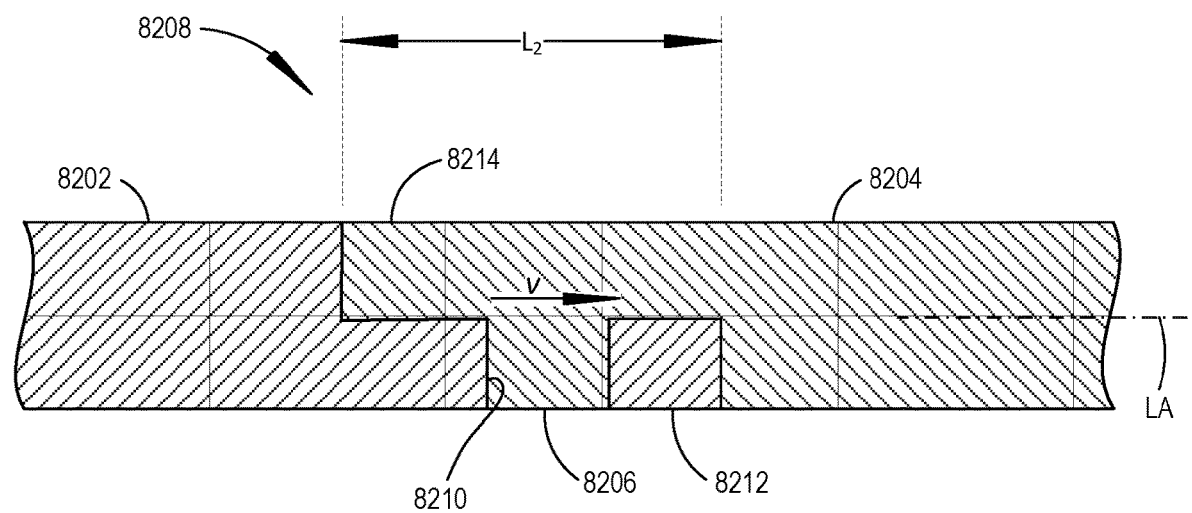
FIG. 38 illustrates the waveguide and the transducer base plate in a coupled configuration, according to one aspect of this disclosure.

FIG. 38 illustrates the waveguide 8202 and the transducer base plate 8204 in a coupled configuration, according to one aspect of this disclosure. To assemble the waveguide 8202 and the transducer base plate 8204, extreme cold is applied to both waveguide 8202 and transducer base plate 8204 components, thereby shrinking the axial extent of the corresponding flanges 8212, 8214. The waveguide 8202 and transducer base plate 8204 components are assembled under the cold condition, and when they return to room temperature or above, the flanges 82122, 8214, pin 8206, and aperture 8210 bind with each other. In the assembled state the length of the waveguide flange 8212 and the transducer base plate flange 8214 is $L_2$, where $L_2<L_1$. A nominal compressive load therefore exists in the parts at all times and a corresponding shear load, v, at the pin 8206, to achieve an interference flange joint 8208. The pin 8206 configuration accommodates this nominal shear load and for strength of the pin 8206, the transducer base plate 8204 component may be made of a metal that has higher strength than aluminum, such as titanium, for example. Nevertheless, an aluminum alloy may be employed to accommodate the shear force requirements of the pin 8206.

Figure 39:
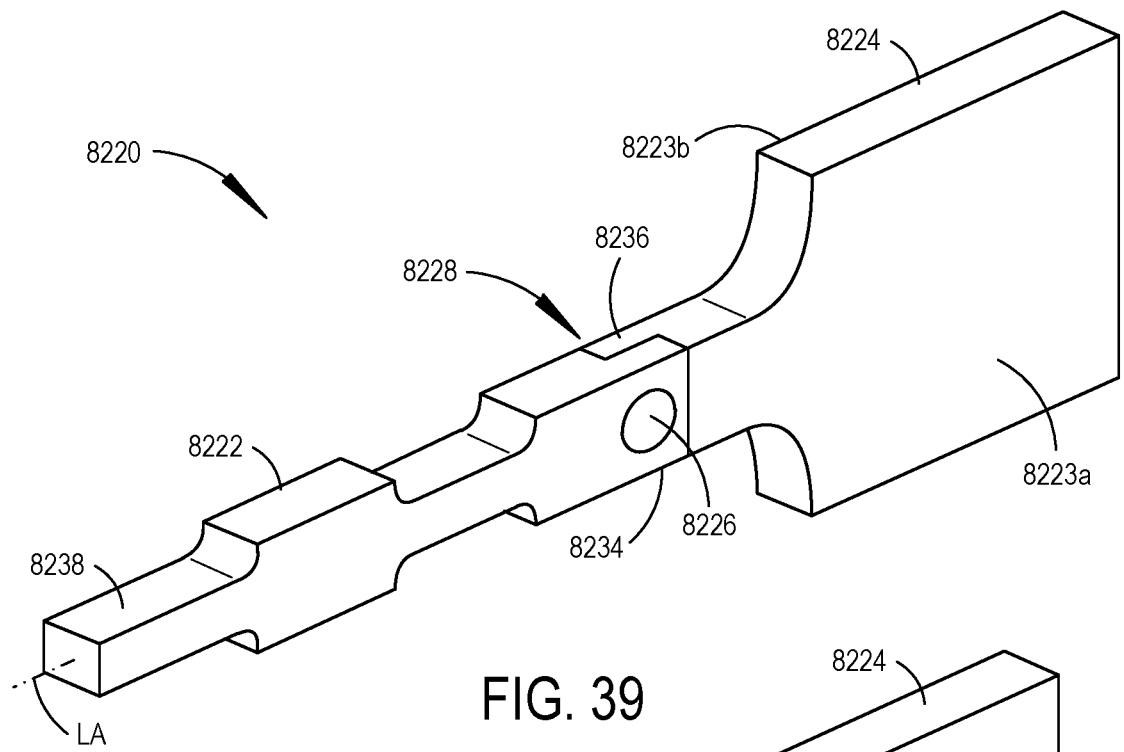
FIG. 39 is a perspective view of an ultrasonic surgical instrument configured in a D31 transducer architecture comprising separate ultrasonic waveguide and ultrasonic transducer base plate components shown in a coupled configuration, according to one aspect of this disclosure.
Figure 40:
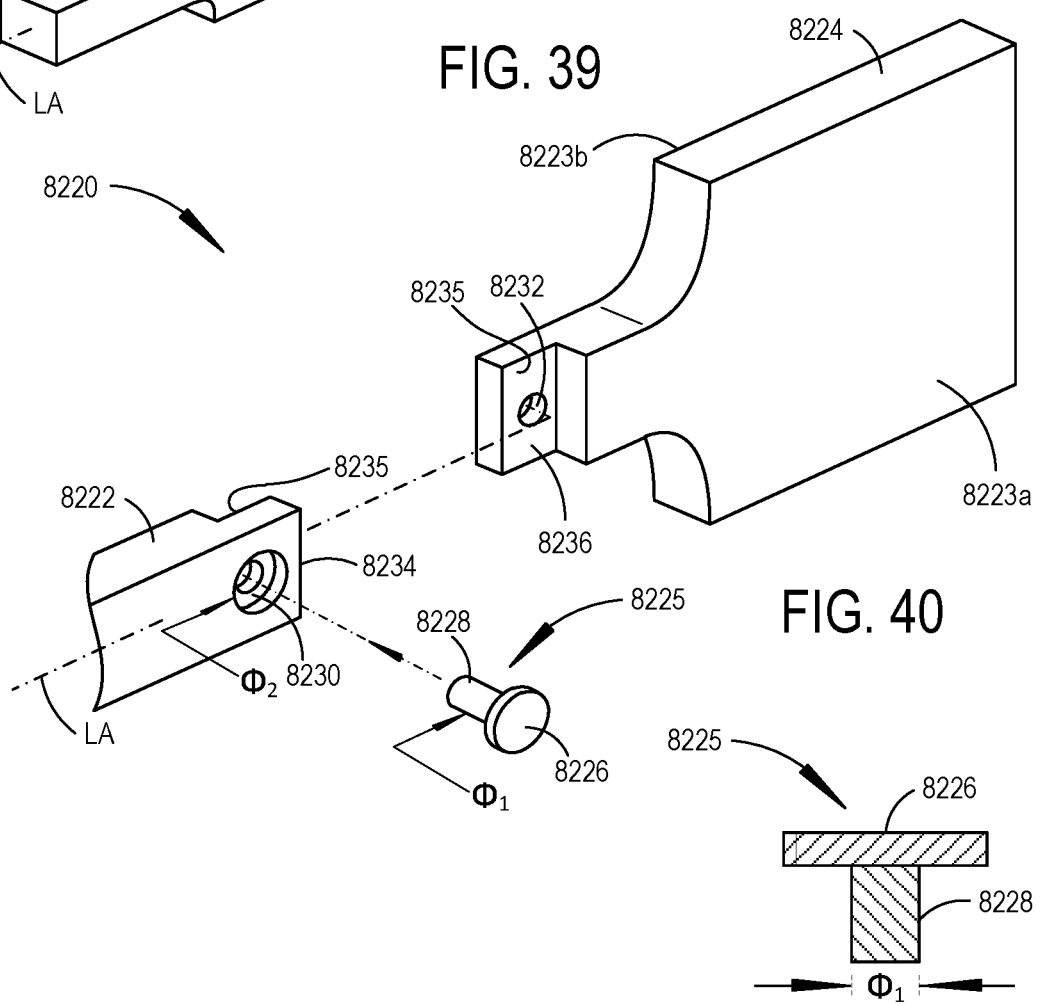
FIG. 40 is an exploded view of the ultrasonic surgical instrument shown in FIG. 39, according to one aspect of this disclosure.

FIG. 39 is a perspective view of an ultrasonic surgical instrument 8220 configured in a D31 transducer architecture comprising separate ultrasonic waveguide 8222 and ultrasonic transducer base plate 8224 (e.g., a transducer mounting portion) components shown in a coupled configuration, according to one aspect of this disclosure. FIG. 40 is an exploded view of the ultrasonic surgical instrument 8220 shown in FIG. 39, according to one aspect of this disclosure. With reference to FIGS. 39 and 40, the waveguide 8222 is attached to the transducer base plate 8224 by an interference pin joint 8228. The transducer base plate 8224 defines flat faces 8223*a*, 8223*b* on opposite sides of the transducer base plate 8224 suitable to attach and support a PZT piezoelectric element on each flat face 8223*a*, 8223*b* similar to the D31 configuration shown by way of example in FIG. 3.

The ultrasonic surgical instrument 8220 may comprise multiple pieces to reduce material waste and provide the ability to use alternate materials and/or manufacturing methods for the waveguide 8222 and the transducer base plate 8224. In one aspect, the waveguide 8222 and the transducer base plate 8224 are made separately from flat metal stock. The metal for both components is suitable for transmitting ultrasonic vibrations and may be titanium, titanium alloy, aluminum, or aluminum alloy, for example, as described herein. For example, the waveguide 8222 may be made of titanium or titanium alloy and the transducer base plate 8224 may be made of aluminum or aluminum alloy and joined by the interference pin joint 8228. This configuration enables the waveguide 8222 or transducer base plate 8224 to be replaced in the field. The transducer base plate 8224 can be made of aluminum or other suitable metal material. This is advantageous in terms of low cost, availability, ease of machining, and thermal conductivity for the heat management of the piezoelectric elements. The waveguide 8222 and the transducer base plate 8224 can be made of the same material or different materials suitable for transmitting ultrasonic energy along the longitudinal axis LA.

As shown in FIGS. 39 and 40, the distal end of the waveguide 8222 defines a blade 8238 for treating tissue and a proximal end of the waveguide 8222 defines a flange 8234 that matches a flange 8236 defined at the distal end of the transducer base plate 8224. The waveguide flange 8234 defines an aperture 8230 sized and configured to receive a shaft 8228 of a pin 8225, shown in section view in FIG. 41, sized and configured to achieve an interference pin joint 8228 between the waveguide 8222 and the transducer base plate 8224. The aperture 8230 includes a counter bore to accommodate the head 8226 of the pin 8225. In the illustrated example, the transducer base plate 8224 also includes an aperture 8232 sized and configured to receive the shaft 8228 of the pin 8225. The waveguide flange 8212 defines a recessed area 8213 that mates with a recessed area 8215 defined by the transducer base plate flange 8214. The pin 8225 may be made of steel or other metal having high shear strength.

Figure 41:
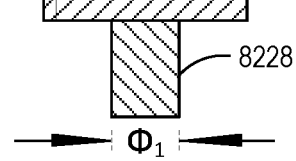
FIG. 41 is a section view of a pin, according to one aspect of this disclosure.

With reference to FIGS. 39-41, joining the dissimilar materials and components of the waveguide 8222 and the transducer base plate 8224 in a D31 configuration is achieved using an interference fit pin joint 8228. The diameter $\Phi_1$ of the shaft 8228 of the joint pin 8225 at very low temperature equals the diameter $\Phi_2$ of both apertures 8230, 8232 in the waveguide 8222 and the transducer base plate 8224 when these components are at high temperature. Assembly of the waveguide 8222 and the transducer base plate 8224 is performed under this thermal mismatch condition and when the waveguide 8222 and transducer base plate 8224 components cool/warm to a uniform temperature, the pin 8225 achieves an interference fit joint 8228 and joins both the waveguide 8222 and the transducer base plate 8224. The interference fit joint 8228 at the pin 8225 creates the continuity of material required to transfer the ultrasonic vibrations along the longitudinal axis LA from the transducer base plate 8224 through the waveguide 8222 to the blade 8238.

Figure 42:
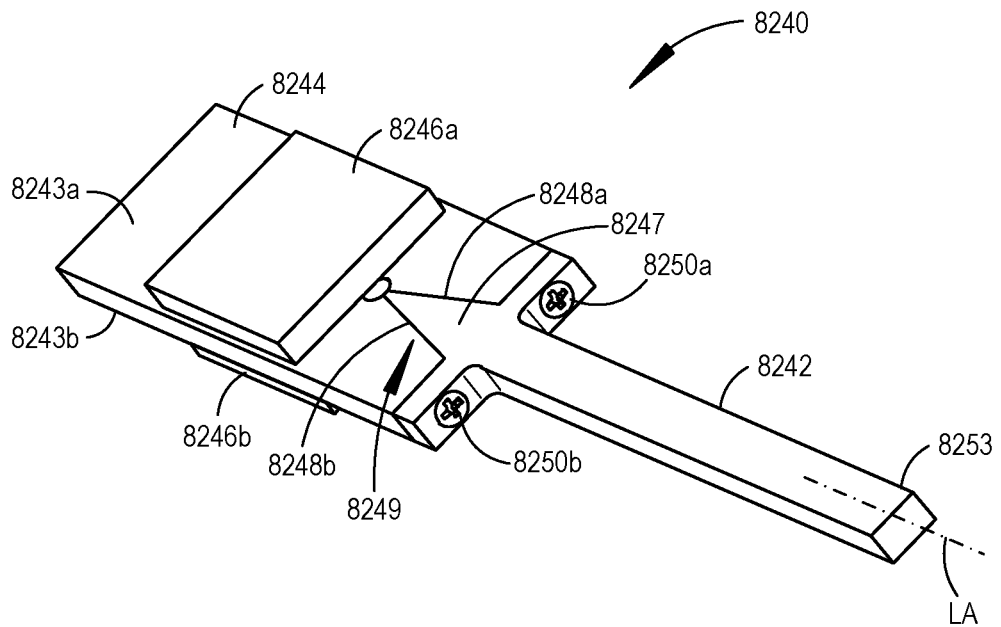
FIG. 42 is a perspective view of an ultrasonic surgical instrument configured in a D31 transducer architecture comprising separate ultrasonic waveguide and ultrasonic transducer base plate components shown in a coupled configuration, according to one aspect of this disclosure.
Figure 43:
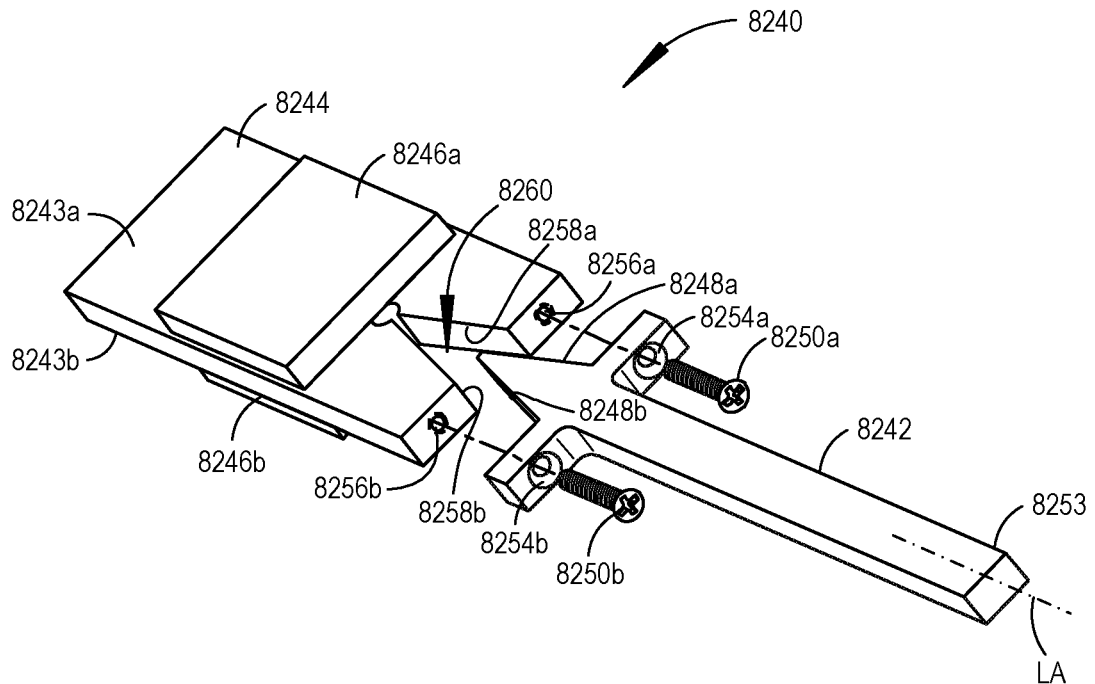
FIG. 43 is an exploded view of the ultrasonic surgical instrument shown in FIG. 42, according to one aspect of this disclosure.

FIG. 42 is a perspective view of an ultrasonic surgical instrument 8240 configured in a D31 transducer architecture comprising separate ultrasonic waveguide 8242 and ultrasonic transducer base plate 8244 (e.g., a transducer mounting portion) components shown in a coupled configuration, according to one aspect of this disclosure. FIG. 43 is an exploded view of the ultrasonic surgical instrument 8240 shown in FIG. 42, according to one aspect of this disclosure. With reference to FIGS. 42 and 43, the waveguide 8242 is attached to the transducer base plate 8244 by a wedge joint 8249. The ultrasonic surgical instrument 8240 may comprise multiple pieces to reduce material waste and provide the ability to use alternate materials and/or manufacturing methods for the waveguide 8242 and the transducer base plate 8244. In one aspect, the waveguide 8242 and the transducer base plate 8244 are made separately from flat metal stock. The metal for both components is suitable for transmitting ultrasonic vibrations and may be titanium, titanium alloy, aluminum, or aluminum alloy, for example, as described herein. For example, the waveguide 8242 and the transducer base plate 8244 are two separate pieces joined by a wedge joint 8249. This configuration enables the waveguide 8242 or transducer base plate 8244 to be replaced in the field. The transducer base plate 8244 defines flat faces 8243*a*, 8243*b* on opposite sides of the transducer base plate 8244 suitable to attach and support a PZT piezoelectric element 8246*a*, 8246*b* on each flat face 8243*a*, 8243*b* similar to the D31 configuration shown by way of example in FIG. 3. The transducer base plate 8244 can be made of aluminum. This is advantageous in terms of low cost, availability, ease of machining, and thermal conductivity for the heat management of the piezoelectric elements 8246*a*, 8246*b*. The waveguide 8242 and the transducer base plate 8244 can be made of the same material or different materials suitable for transmitting ultrasonic energy along the longitudinal axis LA.

As shown in FIGS. 42 and 43, the distal end of the waveguide 8242 defines a blade 8253 for treating tissue and a proximal end of the waveguide 8242 defines a wedge 8247 feature that matches a notch 8260 in the distal end of the transducer base plate 8244. The wedge 8247 defines two tapered sidewalls 8248*a*, 8248*b* that match tapered sidewalls 8258*a*, 8258*b* that define the notch 8260. The waveguide 8242 is bolted to the transducer base plate 8244 by two screws 8250*a*, 8250*b* that are received through countersunk apertures 8254*a*, 8254*b* defined by flanges laterally disposed from the wedge 8247 feature defined by the proximal end of the waveguide 8244. The screws 8250*a*, 8250*b* are threadably fastened to the transducer base plate 8244 via threaded apertures 8256*a*, 8256*b*. In use, the ultrasonic vibrational movement is transmitted along the longitudinal axis LA from the transducer base late 8244 through the waveguide 8242 to the blade 8253 through the surfaces 8248*a*, 8248*b*, 8258*a*, 8258*b* of the wedge 8247 and notch 8260. The angle of the wedge 8247 and notch 8260 may be selected such that the compression on their surfaces 8248*a*, 8248*b*, 8258*a*, 8258*b* in contact is high, while the screws 8250*a*, 8250*b* are exposed to a low stress, so they can be small.

Figure 44:
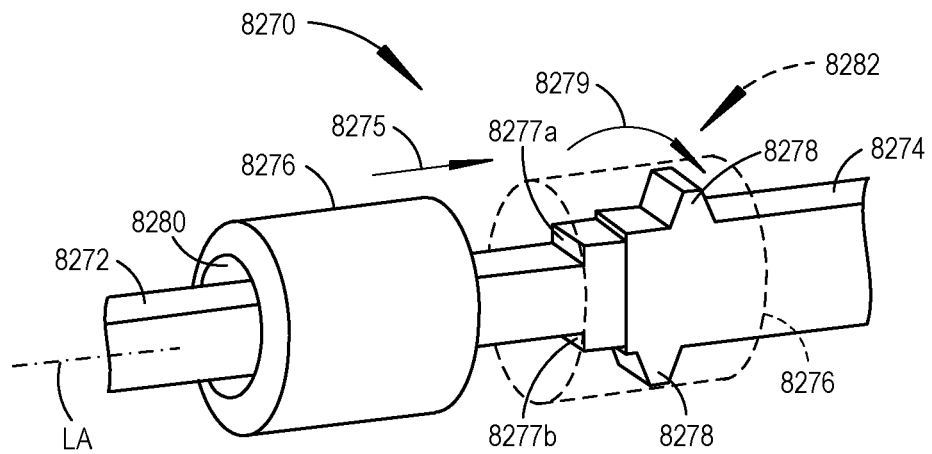
FIG. 44 is a perspective view of a luer lock joint suitable for coupling ultrasonic waveguide and ultrasonic transducer base plate components of a two-piece ultrasonic surgical instrument, according to one aspect of this disclosure.
Figure 45:
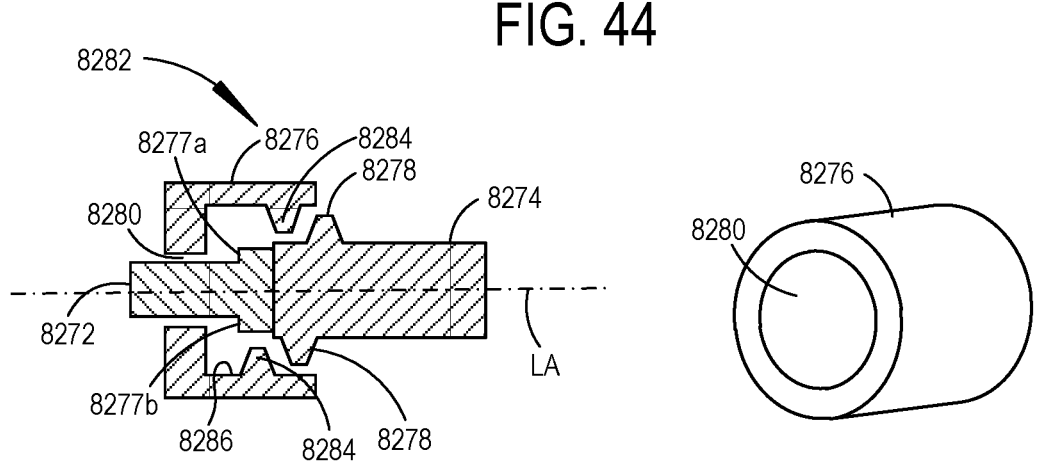
FIG. 45 is a section view of the luer lock joint in a coupled configuration, according to one aspect of this disclosure.
Figure 46:
FIG. 46 is a luer nut component of the luer lock joint shown in FIG. 44, according to one aspect of this disclosure.
Figure 47:
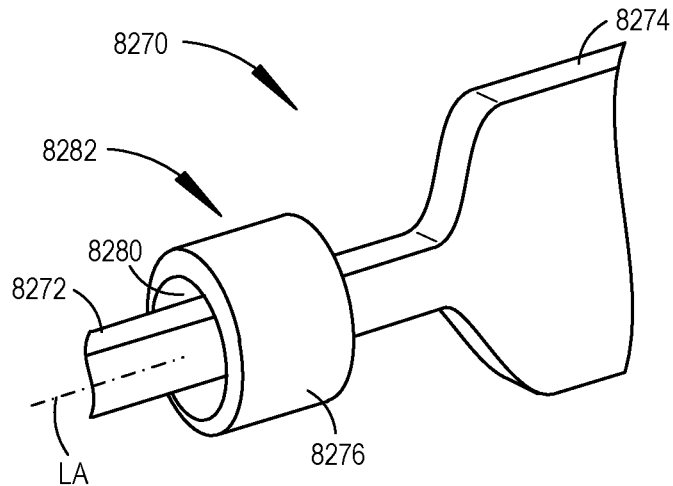
FIG. 47 is perspective view of the luer lock joint shown in FIG. 44 in a coupled configuration, according to one aspect of this disclosure.

FIG. 44 is a perspective view of a luer lock joint 8282 suitable for coupling ultrasonic waveguide 8272 and ultrasonic transducer base plate 8274 (e.g., a transducer mounting portion) components of a two-piece ultrasonic surgical instrument 8270, according to one aspect of this disclosure. FIG. 45 is a section view of the luer lock joint 8282 in a coupled configuration, according to one aspect of this disclosure. FIG. 46 is a luer nut 8276 component of the luer lock joint shown in FIG. 44 and FIG. 47 is perspective view of the luer lock joint 8282 shown in FIG. 44 in a coupled configuration, according to one aspect of this disclosure.

With reference to FIGS. 44-47, the waveguide 8272 is attached to the transducer base plate 8274 by luer lock joint 8282. The ultrasonic surgical instrument 8270 may comprise multiple pieces to reduce material waste and provide the ability to use alternate materials and/or manufacturing methods for the waveguide 8272 and the transducer base plate 8274. In one aspect, the waveguide 8272 and the transducer base plate 8274 are made separately from flat metal stock. The metal for both components is suitable for transmitting ultrasonic vibrations and may be titanium, titanium alloy, aluminum, or aluminum alloy, for example, as described herein. For example, the waveguide 8272 and the transducer base plate 8274 are two separate pieces joined by a luer lock joint 8282. This configuration enables the waveguide 8272 or transducer base plate 8274 to be replaced in the field. Although not shown, the transducer base plate 8274 defines flat faces on opposite sides of the transducer base plate suitable to attach and support a PZT piezoelectric element on each flat face similar to the D31 configuration shown by way of example in FIG. 3. The transducer base plate 8274 can be made of aluminum. This is advantageous in terms of low cost, availability, ease of machining, and thermal conductivity for the heat management of the piezoelectric elements. The waveguide 8272 and the transducer base plate 8274 can be made of the same material or different materials suitable for transmitting ultrasonic energy along the longitudinal axis LA.

With reference now particularly to FIGS. 44 and 45, the luer nut 8276 defines an interior region 8280 to slidably engage the waveguide 8272. As the luer nut 8276 is retracted 8275 proximally the luer nut 8276 (shown in dashed line form) engages male luer lock threads 8278 defined at a distal end of the transducer base plate 8274. Applying a clockwise rotation 8279 causes the threads 8284 defined by a cylindrical sidewall 8286 of the luer nut 8276. Base wall portions 8277a, 8277b act as a stop for the luer nut 8276. Either the transducer base plate 8274 or the waveguide 8272 may have a luer like male thread 8278 made into its shape. In the illustrated example, a half turn luer nut 8276 fits over the waveguide 8272 and screws into the transducer base plate 8274 to lock the two components together. The luer lock thread 8278 is two-dimensional on the screw side at the distal end of the transducer base plate 8274 and is compatible for use with simple shapes like a flat waveguide 8272, for example.

The following description is directed to techniques for manufacturing three-piece ultrasonic surgical instruments. In one aspect, the ultrasonic surgical instrument comprises an ultrasonic transducer base plate, an ultrasonic waveguide shaft, and an ultrasonic transducer. The transducer base plate may be coupled the waveguide shaft by the techniques described herein in connection with FIGS. 4-47, for example. The waveguide shaft may be coupled to the ultrasonic blade by swaging the two components. It will be appreciated that swaging is a forging process in which the dimensions of an item are altered using dies into which the item is forced. Although swaging is usually a cold working process, it also may be hot worked. The term swage may apply to the process or a die or tool used in the process. In one aspect, the swaging process may be employed to join the transducer base plate and the waveguide shaft. Generally, the transducer base plate, waveguide shaft, and ultrasonic blade may be made from dissimilar metals that are suitable for transmitting ultrasonic vibrations along a longitudinal axis. For example, the swaging process may be employed to join aluminum (or alloys thereof) ultrasonic transducer base plates to titanium (or alloys thereof) ultrasonic waveguides. Additionally, the swaging process may be employed to join aluminum waveguides to titanium (or alloys thereof) ultrasonic blades. The following description provides configurations, tooling, and processes suitable for swaging certain aluminum ultrasonic waveguide shafts to certain titanium ultrasonic blades.

Biomedical titanium alloys such as wrought Ti-6Al-4V alloy of extra low interstitial (ELI) grade has been used in the biomedical applications because of its high strength-to-weight ratio and excellent biocompatibility. ELI is the only readily available practical material known to date that has both enough hardness and high enough Q (Resonance Loss Factor Value) to be functionally suitable for use in the ultrasonic medical devices as both an ultrasonic blade and an ultrasonic acoustical waveguide system, i.e., transmitting ultrasonic energy as a transducer core. Wrought Ti-6Al-4V alloy, however, is a relatively expensive material to produce; both in the raw foundry wrought material and followed by machining into a functional part, versus machined wrought Al 6061-T6 or Al7075-T6 alloys, which because they are less hard are less suitable for maintaining the robust surgical ultrasonic blade edge of the medical device. Wrought Al 6061-T6 or Al7075-T6 alloys, however, do have suitable ultrasonic energy transmission properties nearly identical to Ti-6Al-4V ELI alloy at less than half the material and production costs of the one-piece wrought Ti-6Al-4V ELI alloy based ultrasonic medical device.

FIG. 48 is a perspective view of an ultrasonic waveguide 8300 for an ultrasonic surgical instrument comprising an ultrasonic waveguide shaft 8302 made of one metal and coupled to an ultrasonic blade 8306 made of a dissimilar metal, according to aspect of this disclosure. The waveguide shaft 8302 includes a coupler 8304 at a proximal end to increase retention and reduce rotation between the distal tip of the ultrasonic waveguide 8300 and the waveguide shaft 8302. An ultrasonic blade 8306 is coupled to a distal end of the waveguide shaft 8302 at a swaged joint 8309. The proximal end of the ultrasonic blade 8306 includes a cylindrical wall 8309 sized and configured to receive a distal end of the waveguide shaft 8302 for the swaging process. In one aspect the waveguide shaft 8302 may be made of wrought Al 6061-T6 or Al7075-T6 aluminum alloys and the ultrasonic blade 8306 may be made of wrought Ti-6Al-4V ELI titanium alloy.

FIG. 49 is a magnified view of the coupler 8304, according to one aspect of this disclosure. The coupler 8304 comprises a retention feature 8318 in the form of a longitudinal groove to increase retention and reduce rotation between the blade 8306 and the waveguide shaft 8302. The coupler 8304 further comprises cylindrical walls 8312, 8316 and annular grooves 8313, 8314 to couple the waveguide shaft 8302 to an ultrasonic base plate as described herein in connection with FIGS. 4-47, for example. The coupler 8304 may be formed integrally with or coupled to the waveguide shaft 8302. A cylindrical wall 8310 is sized and configured to receive the distal end of the coupler 8304.

Presented here is a unique permanent mechanical swaged joint 8309 design and warm draw die swaging process to achieve a reliable robust mechanical swaged joint 8309 between the ultrasonic waveguide shaft 8302 and the ultrasonic blade 8306 that maintains a desirable elastic acoustic wrought microcrystalline grain structure of both the titanium and aluminum alloy materials that are efficient in transmitting ultrasonic energy with minimal to no loss due to the swaged joint 8309 formed between the two materials, and is as acceptably functional as an titanium alloy (e.g., Ti-6Al-4V ELI titanium alloy) ultrasonic medical device.

This configuration provides an ultrasonic waveguide 8300 at about half the cost to manufacture relative to an all titanium alloy (e.g., Ti-6Al-4V ELI titanium alloy) ultrasonic medical device. Other welding joining processes such as solid state, friction, inertia, ultrasonic, electron beam and laser welding between the aluminum waveguide shaft 8302 and the titanium blade 8306 where tried but did not produce acceptable joints of sufficient functional strength to transmit the required ultrasonic energy without joint failure. Also within the weld zone the material microstructure is changed from wrought (acceptable high Q) to annealed (less than desirable low Q) resulting in local damping of the ultrasonic wave within the waveguide 8300.

Figure 50:
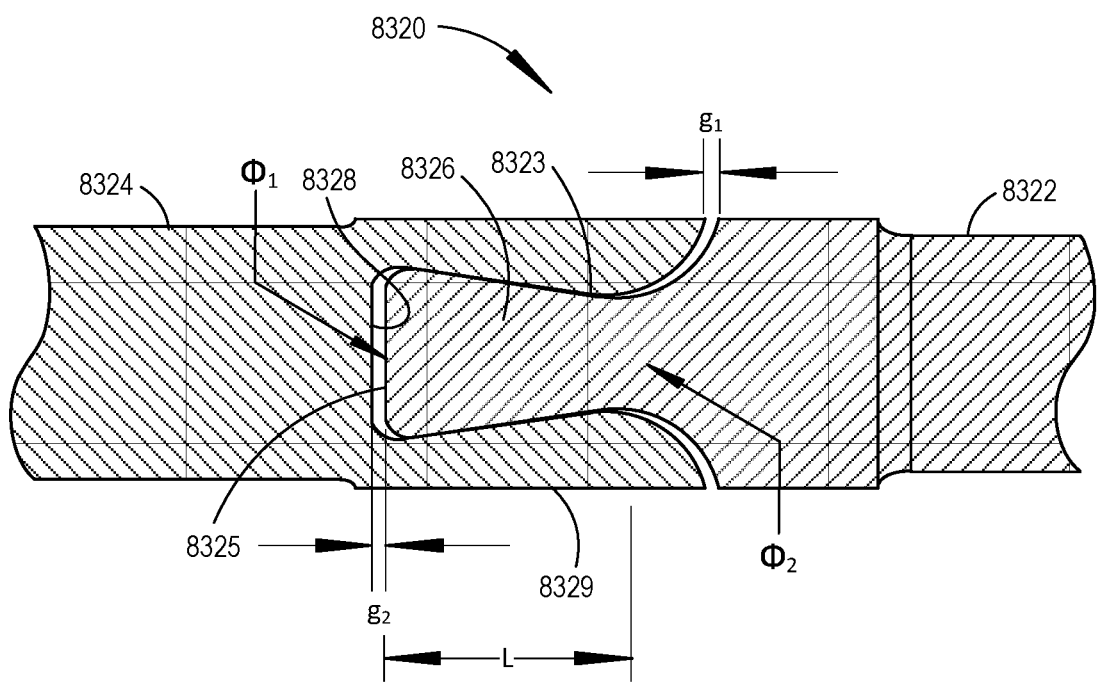
FIG. 50 is a section view of a swaged joint between a two-piece ultrasonic tool comprising an ultrasonic waveguide shaft made of one metal and an ultrasonic blade made of a different metal, according to one aspect of his disclosure.

FIG. 50 is a section view of a swaged joint 8320 between a two-piece ultrasonic tool comprising an ultrasonic waveguide shaft 8324 made of one metal and an ultrasonic blade 8322 made of a different metal, according to one aspect of his disclosure. Prior to applying the swaging process, the waveguide shaft 8324 defines a cylindrical aperture with a flat perpendicular bottom 8328. The ultrasonic blade 8322 includes a conical male end 8326 defining a conic taper 8323 that is received into the cylindrical aperture defined by the waveguide shaft 8324. The proximal end of the conical male end 8326 defines a flat perpendicular bottom 8325 that should abut the flat perpendicular bottom 8328 defined by the waveguide shaft 8324. After the conical male end 8326 is inserted into the cylindrical aperture defined by the waveguide shaft 8324 the swaging process is applied to produce the swaged joint 8320 shown in FIG. 50.

The swaged joint 8320 is achieved by joining the proximal end of the ultrasonic blade 8322 having a male end 8326 defining a conical shape into the cylindrical aperture defined by the distal end of the waveguide shaft 8324. The length L of conical male end 8326 of the blade 8322 is approximately twice the length of the major diameter $\Phi_1$ of the male end 8326 of the ultrasonic blade 8322 and has a conic taper 8323 of 2°-6° to the minor diameter $\Phi_2$. The conical shape male end 8326 defines a flat perpendicular proximal bottom 8325. In one aspect, the ultrasonic blade 8322 is made of a Ti-6Al-4V ELI titanium alloy and the waveguide shaft 8324 is made of Al 6061-T6 or Al7075-T6 aluminum alloys. The conical shape male end 8326 is located on the proximal end of the Ti-6Al-4V ELI titanium alloy blade 8322 component and fits into the blind cylindrical aperture defined by the Al 6061-T6 or Al7075-T6 aluminum alloy waveguide shaft 8324 component. The blind cylindrical aperture in the waveguide shaft 8324 defines a flat, perpendicular bottom 8328 and is the same diameter $\Phi_1$ as the conical male end 8326 of the blade 8322. A collar 8329 (also see collar 8308 in FIG. 49) of additional material is provided around the outside diameter of the blind cylindrical aperture such that there is additional material (2°-6°) to flow plastically around the shape of the conical male end 8326 during the swaging process, filling the void and resulting in a retained linear compression between the flat bottom 8325 of the conical male end 8326 and the flat bottom 8328 of the blind cylindrical aperture of the waveguide shaft 8324, as well as around the conical male end 8326. The swaged joint 8320 shown in FIG. 50, however, defines gaps $g_1$ and $g_2$, which leads to lower performance. The aspect illustrated in FIG. 51 removes the gaps $g_1$ and $g_2$ during the swaging process.

Figure 51:
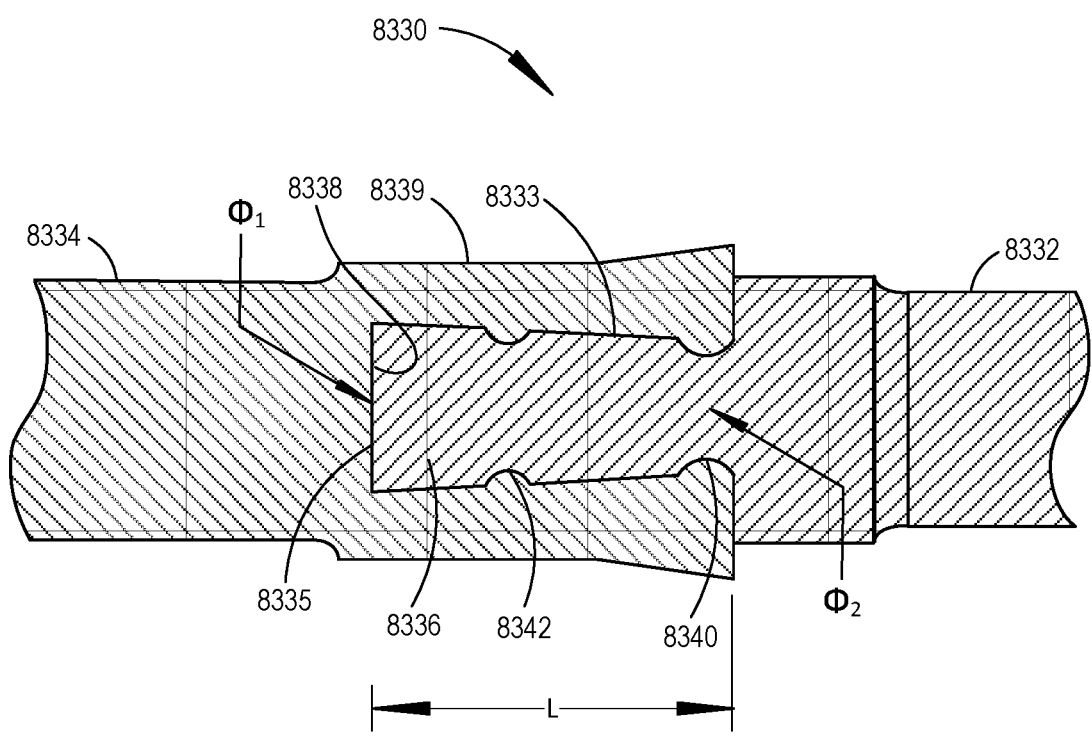
FIG. 51 is a section view of a swaged joint achieved between a two-piece ultrasonic waveguide comprising an ultrasonic waveguide shaft made of one metal and an ultrasonic blade made of a different metal, according to one aspect of his disclosure.
Figure 52:
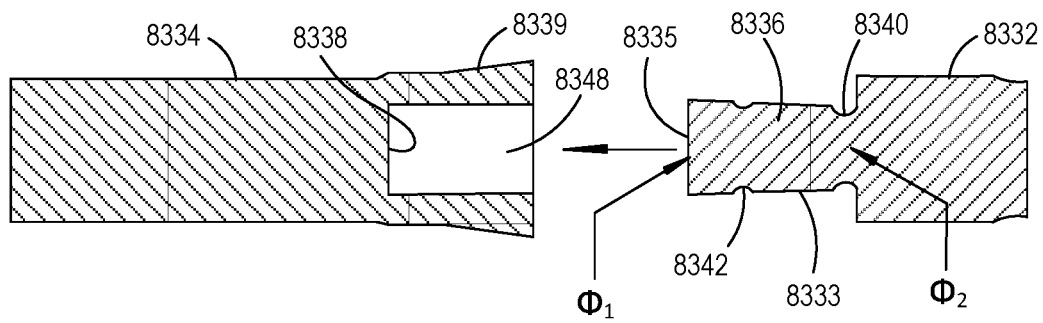
FIGS. 52-55 show the steps for producing the swaged joint shown in FIG. 51, according to one aspect of this disclosure.
Figure 53:
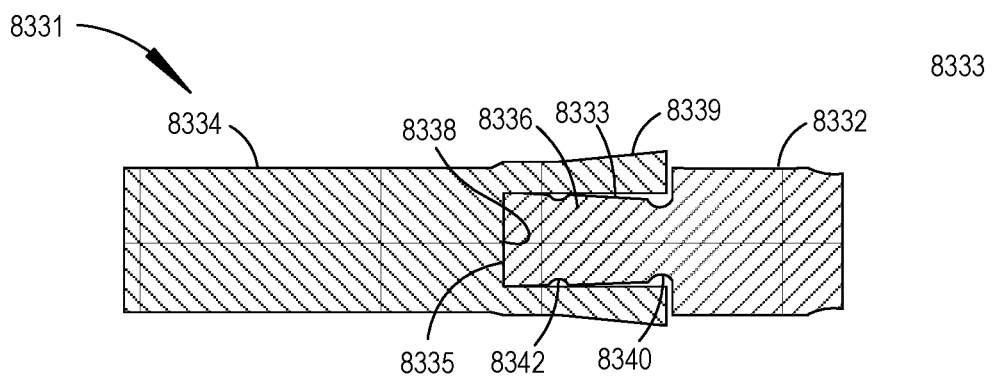
Figure 54:
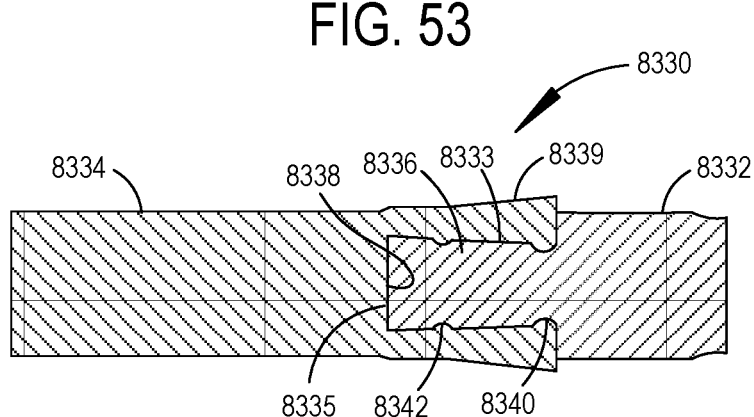
Figure 55:
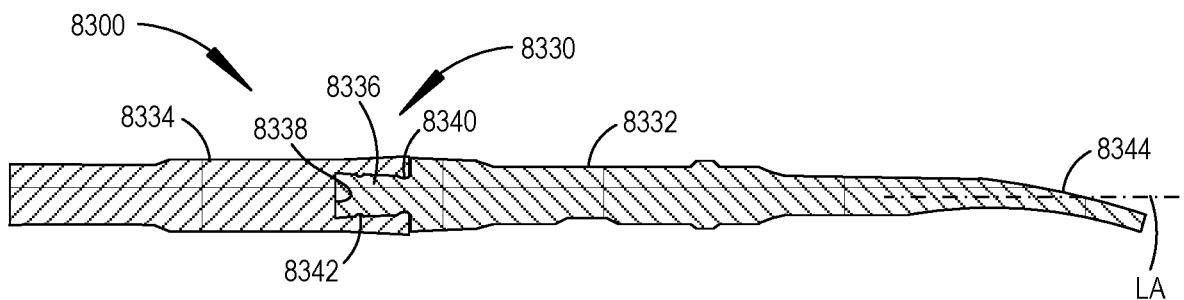

FIG. 51 is a section view of a swaged joint 8330 achieved between a two-piece ultrasonic waveguide 8300 (FIGS. 48, 49, 55) comprising an ultrasonic waveguide shaft 8334 made of one metal and an ultrasonic blade 8332 made of a different metal, according to one aspect of his disclosure. FIGS. 52-55 show the steps for producing the swaged joint 8330 shown in FIG. 51, according to one aspect of this disclosure, where FIG. 52 is a section view of the waveguide shaft 8334 and the ultrasonic blade 8334 in a decoupled configuration, FIG. 53 is a section view of a pre-assembly 8331 of the waveguide shaft 8334 and the ultrasonic blade 8334 in a coupled configuration prior to applying the swaging process, FIG. 54 is a section view of the waveguide shaft 8334 and the ultrasonic blade 8334 in a coupled after the application of the swaging process, and FIG. 55 is a section view of joined ultrasonic waveguide 8300 showing the waveguide shaft 8334 coupled to the ultrasonic blade 8332, according to one aspect of this disclosure. The ultrasonic blade 8332 comprises a tissue treatment portion 8344 located at a distal end of the ultrasonic blade 8332, which is used to effect tissue in contact therewith.

With reference now to FIGS. 51-55 Prior to applying the swaging process, the waveguide shaft 8334 defines a cylindrical aperture 8348 with a flat perpendicular bottom 8338. The ultrasonic blade 8332 includes a male end 8336 defining a conical shape defining a conic taper 8333 that is received into the cylindrical aperture 8348 defined by the waveguide shaft 8334. The proximal end of the conical male end 8336 defines a flat perpendicular bottom 8335 that should abut the flat perpendicular bottom 8338 defined by the waveguide shaft 8334. After the conical male end 8336 is inserted into the cylindrical aperture 8348 defined by the waveguide shaft 8334 the swaging process is applied to produce the swaged joint 8330 shown in FIG. 51. Two circumferential grooves 8340, 8342 are defined about the conical male end 8336 of the blade 8332, one groove 8340 located near or at the smallest diameter $\Phi_2$ and one groove 8342 located between the smallest $\Phi_2$ and largest $\Phi_1$ diameters of the conical male end 8336 of the ultrasonic blade 8332. In one aspect, the one groove 8342 is located mid-way between the smallest $\Phi_2$ and largest $\Phi_1$ diameters of the conical male end 8336. In one aspect, the ultrasonic blade 8322 is made of a Ti-6Al-4V ELI titanium alloy and the waveguide shaft 8324 is made of Al 6061-T6 or Al7075-T6 aluminum alloys. The circumferential grooves 8340, 8342 define a space for the waveguide shaft 8334 material to flow during the swaging process to eliminate the gaps $g_1$, $g_2$ as shown in FIG. 50, thus improving performance loss and providing additional features to improve retention of the ultrasonic blade 8322 component in the waveguide shaft 8334 component.

Other features of the conical male end 836 of the ultrasonic blade 8332 are similar to the features described in connection with FIG. 50. For example, the swaged joint 8330 is achieved by joining the conical male end 8336 of the ultrasonic blade 8332 into the cylindrical aperture 8348 8 defined by the distal end of the waveguide shaft 8334. The length L of conical male end 8336 of the ultrasonic blade 8332 is approximately twice the length of the major diameter $\Phi_1$ of the conical male end 8336 of the ultrasonic blade 8332 and has a conic taper 8333 of 2°-6° to the minor diameter $\Phi_2$. The conical male end 8336 defines a flat perpendicular proximal bottom 8335. In one aspect, the conical male end 8336 is located on the proximal end of a Ti-6Al-4V ELI titanium alloy blade 8322 component and fits into the blind cylindrical aperture 8348 defined by an Al 6061-T6 or Al7075-T6 aluminum alloy waveguide shaft 8334 component. The blind cylindrical aperture 8348 in the waveguide shaft 8334 defines a flat, perpendicular bottom 8338 and is the same diameter $\Phi_1$ as the conical male end 8336 of the ultrasonic blade 8332. A collar 8339 (see also collar 8308 in FIG. 49) of additional material is provided about the outside diameter of the blind cylindrical aperture 8348 such that there is additional material (2°-6°) to flow plastically around the shape of the conical male end 8336 during the swaging process, and filling the void defined by the circumferential grooves 8340, 8342 resulting in a retained linear compression between the flat bottom 8335 of the conical male end 8336 and the flat bottom 8338 of the blind cylindrical aperture 8348 of the waveguide shaft 8334, as well as around the conical male end 8336.

Figure 57:
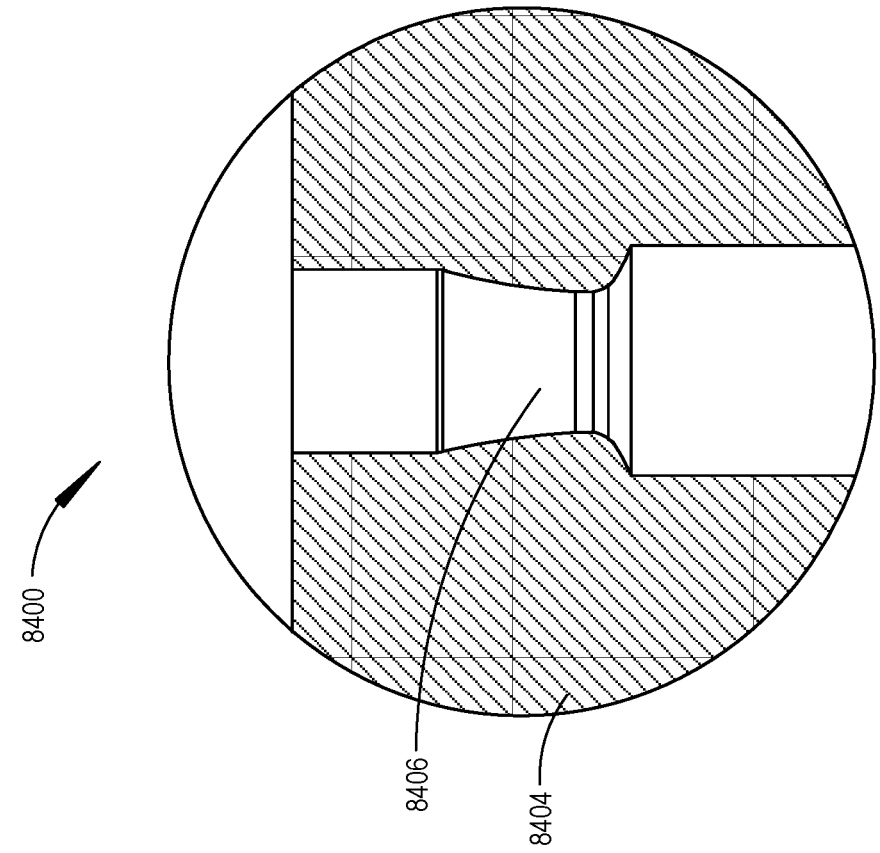
FIG. 57 is a detail section view of the draw die tool shown in FIG. 56, according to one aspect of this disclosure.
Figure 56:
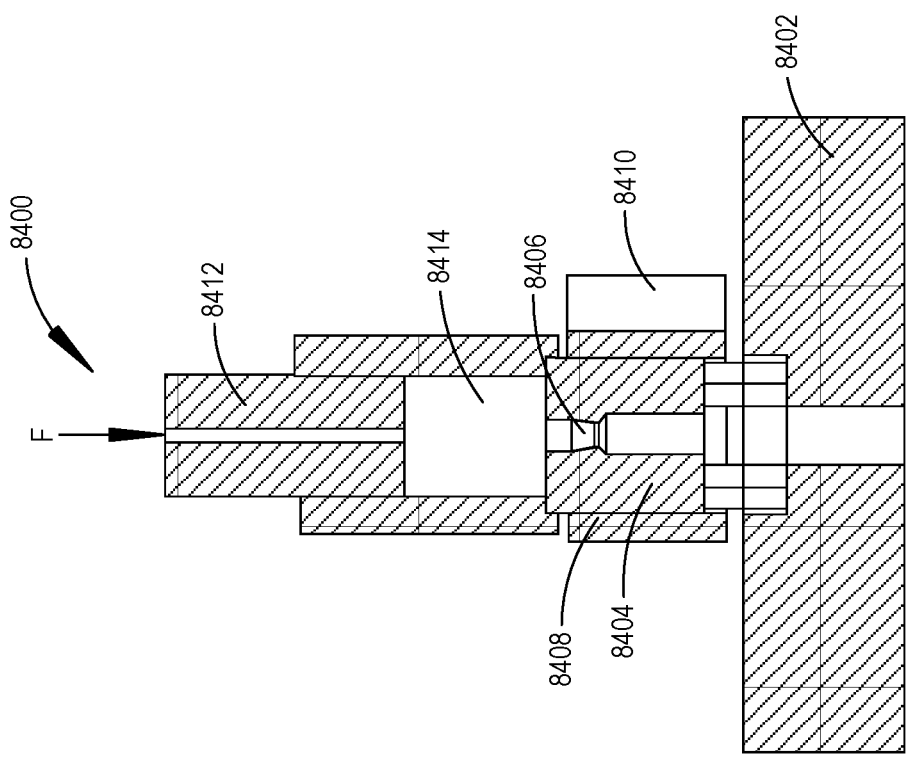
FIG. 56 is a section view of a heated draw die tool, according to one aspect of this disclosure.

The description now turns to a method of producing the ultrasonic waveguide 8300 by creating the swaged joint 8330 as discussed in connection with FIGS. 51-55 using a warm die swaging process, according to one aspect of this disclosure. FIG. 56 is a section view of a heated draw die tool 8400 and FIG. 57 is a detail section view of the draw die tool 8400 shown in FIG. 56, according to one aspect of this disclosure. With reference now to FIGS. 56 and 57, The heated draw die tool 8400 includes a base clamp 8402 to hold the pre-assembly 8331 (FIG. 53). A draw die 8404 is located above the base clamp 8402. The draw die 8404 defines an aperture 8406 to receive the pre-assembly 8331 (FIG. 53). A cylinder 8408 thermally coupled to a heating element 8410 surrounds the draw die 8404 to heat the draw die 8404. A circular die tool cylinder 8412 defines a sample chamber 8414. The distal end of the pre-assembly 8331 is located in the sample chamber 8414. A load F is applied to the circular die tool cylinder 8412 to press the pre-assembly 8331 through the draw die 8404.

With reference to FIGS. 52-57, the heated draw die process starts by inserting the pre-assembly 8331 through the heated draw die tool 8400, which incorporates mechanical position stops to accurately locate the pre-assembly 8331 with linear straightness respect to each other and in alignment with the location of the draw die 8404. The circular die tool cylinder 8412 presses the pre-assembly 8331 through the draw die 8404, which by generating pressure equally compresses (upsets) the Al 6061-T6 or Al7075-T6 aluminum alloy material of the waveguide shaft 8334 about the external circumference of the pre-assembly 8331 in the exact location of the blind cylindrical hole 8348 and Ti-6Al-4V ELI titanium alloy conical male end 8336 of the ultrasonic blade 8332, causing the Al 6061-T6 or Al7075-T6 aluminum alloy material to become plastic and uniformly reduce the hoop area, accounting for the spring back of the metal, to be permanently formed about the length and circumference of the Ti-6Al-4V ELI titanium alloy conical male end 8336, and retaining the waveguide shaft 8334 and ultrasonic blade 8332 components securely and permanently. Additionally, the Al 6061-T6 or Al7075-T6 aluminum alloy material of the waveguide shaft 8334 is heated by the heating element 8410 and cylinder 8408 to not more than 400° F. to facilitate additional plastic flow without loss of the wrought material properties or cracking/rupturing of the material.

The ultrasonic waveguide 8300 manufactured by this swaging process produces a two-piece assembly comprising the waveguide shaft 8302 and the ultrasonic blade 8306, that function similar to an ultrasonic surgical instrument component produced of a single homogeneous component material. In one aspect, the two-piece swaged ultrasonic waveguide 8300 functions well within the power requirement without significant thermal self-heating, achieves acceptable frequency lock, and achieves functional transverse and longitudinal displacement without breaking. The Al 7075-T6/Ti-6Al-4V ELI aluminum alloy/titanium alloy two-piece swaged waveguide 8300 functions substantially similar to a one-piece wrought Ti-6Al-4V ELI titanium alloy waveguide.

Figure 58:
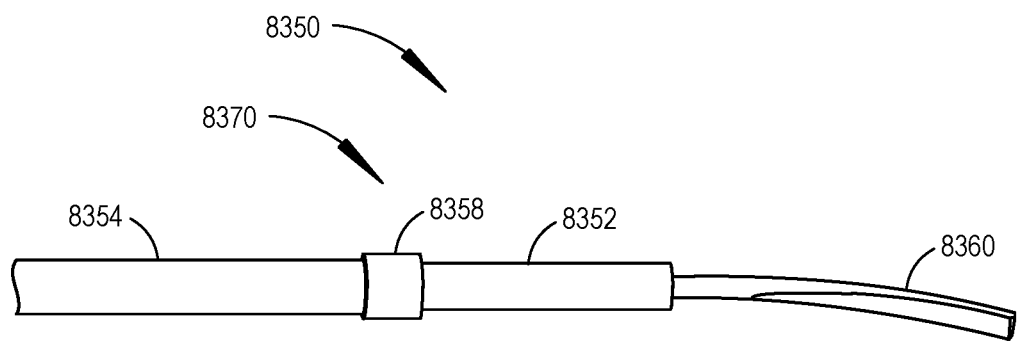
FIG. 58 is a side view of a two-piece ultrasonic waveguide comprising a waveguide shaft coupled to an ultrasonic blade by a swaged joint using the swaging process described in connection with FIGS. 48-57, according to one aspect of this disclosure.
Figure 59:
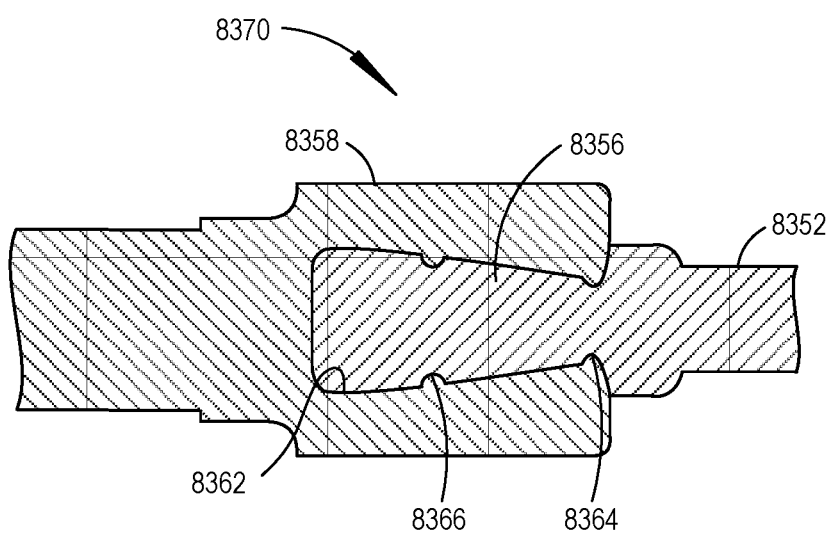
FIG. 59 is a section view of the swaged joint formed between the waveguide shaft and the ultrasonic blade, according to one aspect of this disclosure.
Figure 60:
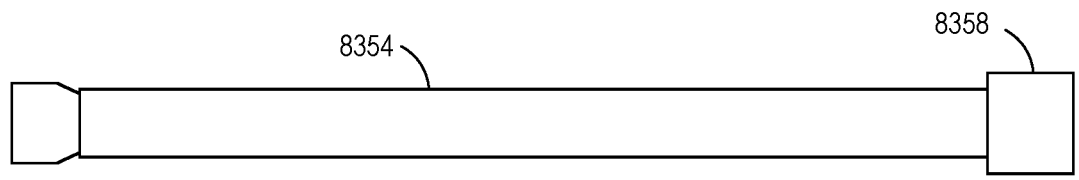
FIG. 60 is a side view of the waveguide shaft shown in FIG. 59, according to one aspect of this disclosure.
Figure 61:
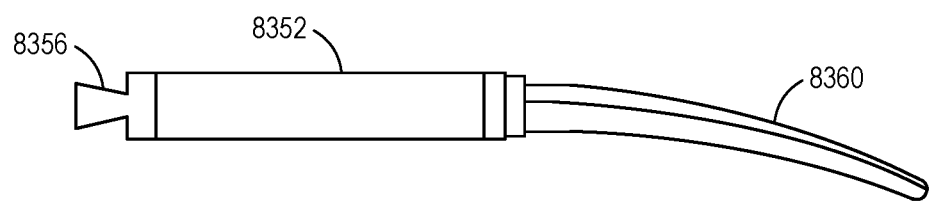
FIG. 61 is a side view of the ultrasonic blade is shown in FIG. 59, according to one aspect of this disclosure.
Figure 62:
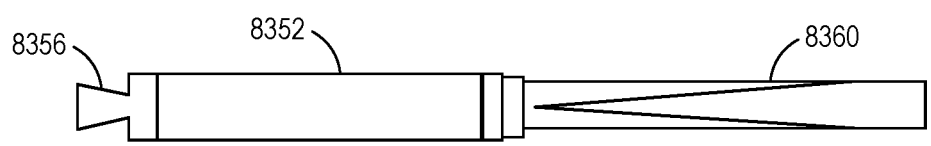
FIG. 62 is a plan view of the ultrasonic blade shown in FIG. 59, according to one aspect of this disclosure.

FIG. 58 is a side view of a two-piece ultrasonic waveguide 8350 comprising a waveguide shaft 8354 coupled to an ultrasonic blade 8352 by a swaged joint 8370 using the swaging process described in connection with FIGS. 48-57, according to one aspect of this disclosure. FIG. 59 is a section view of the swaged joint 8370 formed between the waveguide shaft 8354 and the ultrasonic blade 8352, according to one aspect of this disclosure. A side view of the waveguide shaft 8354 is shown in FIG. 60. A side view of the ultrasonic blade 8352 is shown in FIG. 61 and a plan view of the ultrasonic blade 8352 is shown in FIG. 62. The distal end of the ultrasonic blade 8352 defines a treatment portion 8360 for treating tissue is contact therewith. The proximal end of the ultrasonic blade 8352 is joined to the waveguide shaft 8354 at a collar 8358 portion about the cylindrical aperture located at the distal end of the waveguide shaft 8354. The distal end of the ultrasonic blade defines a male conical end 8356, which is received inside a cylindrical aperture 8362 defined by the collar portion 8359 of the shaft 8354. The male conical end 8356 defines two circumferential grooves 8364, 8366 to improve performance loss and retention of the ultrasonic blade 8352 component in the waveguide shaft 8354 component.

Figure 63:
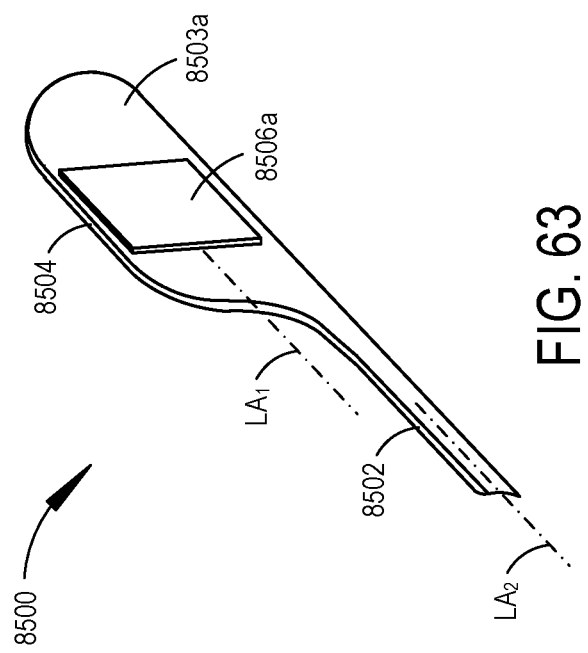
FIG. 63 illustrates an ultrasonic surgical instrument comprising an ultrasonic waveguide coupled to an offset ultrasonic transducer baseplate, according to one aspect of this disclosure.

FIG. 63 illustrates an ultrasonic surgical instrument 8500 comprising an ultrasonic waveguide 8502 coupled to an offset ultrasonic transducer baseplate 8504, according to one aspect of this disclosure. The transducer baseplate 8504 defines a flat face 8503*a* on each side to receive a PZT piezoelectric element 8506*a* on each side. The transducer baseplate 8504 defines a first longitudinal axis LA1 and the waveguide 8502 defines a second longitudinal axis LA, where the longitudinal axes are offset relative to each other.

Figure 64:
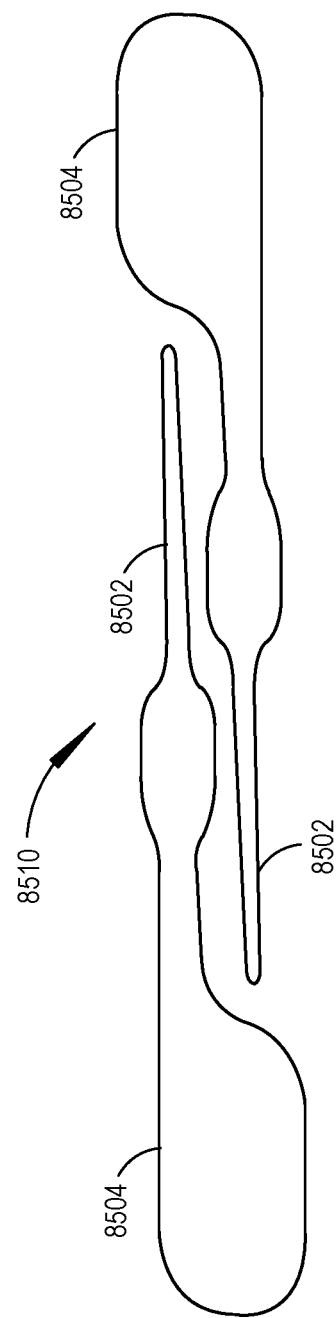
FIG. 64 illustrates two metal substrates components of the ultrasonic surgical instrument shown in FIG. 63 arranged in a complementary orientation for stamping or punching, according to one aspect of this disclosure.

FIG. 64 illustrates two metal substrates 8510 components of the ultrasonic surgical instrument 8500 shown in FIG. 63 arranged in a complementary orientation for stamping or punching, according to one aspect of this disclosure. Offsetting the proximal transducer baseplate 8504 end of the ultrasonic surgical instrument allows the substrates 8510 to be oriented in the complementary orientation to minimize material waste and maximize efficiency in material when the substrates are punched or stamped out of sheet metal. In various aspects, the sheet metal is titanium, titanium alloy, aluminum, aluminum alloy, among others.

Figure 65:
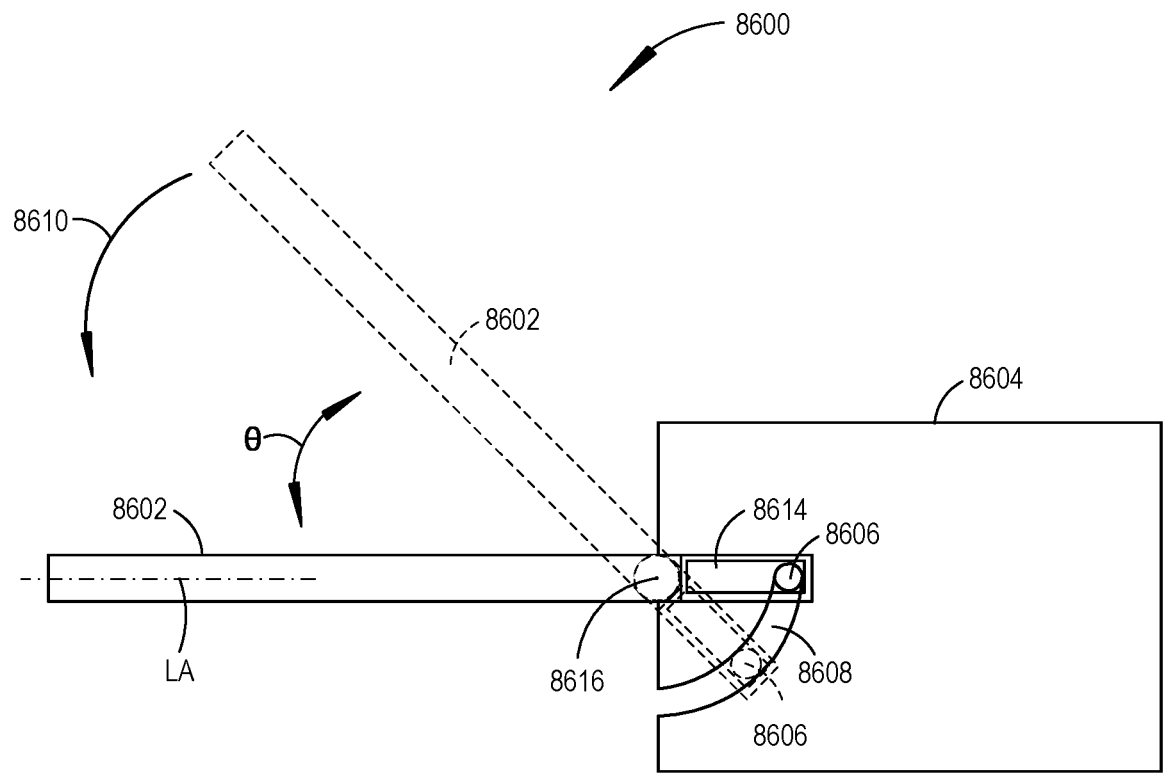
FIG. 65 is an ultrasonic surgical instrument configured in a D31 transducer architecture comprising separate ultrasonic waveguide and ultrasonic transducer base plate components shown in a coupled configuration, according to one aspect of this disclosure.
Figure 66:
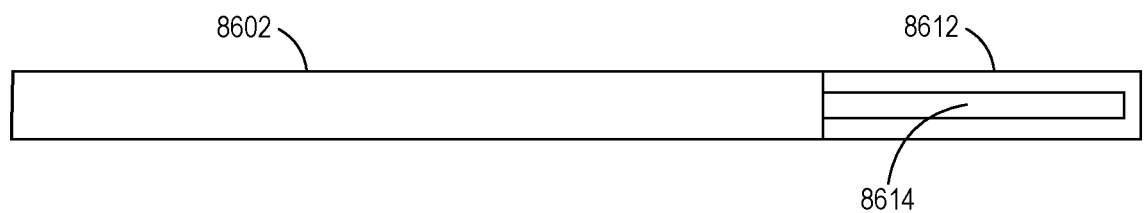
FIG. 66 is a side view of the ultrasonic blade, according to one aspect of this disclosure.

FIG. 65 is an ultrasonic surgical instrument 8600 configured in a D31 transducer architecture comprising separate ultrasonic waveguide 8602 and ultrasonic transducer base plate 8604 (e.g., a transducer mounting portion) components shown in a coupled configuration, according to one aspect of this disclosure. FIG. 66 is a side view of the ultrasonic blade 8602, according to one aspect of this disclosure. With reference now to FIGS. 65 and 66, the ultrasonic blade 8602 pivots about pivot point 8616 into a groove 8608 formed in the transducer baseplate 8604 with increasing interference as it rotates 8610. The ultrasonic blade 8602 includes a window 8612 defining a slot 8614 to engage a pin 8606 in the groove 8608. The ultrasonic blade 8602 assembles to the transducer base plate 8604 at an angle θ and is then rotated 8610 while the blade 8602 rotating interface increases at the proximal end of the blade 8602 with the groove 8608 in the transducer baseplate 8604.

Figure 67:
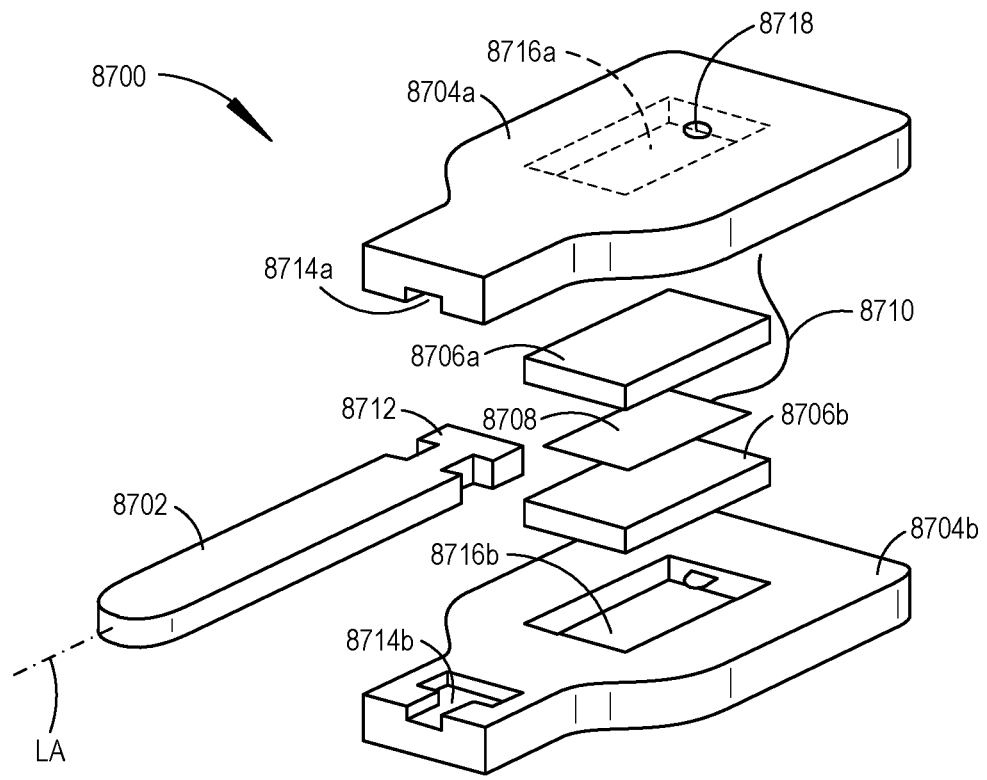
FIG. 67 is an exploded view of an ultrasonic surgical instrument configured in a D31 transducer architecture comprising separate ultrasonic waveguide and symmetric two-piece clamshell housing components to support ultrasonic transducer piezoelectric elements, according to one aspect of this disclosure.
Figure 68:
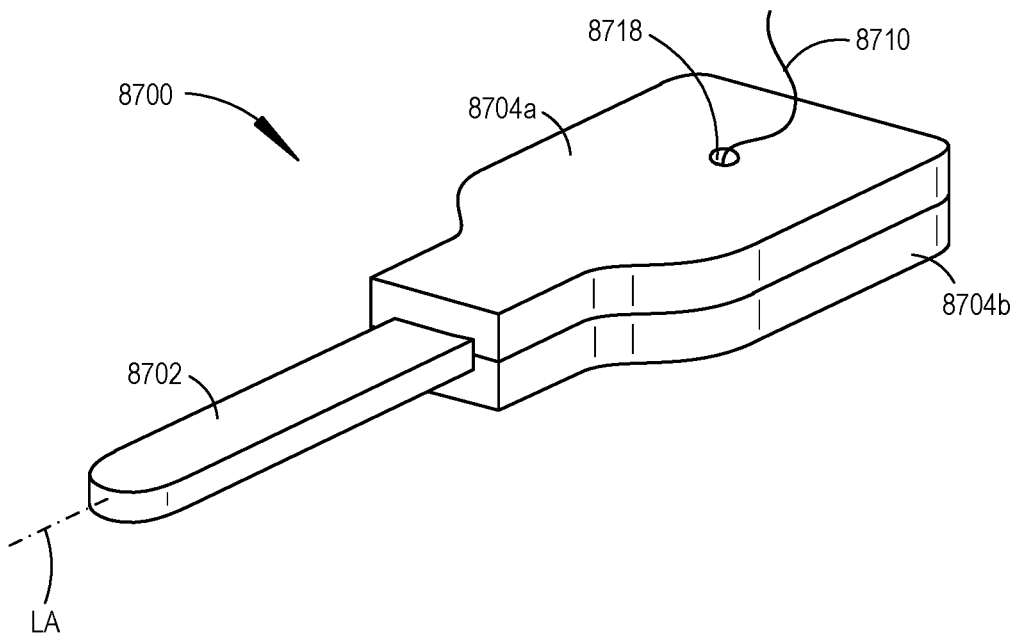
FIG. 68 is an assembled view of the ultrasonic surgical instrument shown in FIG. 67, according to one aspect of this disclosure.

FIG. 67 is an exploded view of an ultrasonic surgical instrument 8700 configured in a D31 transducer architecture comprising separate ultrasonic waveguide 8702 and symmetric two-piece clamshell housing components 8704*a*, 8704*b* to support ultrasonic transducer PZT piezoelectric elements 8706*a*, 8706*b*, according to one aspect of this disclosure. FIG. 68 is an assembled view of the ultrasonic surgical instrument 8700 shown in FIG. 67, according to one aspect of this disclosure. With reference now to FIGS. 67 and 68, a proximal end of the ultrasonic blade 6702 defines a T-shaped male connector 8712 that is received in corresponding T-shaped pockets 8714a, 8714b defined in respective top and bottom clamshell housing components 8704a, 8704b. The symmetric two-piece clamshell housing components 8704a, 8704b defines recessed pockets 8716a, 8716b to retain PZT piezoelectric elements 8706a, 8706b. The T-shaped pockets 8714a, 8714b are press fit to the T-shaped male connector 8712 of the ultrasonic blade 8702 when the two-piece clamshell housing components 8704a, 8704b are pressed together. An electrode 8708 is disposed between the PZT piezoelectric elements 8706a, 8706b and an electrically conductive element (e.g., wire tail) is disposed through an aperture 8718 defined in the top clamshell housing component 8704a. Each of the two-piece clamshell housing components 8704a, 8704b is made of an electrically conductive material and act as the other electrode. The clamshell housing components 8704a, 8704b are also thermally conductive and act as a heat sink. The clamshell housing components 8704a, 8704b are either pressed, bolted, banded, or welded together.

Figure 69:
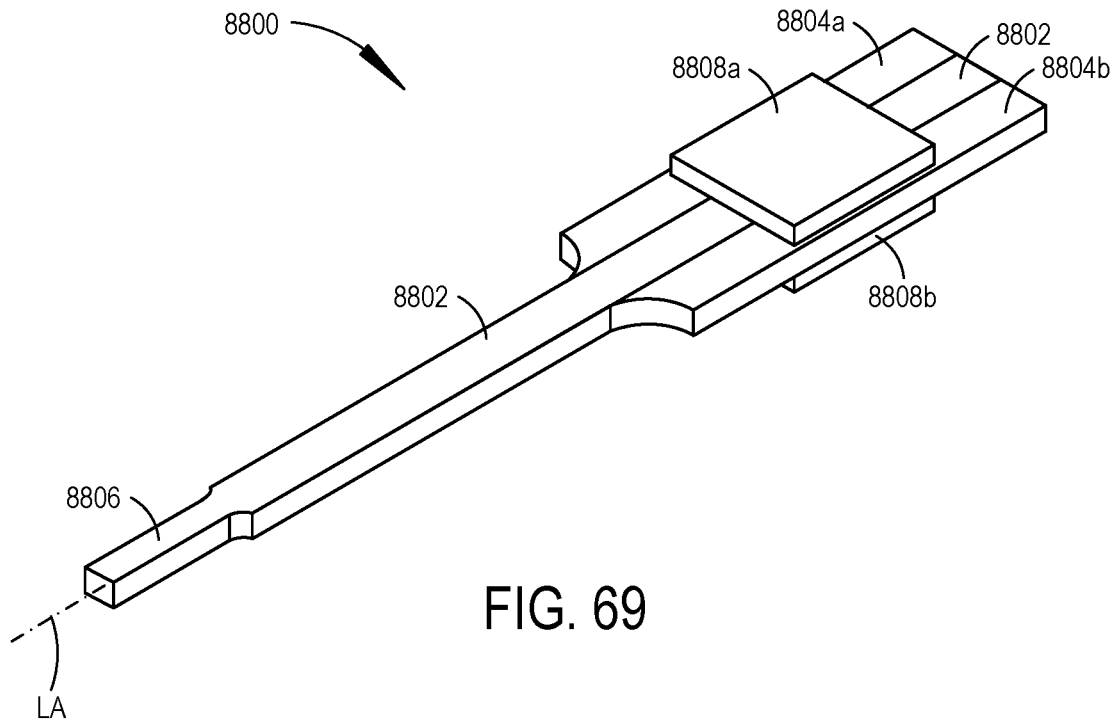
FIG. 69 is a perspective view of an ultrasonic surgical instrument configured in a D31 transducer architecture comprising separate ultrasonic waveguide and a two-piece ultrasonic transducer base plate to support PZT piezoelectric elements, according to one aspect of this disclosure.
Figure 70:
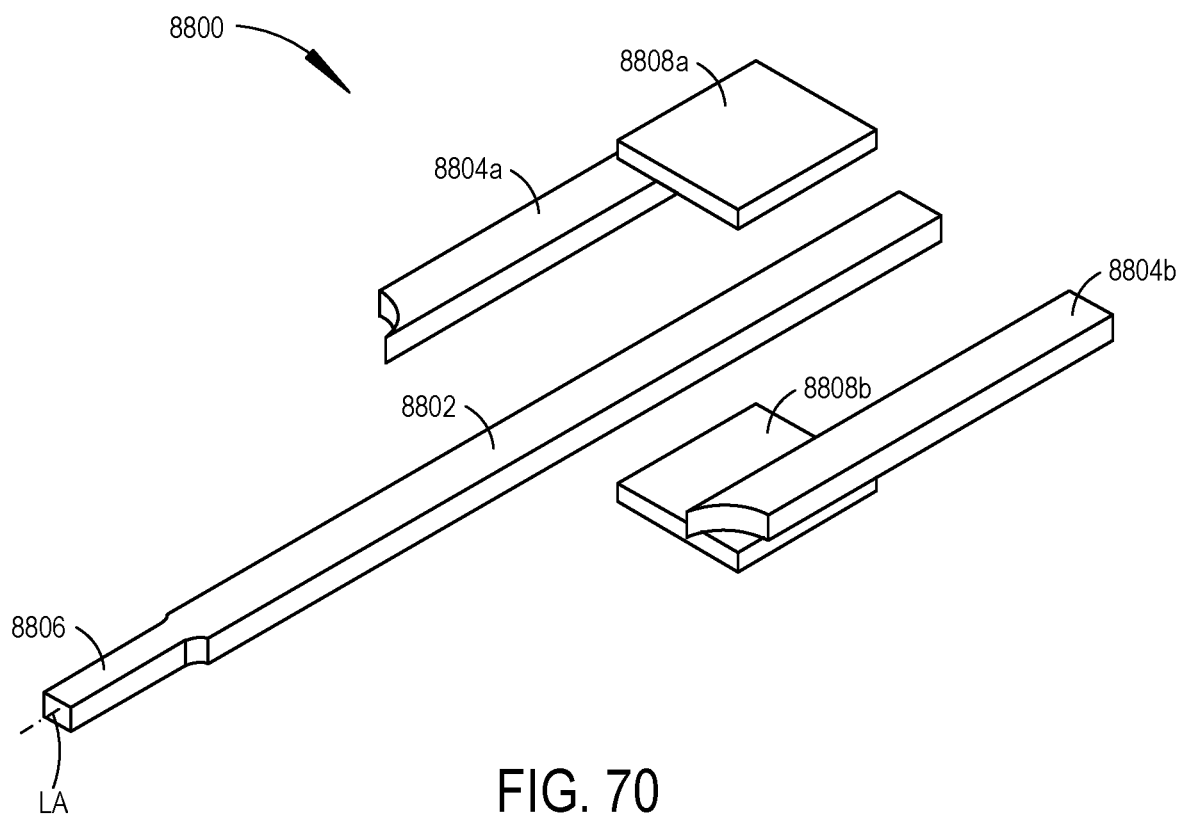
FIG. 70 is an exploded view of the ultrasonic surgical instrument shown in FIG. 69, according to one aspect of this disclosure.

FIG. 69 is a perspective view of an ultrasonic surgical instrument 8800 configured in a D31 transducer architecture comprising separate ultrasonic waveguide 8802 and a two-piece ultrasonic transducer base plate 8804a, 8804b (e.g., a transducer mounting portion) to support PZT piezoelectric elements 8808a, 8808b, according to one aspect of this disclosure. FIG. 70 is an exploded view of the ultrasonic surgical instrument 8800 shown in FIG. 69, according to one aspect of this disclosure. With reference now to FIGS. 69 and 70, a distal end of the ultrasonic waveguide 8802 defines a blade 8806 for treating tissue in contact therewith. The ultrasonic surgical instrument 8800 comprises three sections joined together by bonding, resin, or brazing. A central section is the waveguide 8802 and lateral sections 8804a, 8804b are added to increase the width as needed to support the PZT piezoelectric elements 8808a, 8808b. This technique saves material and saves valuable titanium or titanium alloy compared with the method of machining the waveguide and transducer base plate out of a single material blank.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although various aspects have been described herein, many modifications and variations to those aspects may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered examples:

Example 1

An ultrasonic surgical instrument, comprising: a waveguide comprising a distal end configured as a blade and a proximal end configured to couple to a transducer base plate; and the transducer base plate comprising a distal end coupled to the proximal end of the waveguide to define a joint at an interface between the waveguide and the transducer base plate, the transducer base plate comprising a first and second sides defining corresponding first and second flat faces, wherein the first flat face is configured to receive a first piezoelectric element and the second flat face is configured to receive a second piezoelectric element, wherein the first and second piezoelectric elements are configured to operate in a D31 mode.

Example 2

The ultrasonic surgical instrument of Example 1, wherein the waveguide is made of a first material and the transducer base plate is made of a second material that is different from the first material.

Example 3

The ultrasonic surgical instrument of Example 1 or Example 2, wherein the first material comprises titanium or a titanium alloy and the second material comprises aluminum or an aluminum alloy.

Example 4

The ultrasonic surgical instrument of one or more of Example 1 through Example 3, wherein the proximal end of the waveguide defines a jigsaw puzzle piece and the distal end of the transducer base plate defines a complementary mating jigsaw puzzle piece configured to receive the jigsaw puzzle piece defined by the proximal end of the waveguide.

Example 5

The ultrasonic surgical instrument of Example 4, wherein the proximal end of the waveguide defines a tapered end and the distal end of the transducer base plate defines an aperture defining a tapered wall, wherein the aperture is configured to receive the tapered end to form an interference joint.

Example 6

The ultrasonic surgical instrument of one or more of Example 4 through Example 5, wherein the waveguide defines at least one female jigsaw puzzle piece on a first side and the transducer base plate defines at least one male jigsaw puzzle piece configured to receive the at least one female jigsaw puzzle piece to form a thermal expansion joint.

Example 7

The ultrasonic surgical instrument of one or more of Example 4 through Example 6, further comprising a C-shaped pin press fit between the proximal end of the waveguide and the distal end of the transducer base plate.

Example 8

The ultrasonic surgical instrument of one or more of Example 1 through Example 7, wherein the proximal end of the waveguide defines at least two bumps and the distal end of the transducer base plate defines an aperture that defines at least two apertures, wherein the aperture is configured to receive the proximal end of the waveguide and the at least two bumps defined on the proximal end of the waveguide form an interference fit with the at least two bumps defined by the aperture.

Example 9

The ultrasonic surgical instrument of one or more of Example 1 through Example 8, wherein the proximal end of the waveguide defines a male threaded end and the distal end of the transducer base plate defines a complementary female threaded end configured to receive the male threaded end defined by the proximal end of the waveguide.

Example 10

The ultrasonic surgical instrument of one or more of Example 1 through Example 9, wherein the proximal end of the waveguide defines a female threaded end and the transducer base plate defines an aperture to receive a screw therethrough and the threadingly engage the female threaded end of the waveguide.

Example 11

The ultrasonic surgical instrument of Example 10, wherein the proximal end of the waveguide defines a conical feature that matches a complementary conical channel defined by the distal end of the transducer base plate.

Example 12

The ultrasonic instrument of one or more of Example 1 through Example 11, wherein the proximal end of the waveguide defines a wedge and the distal end of the transducer baseplate defines a complementary mating notch to receive the wedge, wherein the distal end of the transducer base plate defines female threaded apertures laterally disposed from the notch and the proximal end of the waveguide comprises flanges laterally disposed from the wedge, wherein the flanges defines apertures, and wherein in a coupled configuration the apertures align with the female threaded apertures defined by the distal end of the transducer base plate.

Example 13

The ultrasonic surgical instrument of one or more of Example 1 through Example 12, wherein the distal end of the transducer base plate defines a luer male thread and the waveguide comprises a slidable luer nut configured to engage the luer male thread to define a luer lock joint between the waveguide and the transducer base plate.

Example 14

The ultrasonic surgical instrument of one or more of Example 1 through Example 13, wherein the proximal end of the waveguide defines a first flange that is complementary and mates with a second flange defined at the distal end of the transducer base plate, wherein the first flange defines an aperture sized and configured to receive a pin defined by second flange sized and configured to achieve an interference flange joint between the waveguide and the transducer base plate.

Example 15

The ultrasonic surgical instrument of one or more of Example 1 through Example 14, wherein the proximal end of the waveguide defines a first flange that is complementary and mates with a second flange defined at the distal end of the transducer base plate, wherein the first and second flanges define first and second apertures sized and configured to receive a pin therethrough, wherein the pin and the first and second apertures are sized and configured to achieve an interference joint between the waveguide and the transducer base plate.

Example 16

The ultrasonic surgical instrument of one or more of Example 1 through Example 15, wherein the proximal end of the waveguide defines at least two apertures and a distal end of the transducer base plate defines a recessed receptacle configured to accept a profile of the proximal end of the waveguide, wherein the recessed receptacle defines at least two apertures, wherein the ultrasonic surgical instrument further comprises at least two fasteners disposed through the at least two apertures defined by the waveguide and the at least two apertures defined by the recessed receptacle of the transducer base plate to lock the waveguide and the transducer base plate in place by a parallel tang attachment joint.

Example 17

The ultrasonic surgical instrument of claim one or more of Example 1 through Example 16, wherein the distal end of the transducer base plate defines a notch to receive the proximal end of the waveguide, wherein the distal end of the transducer base plate defines a transverse pin opening and the proximal end of the waveguide defines a transverse pin opening and a pin press fit through the transverse pin openings defined by the distal end of the transducer base plate and the proximal end of the waveguide to achieve an interference pin joint.

Example 18

The ultrasonic surgical instrument one or more of Example 1 through Example 17, wherein the waveguide defines a first longitudinal axis and the transducer base plate defines a second longitudinal axis, wherein the first longitudinal axis is offset from the second longitudinal axis.

Example 19

An ultrasonic waveguide, comprising: a shaft comprising a proximal end and a distal end, wherein the proximal end is configured to couple to an ultrasonic transducer and the distal end defines cylindrical aperture with a flat perpendicular bottom configured to receive a proximal end of a blade; and a blade attached to the shaft, the blade comprising a distal end for treating tissue and a proximal end defining a conical male end defining a flat perpendicular bottom, wherein the conical male end defines a proximal diameter and a distal diameter, wherein the proximal diameter is larger than the distal diameter, and wherein the conical male end is received into the cylindrical aperture defined by the distal end of the shaft.

Example 20

The ultrasonic waveguide of Example 19, wherein the blade is joined to the shaft by a swaged joint.

Example 21

The ultrasonic waveguide of Example 20, wherein the swaged joint is formed by a warm die swaging process.

Example 22

The ultrasonic waveguide of one or more of Example 19 through Example 21, wherein the conical male end defines a first circumferential groove at or near the distal diameter and defines a second circumferential groove between the proximal and distal diameters.

Example 23

The ultrasonic waveguide of one or more of Example 19 through Example 22, wherein the distal end of the shaft defines at a collar about the cylindrical aperture.

Example 24

The ultrasonic waveguide of one or more of Example 19 through Example 23, wherein the shaft is made of a first material and the blade is made of a second material.

Example 25

An ultrasonic surgical instrument, comprising: an ultrasonic waveguide defining a T-shaped male connector at a proximal end; and a symmetric two-piece clamshell housing comprising: first and second T-shaped pockets configured to receive the T-shaped male connector, wherein the T-shaped pockets are press fit to the T-shaped male connector; and first and second recessed pockets configured to support first and a second piezoelectric elements, wherein the first and second piezoelectric elements are configured to operate in a D31 mode.

Example 26

The ultrasonic surgical instrument of Example 25, further comprising a first electrode disposed between the first and second piezoelectric elements and an electrically conductive element disposed through an aperture defined in one of the two-piece clamshell housing.

Example 27

The ultrasonic surgical instrument of Example 25 or Example 26, wherein each of the two-piece clamshell housing components is made of an electrically conductive material to act as a second electrode.

Example 28

The ultrasonic surgical instrument of Example 25 or Example 26, wherein each of the two-piece clamshell housing components is made of a thermally conductive material to act as a heat sink.

The invention claimed is:

1. An ultrasonic surgical instrument, comprising:
a waveguide comprising a distal end configured as a blade and a proximal end configured to couple to a transducer base plate, the proximal end defining a jigsaw puzzle piece with a tapered end comprising a first male connecting surface having a first width at a distal extremity of the jigsaw puzzle piece, and a second male connecting surface opposite the first male connecting surface and having a second width at the distal extremity of the jigsaw puzzle piece, wherein the first width is wider than the second width; and
the transducer base plate comprising:
a distal end defining a complementary mating jigsaw puzzle piece with a tapered receiving aperture configured to receive the jigsaw puzzle piece defined by the proximal end of the waveguide such that the transducer base plate distal end couples to the proximal end of the waveguide to define a joint at an interface between the waveguide and the transducer base plate;
first and second sides defining corresponding first and second flat faces, wherein the first flat face is configured to receive a first piezoelectric element and the second flat face is configured to receive a second piezoelectric element, wherein the first and second piezoelectric elements are configured to operate in a D31 mode,
wherein the first flat face extends to the distal end of the transducer base plate and defines, as part of the complementary mating jigsaw puzzle piece, a first female connecting surface having a third width at a proximal extremity of the complementary mating jigsaw puzzle piece,
wherein the second flat face extends to the distal end of the transducer base plate and defines, as part of the complementary mating jigsaw puzzle piece, a second female connecting surface, opposite the first female connecting surface and having a fourth width at the proximal extremity of the complementary mating jigsaw puzzle piece, wherein the third width is wider than the fourth width; and
wherein the first male connecting surface is configured to connect with the first female connecting surface and the second male connecting surface is configured to connect with the second female connecting surface.

2. The ultrasonic surgical instrument of claim 1, wherein the waveguide is made of a first material and the transducer base plate is made of a second material that is different from the first material.

3. The ultrasonic surgical instrument of claim 2, wherein the first material comprises titanium or a titanium alloy and the second material comprises aluminum or an aluminum alloy.

4. The ultrasonic surgical instrument of claim 1, wherein the second width is wider than the fourth width.

* * * * *